United States Patent
She et al.

(10) Patent No.: US 7,033,816 B1
(45) Date of Patent: Apr. 25, 2006

(54) ACTIVATORS OF CYCLIN-DEPENDENT KINASES

(75) Inventors: Jin-Xiong She, Martinez, GA (US); Cong-Yi Wang, Martinez, GA (US); Pradeep G. Kumar, Gainesville, FL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 595 days.

(21) Appl. No.: 10/199,229

(22) Filed: Jul. 19, 2002

Related U.S. Application Data

(60) Provisional application No. 60/306,835, filed on Jul. 19, 2001.

(51) Int. Cl.
*C12N 15/12* (2006.01)
*C12N 1/20* (2006.01)
*C07H 21/04* (2006.01)

(52) U.S. Cl. ............................. 435/252.3; 435/320.1; 536/23.2

(58) Field of Classification Search ................ 435/194, 435/320.1, 252.3, 6, 69.1; 536/23.2
See application file for complete search history.

(56) References Cited

OTHER PUBLICATIONS

Databank on Genbank, Accession No. Q9JIM7, Wang et al., "Characterization of mACPD1, mACDP2, mACDP3 and mACDP4, the mouse homologs of human ACDO gene family," Oct. 01, 2000.
Database on Genbank, Accession No. AF169226, Wang et al., "Identification of ACDP1—a member of a new gene family and its exclusion as a candidate for the Urofacial (ochoa) Syndrome (UFS) on chromosome 10q23-10q24," Jul. 19, 2000.
Database on Genbank, Accession No. AF216962, Wang et al., "Identification of novel gene family (ACDP) conserved for C. elegans to human, molecular characterization of ACDP2, ACDP3 and ACDP4," Jul. 19, 2000.
Database on Genbank, Accession No. AF216965, Wang et al., "Identification of novel gene family (ACDP) conserved for C. elegans to human, molecular characterization of ACDP2, ACDP3 and ACDP4," Jul. 19, 2000.
Database on Genbank, Accession No. AF202777, Wang et al., "Identification of a novel gene family (ACDP) conserved for C. elegans to human, molecular characterization of ACDP2, ACDP3, and ACDP4," Jul. 19, 2000.
Database on Genbank, Accession No. AF202994, Wang et al., "Characterization on mACPD1, mACDP2, mACDP3 and mACDP4, the mouse homologs of the human gene family," Jul. 19, 2000.
Databank on Genbank, Accession No. AF216961, Wang et al., "Characterization of mACDP1, mACDP2, mACDP3 and mACDP4, the mouse homologs of the human ACDP gene family", Jul. 19, 2000.
Databank Genbank, Accession No. AF 216963, Wang et al., "Characterization of mACDP1, mACDP1, mACDP2, mACDP3 and mACDP4, the mouse homolog of the human gene family," Jul. 19, 2000.

*Primary Examiner*—Maryam Monshipouri
(74) *Attorney, Agent, or Firm*—Akerman Senterfitt

(57) ABSTRACT

A new gene family involved in cell cycle regulation was discovered. This family has been termed activators of cyclin-dependent kinases (ACDKs). A number of ACDK genes have been cloned and sequenced. Proteins encoded by ACDK genes specifically were shown to interact with CDKs and pRb, and to upregulate the kinase activity of a CDK using pRb as a substrate. Progression of a cell through the cell cycle can be regulated by modulating ACDK expression in the cell.

6 Claims, 3 Drawing Sheets

```
ACDK1 : MLRSDAVLDFATVSEILRSGYTRIPVYEG-DQRHNIVDILFVKDDLAFVDP--DDCTPLLTVTRFYNPPLHCVFNDTRLL :  75
ACDK2 : MITGEAILDFNTMSEIMESGYTRIPVFE--QERSNIVDLLFVKDDLAFVDP--DDCTPLKTITKFYNHPLHFVFNDTKLL :  74
ACDK3 : MLDASTVLDFGQLASIMQSGHTRIPVYE--EERSNIVDMLYLKDDLAFVDP--EDCTPLSTITRFYNHPLHFVFNDTKLL :  74
ACDK4 : MIRSDAILDFNTMSEIMESGYTRIPVFE--DEQSNIVDILYVKDDLAFVDP--DDCTPLKTITRFYNHPVHFVFHDTKLL :  74
DroM  : MLSLDALLDFETVSEIMNSGYSRIPVYDG-D-RKNIVTLLYIKDDLAFVDT--DDQTPLKTLCFFYQNPVHFVFHDYLLL :  74
SSC   : -MSADTILDDKTVEKIFNSGFSRIPIFLP-NEPNNFIGMLLVRRRLISYDP--DDCLP---ISHFPLATLPETSPNTSCC :  71
CanG  : -LSADKILDEKTIEEIFNSGFSRIPIHLP-NEPMNFIGMLIVRTTLISYDP--EDALP---ISSFPLATLPETSPNTSCC :  71
SchP  : -LPMDRILDEDLIGEICAGYSRIPVHKP-GFPHDFIGMLTKTTLGYDP--DDKWP---VGKFALATLPQTWPNTSCC :  71
PM70  : -IHTDQMLD-SCLDTIIVSAHSRFPVIT--DERDNIAGILHAKDDLLRFLR---SQAEEFDLMPLL-RPAVIVPESRRVV :  70
HaeI  : ------------LNTIIESAHSRFPVIADADDRDNIVGILHAKDDLLKFLR---EDAEVFDLSSLL-RPVVIVPESRRVV :  62
PA01  : ----------IRRHKYSRFPVWDS--HKGEFIGLLHIKDDLLLALSALD-SLPETFDLDKLV-RPLEIVTKHTPLL :  60
CaeE  : MLPDTTVLNAKTVMEIVKMGYTRIPVYQY-GDKNNVTDMLFVKDDLALLDP--DDNFTVKTVCGYHKHPVKFVMNDTPLL :  75

*              *              *              *              *
                 80             100            120            140

ACDK1 : DTVLEEFKKG-KSHLAIVQR-VNNEGEGDPFYEVMGIVTLEDIIEEIIRSEILDETDLYTDNRKKQRVPQRER---KR : 148
ACDK2 : DIMLEEFKKG-KSHLAIVQR-VNNEGEGDPFYEVLGIVTLEDVIEEIIRSEILDETDLYTDNRTKKKVAHRER---K : 146
ACDK3 : DIVLEEFKRG-KSHLAIVQK-VNNEGEGDPFYEVLGLVTLEDVIEEIIPSEILDESDDYRDTVVKKKPASLMAPLKRK : 150
ACDK4 : DIMLEEFKKG-KSHLAIVQK-VNNEGEGDPFYEVLGLVTLEDVIEEIIHSEILDESDMYTDNRSRRRVSEKN---K : 145
DroM  : DIMFNQFKEGTIGHIAPVHR-VNNEGDGDPFYETVGLVTLEDVIEELIQAEIVDETDVFVDNRTKTR-.RNRYK---K : 146
SSC   : LNILNYFQEG-KAHMDVVSK-EPGSSHG------AIGVLTLEDVIEELIGEEIVDESDVFVDNHQHIMRQQPGPLSKRH : 142
CanG  : LNILNYFQEG-KSHMOIVSK-RPGSSNGS-----AIGVITLEDIIEELIGEEIIDETDVYIDVHK--- : 125
SchP  : LDLLNYCQEG-KSHMILVSN-SPGKPHG-------DEFGAVSGLVTIEDILEQIVG-DIKDEFDEEEIVNIRQGS--- : 128
PM70  : DRMLKDFRSE-RFHMAIVV-------DEFGAVSGLVTIEDILEQIVG-DIRDEFDEEEIADIRQLS--- : 127
HaeI  : DRMLKDFRSE-RFHMAIVV--------HKVVGFLTMEDVLEVLVG-DIQDEHRKTERG-ILAYQ--- : 119
PA01  : SRLLEQFRKG-GAHFAVVEK-AD-------HKVVGFLTMEDVLEVLVG-DIQDEHRKTERG-ILAYQ--- : 116
CaeE  : PNLLEAFKKG-HGHLAMVKRLINTDDKHDPEYVLVGVVT--- : 113
```

FIG. 1

SEQUENCE LISTING

```
<160> NUMBER OF SEQ ID NOS: 16

<210> SEQ ID NO 1
<211> LENGTH: 5747
<212> TYPE: DNA
<213> ORGANISM: homo sapiens

<400> SEQUENCE: 1
tctcgctcgg cttcctgcag tatcacgtgc agctgcgctg ggtgcaggat ggcggcggcc      60
gcggcggcgg cagcagcggt gggtgtcagg ctccgggact gctgcagccg aggcgctgtg     120
ctcctgctct tcttttccct gtctcctcgg ccccccggccg ccgccgcctg gctgctgggc     180
ctgcggcccg aggacactgc tggaggccgc gtgtccctgg aggggggcac cctgcgcgcc     240
gccgaaggca ccagcttcct cctgcgtgtc tatttccagc caggaccgcc ggccaccgcc     300
gcaccggtgc cctcaccgac cctcaactcg ggggagaatg caccggcga ctgggctccg      360 cggctcgtgt tcatcgagga gccccccgggc ggtggcggcg tggcccccag cgcggtcccc     420
actcgccccc cgggaccgca gcgctgcagg gagcagagcg actgggcatc ggacgtggaa     480
gtcctggggc ccttgcgtcc cggggggcgtg gcaggctcgg ccctggtcca ggtgcgagtg     540
cgggagctgc gcaagggcga agcggagcgg ggcggcgcg cggtggcgg gaagctcttt     600 tcactctgcg cctgggatgg gcgcgcgtgg caccaccacg gcgccgccgg cggcttcctg     660
ctgcgcgttc gcccgcggtt gtacgcccca ggcgggggacc tgctgccccc tgcgtggctg     720
cgggcgctcg gggcgctcct gctgctagcc ttgtcggccc tgttcagcgg cctgcgcctg     780
agcctgctgt cgctggaccc ggtggagtta cgggtgctgc ggaacagcgg ctcggccgcc     840
gagcaggagc aggcgcgccg cgtgcaggcc gttcgcggca gggggaccca tctgctctgc     900
accctactcc tgggccaagc cggagccaac gcggccctgg ctggctggct gtacacctcg     960
ctgccgccgg gcttcggggg caccggggaa gactacagcg aagaggggat ccacttcccg    1020
tggctgccgg cgctcgtgtg caccggcgcg gtattcctgg gcgccgaaat ctgcccctac    1080
tcagtgtgtt cgcggcacgg gctggccatc gcctcgcaca gcgtgtgcct gacccggctt    1140
ctgatggcag ccgccttccc cgtgtgctac ccgctgggcc gctgctgga ctgggcgctg    1200 cgccaggaga taagcacctt ctacacgcgg gagaagttgc tggagacgtt gcgggccgca    1260 gaccctaca gtgacctggt gaaggaggag ctcaacatca tacagggtgc cctggagctg    1320
cgcaccaaag tggtggagga ggtgctgacc ccctgggag actgcttcat gctgcgctca    1380
gacgcggtgc tcgacttcgc cactgtctcc gagatcctgc gcagcggcta cactcgcatc    1440
ccagtgtacg agggtgacca gcggcacaac attgtggaca ttttatttgt caaggacttg    1500
gccttcgtgg accccgacga ctgcacccccg ctcctcactg tcacccgctt ctacaaccgg    1560
cccctgcatt gtgtttcaa tgacacccga ctggacacgg ttctggagga gtttaagaag    1620
```

-continued

```
ggaaaatctc acctggccat tgtccagcgg gtgaataatg agggagaagg ggaccctttc      1680
tatgaggtga tgggcattgt cacgctggag gatatcatag aggagattat caagtcggag      1740
atcctggatg aaactgatct ctacactgac aatcggaaaa agcagagggt cccgcaacgg      1800
gagcggaagc ggcatgactt ctccttgttt aagctttcgg acacggagat gcgggtgaag      1860
atctcaccac agcttctgct agccacacac cgcttcatgg ccacagaagt ggagcccttt      1920
aagtctctgt acctttcgga gaagatcctg ctccggctcc tgaaacatcc caacgtgatc      1980
caggagctga agtttgatga agaacaag aaggccccgg aacactacct caccagcgca       2040
accgccctgt ggactacttt gtgctgcttc tacagggtaa agtggaggtg gaggttggta      2100
aggaaggcct tcgctttgaa aatggagcct ttacttacta tggcgtccca gccatcatga      2160
ccactgcttg ctcagataat gacgtgcgga aggttgaag tctggctgga tcttctgtct       2220
ttctaaaccg gtccccttct cgctgcagtg ggttgaatcg ctctgagtct ccaaaccgag      2280
agcgcagtga ctttgggggc agcaacaccc agctgtacag cagcagcaac aacctctaca     2340
tgcctgacta ctcagtccac atcctcagcg atgtgcagtt tgtgaagatc acacggcagc     2400
aatatcagaa cgcactcact gcctgccaca tggacagctc acctcagtcc cctgacatgg     2460
aggccttcac agacggggac tccactaagg cccccacaac ccggggcaca ccccagaccc     2520
ctaaggatga ccccgccatc acgctcctca acaacaggaa cagcctgccg tgcagccgct     2580
cagacgggct gagaagcccc agcgaggtag tgtacctgag gatggaggag ctggccttca     2640
cccaggaaga aatgactgac ttcgaggagc acagcacaca gcagctcacg ctgtctcctg     2700
cagccgttcc cacgagagca gcatcagata gtgaatgttg taacatcaac ctggatacag     2760
agaccagccc ctgcagtagc gattttgagg aaaacgtggg caagaagctg ctgagaacct     2820
tgagtggcca aaaaggaag aggtcaccag aaggagagag aacctctgag gacaactcca      2880
atttaacacc tctgatcaca tgacagggca aagccagcat tcactgggtg tgtgaaattc     2940
cagagctttg ggggagaatc caccctccca tcatctgctt cccccaaggc ctcccacagg     3000
tgacagaatg ttctgccttc ccttccatct cttcaccct agctgtcagt ttggcagatt      3060
ttccctcgtt acctccagtt cgactcagaa ccttgacatg gccataacag aaggaggtgc     3120
ctctgataga acatgctaga aatggtcttt tccacagcat agtctgggac tggaaaagag     3180
atgtctgact gcaagctgac aatgccactc tgggacccct gatgctcttc tttgttcttt     3240
gggtcccctg atgccatagg agacctatcg tcttggaact tgccattctt tcctccagaa     3300
caaaatgtta actttctaac acatttcatg catagcttgg ctcagaaggt gccattggca     3360
gacaggcaca tggaggctg gagtaggagg tctgaagatt agttcagggg atggaccaag      3420
aatttccccc agagctttaa agaagtggga ctcagccatg ttggcgcgtg attgacatta     3480
cagcacagaa aactgttagt gactggtttc ctgttagata agggttccag cagcctgggg    3540
cagtatgtct cagctggaat ggaagaatg tgagatggaa cctcaagtca ctgtttttac      3600
cagggacaca tctgtttgg ctcccaatca gcagtcttca atcgatcaat aattctgctc      3660
tggaagagaa ggaacaggga gcagagagac ccaactggga gccagagatg gaacttcagg    3720
tcttaagtgc aaatcaaagc aaaaaacaaa caaaacttac atggaaaaac tgtaagtgct    3780
gaaagcaagt ttagccatga caaaccaaag agtgccagg tcagccaaga agatacata      3840
atctcatggg acttcagtgg gagttacaca ggaatgttga agaatcattc ttcttttttca    3900
tgcatttgtc cttctcccac ccccttacta caccctagca gatcagctga gtgtacttta    3960
ttccaagaac ttactggatc tctggttttt ctcctgaagt tggggcaggt gcaattccaa    4020
```

-continued

```
gcataaccac cagatggcag agtgaccgcg catacctgct tccaagaata aaacagttct    4080
gaaaagcaac cgcaaagccg ggcgcggtgg ctcacacctg taatcccaac agtttggaag    4140
accgaggcgg gtggatcact tgaagtcagg agtttgagac cagcctggcc aacatggtga    4200 aaccccatc tctcctgggc atgtagtccc agctactcgg gaggctgagg caggagaatc     4260
gcttgaacct gggaggcaga ggttgcagtg agctgagatc acaccactgc acttcatcct    4320
aggcaacaga gcgagactct gtctccccc tcaaaaaaa aaagaaaga aagaaagaga       4380 aaagaaaaga aaagcaacca cagccagcct tagggaaaac ttggaagtaa gtgaaatttg    4440
tcttcagaat aactatctcc ctttctgatc tgtctcctac tctttagatg ttctcagtca    4500
agtactcact gaactcattg atcgagtgct gtctgctaaa tctccaaacc attcccaaac    4560
ctttccccgt agtataccat ccagcttccc tccccttcct ccaaaaccct cctcccacc     4620 tccccacacc cattgagtca ttcacaggca ggagggagac tgatcattcc tctgggttat    4680
ctgcatctca aaagaaaatg cttacccaca ggaactgtta actcaggggt tcttaacttg    4740
gggtccatca ccccagggg tccatagttg gacttcagag gtctatgaa accctaaaa      4800 ctgtcagtat ttaatgtatt tattcttgta tgtttttcc agagcattaa agctttcata    4860
aggttctcaa aggtctcaga cctacaaaga gttaaaacaa acagacaaac aaaaaaaaac   4920
actactattt taaatagtgg aactttcagc ccagcgtttc tgcaatgcag agtgaagtgg    4980
atactgggca gttcgagaca ggtttttaat cataagtggt cttttcaaat gtccatcaat   5040
tgatggggaa ggctggcacc caccaagaag tggaagtcct cagaaattct cggcacaccc   5100
tagagtattg tacaaccaac accccacat aactttgtcc cctcttcccc aacaacccag    5160
agcaggtgtt gcagacagga gggccacagc gtgtggaagt aaagactttg gagctagaga   5220
tgccttttcc agcaatgatt attgacttca ccacacccct tgcctggcct ggcctgaggc   5280
tcagcagtgc atgacttctc gtagataact tcacagtcat ccagtcccaa cacctgctct   5340
tgcctggtag gaacaggcga agtgtcagcc ctcaatgttg ggtacttaga cccaaaccaa   5400
taaatggtga gttttgaaca agaactacca tcatgcaggc ttcttgccca gctgaccact   5460
ggccccgggg tgcctgcctg gctggtcttc atccctgag gccaccaggc tcaagccact    5520
gctgttgcat tacacccatc cctttgcaaa atccctatgg agcctgtcac cactcccctc   5580
cctatatacc cccaccccac aaagattttc ttcaggttaa aaaaaagtt taaaaaaaag    5640 atttaaaat aaagcattta tgaaggctta ataaattgta aataattttt aaataaaatg    5700
aaaatgcctt tcctggaaaa aaaaaaaaa aaaaaaaaa aaaaaa                    5747
```

<210> SEQ ID NO 2
<211> LENGTH: 4058
<212> TYPE: DNA
<213> ORGANISM: Homo sapiens

<400> SEQUENCE: 2

```
tgagcactgg ccgcggacgc tccgttgcag tctcgcccag gggccggtac ctgcgctcgc     60
gccgccgggt tgaaaggatg aagccgcagc tggagcagcc accctatgat tggctgtggc    120
gcttgtgaac ccaaagtaaa gatggcgggg gggcaggcag ccgccgcact gcccacttgg    180
aagatggcgg cgcgccgcag cctcagcgct cgcggccggg ggatcctgca ggcggctgcg    240
gggcggctgc tgccgctgct cctgctgagc tgctgctgcg gtgcgggcgg ctgcgcagcg    300
gtgggcgaga atgaggagac ggtgatcatc gggctgcgac tggaggacac gaacgacgtg    360
```

```
tcgttcatgg aagggggggc gctgcgggtg agcgaacgga cccgggtcaa gctgcgggtg     420
tacgggcaga acatcaataa cgagacgtgg tcccgcatcg ccttcaccga gcacgagcgg     480
cggcgccaca gcccggggga gcgcgggctg ggggccccg cgccgccaga gccggacagc      540
ggcccccagc gatgcggcat ccgcacctca gacatcatca tcttgcccca catcattctc     600
aaccgccgca cctcgggcat catcgagatc gagatcaaac cgctacgcaa gatggagaag     660
agcaagtcct attacctgtg cacgtcgctc tccacgcccg ccctgggcgc cggcggctcg     720
gggtccacgg gtggcgccgt cggggggcaag ggtggctcgg gggtggccgg gctcccgccg    780
ccccccgtgg gccgagaccac ctggatttac cacgacggcg aggacaccaa gatgatcgta    840
ggcgaagaga agaagttcct gctgcccttc tggctgcagg tgatcttcat ttcgctgctg     900
ctgtgcctgt cggcatgtt cagcggcctc aacctgggc tcatgccct ggacccgatg        960 gagctgcgca tcgtgcagaa ctgcggcacg gagaaggaga agaattacgc caagcgcatc     1020
gagccggtgc gcaggcaggg caactacctg ctgtgctcac tgctgctggg caacgtgctg     1080
gtcaacacca cgctcaccat cctgctcgac gacatcgccg gctcgggcct cgtggccgtg    1140
gtagtctcca ccatcggtat cgtcatcttc ggagagatcg tgcccaggc catctgctcc     1200 cggcatggcc tggctgtggg ggccaacacc atcttcctca ccaagttttt catgatgatg    1260
accttccccg cttcctaccc ggtcagcaag ctgctggact cgtcctggg ccaggagata     1320 ggcaccgtct ataaccggga aaaactgctg gagatgctcc gggtcaccga tccctacaac    1380
gacctcgtta aggaggagct gaacatcatc aaggggcgc tggagctccg caccaagacg     1440
gtggaggacg tgatgacccc actccgggac tgcttcatga tcaccggcga agccatcctg    1500
gacttcaaca ccatgtctga gatcatggag agcggctaca cccgcattcc agtgtttgaa     1560
ggggagcgct ccaatatcgt ggacctgctg tttgtcaaag acttggcctt cgtggatccc    1620
gatgactgta ccccctgaa aaccatcacc aaattttata accacccctt gcactttgtt     1680
ttcaatgaca ccaagttgga cgctatgctg aagaatttta agaaaggtaa atctcacctg    1740
gctatcgtgc agcgggtaaa caatgaggga gaaggggatc cattttatga agttctggga    1800
atcgtcacct agaagatgt gattgaagaa atcatcaaat ctgagattct tgatgaaaca    1860
gatttataca ctgacaacag aacgaaaaag aaagtggctc accgggaacg aaagcaagat    1920 tttctgcct ttaagcagac agacagtgag atgaaggtta aaatatcacc acagctcctc    1980
ctggccatgc accgtttcct agcaacagaa gtagaagcat ttagcccatc ccagatgtca    2040
gagaagatcc ttctaaggct gctaaagcac cccaatgtca tccaggaact gaaatatgat    2100
gagaagaaca agaagccccc cgaatactac ctctaccagc gcaacaagcc agtagactac    2160
ttcgttctca ttctgcaggg gaaagtggaa gttgaagctg ggaagaagg tatgaagttt    2220 gaagcgagcg ccttctcata ctatggcgtg atggccctga cagcctctcc agttcctttg    2280
tccctgtctc gtacctttgt tgtcagcaga acagagttgt tagcagcagg ttctccaggt    2340
gaaaataagt cccctcctcg cccatgtggc ttgaatcact cagactctct cagtcgaagc    2400
gaccggattg acgccgtcac accaacactg gggagcagca ataaccagct caattcttcg    2460
ctcctccaag tctacatccc cgattactcg gtgcgagccc tttcggatct gcagtttgtt    2520
aagatctcaa gacagcaata ccaaaatgcc ttgatggcat cccggatgga caaaccccc    2580 cagtcttcag acagtgaaaa cactaaaatc gaattgactc ttacggagct gcatgacggg    2640
ttgccagacg agacagccaa cctgctcaac gaacagaact gtgtgacgca cagtaaggcc    2700
aaccacagcc tgcacaacga aggcgccatc taggccgcgc tggctgcacc cgcccaggcc    2760
```

```
cgcacccgcc cagtcccgag ggcccggccc tgtctgccca tgacttcact ggtgtgagct      2820
tgtccgccat gctgtaccct gcaacatcct gagaccaaag accttgtgcc cttcccagga      2880
gccgcggagg aggacagtga gggaggaatg gaaacgagag atgtgaagtt ggcagccggg      2940
gcatggcgtt caagattttg gagatgaact tgattccgcc caaatagaat catgtttatt      3000
ttttcagctc tccctttat cattattcac actcctctgc cctcgatttg catgaagttg       3060
aaaattgttg cgatttattt tttcaagaga tcatgttttt aaagtgtctt ttgcagagtt      3120
ttaagttgtt ctgtctgaac tctgctgtga tcccatgatg tgaccctgat gggctggact      3180 tgccctccg gtagccttcc ttggccctcc cagcgagggg cacccttcct ctgtgcccca       3240
gtgggcatca ccgtcgatct cgctggctga atgaagaaga ccgtgttact gcagaacctg      3300
ccaagtctgt catcactgtg gggtgtagcc tgcctcagag ggacctgcaa tcacctctct      3360
gagctcagtg gtattttgag aatttaatgt ttaactgtac ccctttccct caggaagatt      3420
taacatttgc ttgggaatgt gattttgctc ccaccctaag gaatttttat caccaaaatg      3480
aatgttaatg aatttaaaac ccatggttta tcattggcaa gaggcaagtt gacttcatcc      3540
tgtcattcca gcctggggtc tgccagccag ccctcctccc cgacccagcg cctaagctca      3600
cagagtgtcg tcgcccacct ccctgggtcc ttgctcttgt taacccaaga tgctgctaca      3660
cagatgccaa atgggaaatc ttccacaggg cttttcagt aaacacgtga tgtggagtgc       3720
aagctcctcc ccttcccact agaacatact ttaacagaaa acgagtcgga ccttctagct      3780
gcactctgta ctgtgtgccg agaaggcatt tctagacccg tgttttttaaa ggagggaact    3840 ttggggattg ccagcccctg ctcctcctcc cagggagcca actgtccctc ctcccctgtc      3900
cctgggccca tggggcccgg cagtggctgt gtccctgcc tgagggctct gtgcctcctg       3960
cctcagatgc ggcctgtgcc agagaggctg cctgtacagc cagggtcagt ttggccccaa      4020
acagggattc agaaaccaaa aaaaaaaaaa aaaaaaaa                              4058

<210> SEQ ID NO 3
<211> LENGTH: 3183
<212> TYPE: DNA
<213> ORGANISM: Homo sapiens

<400> SEQUENCE: 3
taacgattgg cccggggagg cgcggggcga gcggggtagg ctgcgcgaga ggccgagagg        60
gggcagcagg cgatggcggc ggcggtagct gcggcgggtc ggttaggctg gttgttcgcc       120
gcgctctgcc tgggcaacgc cgcggggag gccgcgccgg gcccgcgagt gctgggcttc       180
tgcctggagg aggatggagc ggcgggcgcg ggttgggtac gcggaggggc ggcgcgggac       240
acgccggacg ccaccttcct cctgcgcctc ttcggcccgg gcttcgccaa cagctcttgg       300
tcctgggtgg ccccggaggg ggcgggctgc cgggaggagg cggcctcccc cgcgggcgag       360
tggcgcgcgc tgctgcgctt gcgcctgcgg gccgaggccg tgcgcccgca ctcggcgctg       420
ctggcggtgc gcgtggagcc gggtggcggg cggctgaggag aggcggcgcc gccctggtct      480
ctgggcctgg gggcggccgg gctgctggcg ctggcagcgc tggcgcgagg cctgcagctg      540
agcgcgctgg cgctggcgcc tgccgaggtg caggtgctgc gcgagagcgg ctcggaggcg      600
gagcgtgcgg cggcgcggcg tttggagccc gcgcggcgct gggccggctg cgccttgggc      660
gcgctgctgc tgctggccat cctgcgcat gcggcgctgg cggtgctgct gtaccgcgcg       720
gccggccagc gtgcggtgcc cgccgtgttg ggcagcgcgg ggctcgtgtt cctggtggga      780
```

```
gaggtggtgc cggccgccgt gagcgggcgc tggacgctgg cgctggcgcc gcgagcgctc      840
ggcctcagcc gcctggccgt cctgctcact ctgcccgtcg cgctgccgt ggggcagctg      900 ctggagctgg cggcgcggcc cgggcggctg cgggagcggg tgctggagct ggcgcgcggc      960
ggcggcgacc cctacagcga tctcagcaag ggcgtgctgc gctgccggac cgtggaggac     1020
gtgctcacgc cctcgaaga ctgcttcatg ctggacgcca gcaccgtgct ggacttcggc     1080
gtcctggcca gcatcatgca gagcggccac acgcgcatcc cggtgtacga ggaggagcgc     1140
tccaacatcg tggacatgct ctacctcaag gacttggcct tcgtggatcc cgaagactgc     1200
acgccgctca gcaccatcac tcgtttctac aaccatccgc tccacttcgt cttcaacgac     1260
accaagctgg acgctgtcct ggaggaattc aagcgaggga gtcccacct ggccatcgtg     1320 cagaaggtga caacgagggg tgaaggcgac cccttctacg aggtcctggg cctggtcacc     1380
ctggaggacg tgatcgagga gatcatcagg tccgagatcc tggacgagtc tgaagactac     1440
cgagacaccg tggtgaagag gaagcctgct ctctgatgg cccctctgaa gcggaaggag     1500
gagttctcct tgttcaaggt gtctgatgat gaatataag taacaatctc gcctcagctg     1560
ctcttggcca cccagcgctt cctgtcccga gaagtggatg tattcagccc gctgcgcatc     1620
tctgagaagg tcctgctgca cctgttgaag catcccagtg tcaaccagga agtgaggttt     1680
gacgagagca accggctggc cacacaccac tacctgtacc agcgcagcca gccggtggat     1740
tacttcattc tcatcctgca gggcagggtt gaagtggaga tcgggaaaga gggtctgaag     1800
tttgagaatg gggccttcac gtactatgga gtgtcggccc taactgtgcc atcctcggtt     1860
caccagtccc cggtgtcctc gctccagccc atccgccatg acctgcagcc cgacccaggt     1920
gacggcacgc attcatctgc gtattgtccc gactacaccg tgagggcgct ctctgatctg     1980
cagctcatca aggttacgcg actgcagtac ctcaatgcac tcctggctac ccgagcccag     2040
aacctgccac agtcccctga gaacaccgac ctgcaggtta ttccaggcag ccagaccagg     2100
ctccttggtg agaagaccac cacagcggca gggtccagcc acagcaggcc cggcgtcccg     2160
gtggaaggca gccctgggcg gaacccaggc gtttaacggc tcactaggca gccccagatc     2220
tggggaacag atgagcacgt ggggagctgg agtgagctga gcagaagttt tgtgcccgcc     2280
tgcccccatc ccctccaggc cacgttttag atggcccttg tagttgcggg tcctgggtgt     2340
cctcagaact agacatcaat gcctggatcc ttcagccggc cctgccctcc tttaggagac     2400
aggagtcacc agggcacagc cctccaggcc cgcctcagga aggaatgaaa ggaatgccat     2460
catctctagt tcccagggcc cagccttccc cttctccccc ggggcaggga cagtgcggca     2520
tattcagatt cagacctctt tgggctgagc caccttgtga gtgcagttac tgcctttgtg     2580
tggccgtgac ctctatttgt ttgcttttaa tttgccaacc tatcgctgct ggcagcactt     2640
tttgagcaag ccgagagcac ccattttggc tggggttca gatcgatggc cttgtccatg     2700
ttgtcctttc tggcttccct gatggtgtca tgtttcagcg catgcgcccc agcctttccc     2760
atgtgccaaa ccagaagctc cactgcccgt aggctgtccc tgtagccctg ctccctccct     2820
ggaggctgct cttctgattc tgagagctgg cctagtggtg ctgagggccc ctttctgctt     2880
ctctgcccac ctgctgagtt gccactcgca gtgttgtcag ttcccgtgtt ctgagaagag     2940
gtcatgcctg ggaggaaggg atcgtcatgc tgcatcgaat cctctctccg ccgtgtggcc     3000
cccaggagag tagctgcctg ttgcacctgc tccacacctc cccacagcct cctgcaggt     3060 gctgtgtggc cgtgatgtgc agagagcagt gaggagggt tcatgaacca ggtggatcct     3120
cttttaaaaa aaaaagtttt tgttatatc tctaaaaaaa aaaaaaaaa aaaaaaaaa      3180
```

| | |
|---|---:|
| aaa | 3183 |

<210> SEQ ID NO 4
<211> LENGTH: 4765
<212> TYPE: DNA
<213> ORGANISM: Homo sapiens

<400> SEQUENCE: 4

| | |
|---|---:|
| ggtgcggacc ggggccgcgc ggcgtggcgc ggggagcggc ggcggcggca gagccagagc | 60 |
| aacatggcgc cggtgggcgg gggcgggcgc ccggtcggcg gaccggcccg cgggcgcctc | 120 |
| ctcctggcgg cgccggtgct gctggtgctg ctgtgggcgc tgggggcccg gggccagggc | 180 |
| agccccagc agggcacgat cgtgggcatg aggctggcga gctgcaacaa gtcgtgtggg | 240 |
| acgaacccgg atggcatcat cttcgtgtcc gagggcagca ccgtgaacct gaggctgtac | 300 |
| ggctacagcc tggcaacat ctccagcaat ctgatctcct tcaccgaggt ggacgatgcc | 360 |
| gagaccctcc acaagtccac cagctgcctc gagctcacca aggacctggt cgtccagcag | 420 |
| ctggtcaacg tgagccgcgg gaacacgtcc ggcgtgctgg tggtgctcac caagttcctc | 480 |
| cggaggagcg agagcatgaa gctgtatgca ctgtgcaccc gggcccagcc cgacgggccc | 540 |
| tggctgaagt ggacggacaa ggactcactg ctcttcatgg tggaggagcc tgggaggttc | 600 |
| ctgcctctct ggctgcacat tctcctaatt acggtgctgc tggtgctgtc gggcatattt | 660 |
| tctggcctca acctcgggct tatgcccctg accccatgg agctgcgcat cgtgcagaac | 720 |
| tgtggcaccg agaaggagag cgctatgcc cgcaagattg agcccatccg cgcaagggc | 780 |
| aactaccttc tctgctcgtt gctcctaggg aacgtgctgg tcaacacctc cctcacaatc | 840 |
| cttctagaca acctcatcgg gtccggcctc atggcggtgg cctcctccac cattggcatt | 900 |
| gtcatctttg gggagatcct acctcaggcc ctgtgctccc gacatgggct ggctgtgggt | 960 |
| gccaacatca tccttctcac caaattcttt atgctactca ccttccccct cagttttccc | 1020 |
| attagcaagc tcctggactt ttttctgggc caggagattc gcactgttta caaccgggag | 1080 |
| aagctgatgg agatgttgaa ggtgacggag ccctataatg acctcgtgaa agaggagctc | 1140 |
| aatatgatcc agggtgccct ggaactacgg accaaaactg tagaggatat catgacccag | 1200 |
| ctccaggact gcttcatgat ccgcagcgat gccatcctgg acttcaacac catgtcggag | 1260 |
| ataatggaaa gcggctatac tcgcatcccg gtgttcgaag acgagcagtc caatattgta | 1320 |
| gatattctct acgtcaaaga cttggccttt gtggaccccg atgactgcac ccccctcaag | 1380 |
| actatcactc gcttctataa ccacccggtg cactttgtct tccatgacac caagttggat | 1440 |
| gccatgctgg aggagttcaa gaggggaag tcccacctgg ccatcgtgca gaaggtaaac | 1500 |
| aacgagggtg aggtgacccc cttctacgag gtcctgggcc tggtcaccct ggaggacgtg | 1560 |
| atcgaggaga tcatcaagtc ggagatcctg acgagtccg acatgtacac tgacaaccga | 1620 |
| agccggaagc gggtgtctga agaacaag cgtgacttct ctgccttcaa ggatgcggac | 1680 |
| aatgagctca agtgaaaat ctccccgcag ctcctcctgg ccgctcatcg cttcctagcc | 1740 |
| acagaggtct ctcagtttag cccctccctg atatcagaga agatcctgct gcggctactc | 1800 |
| aagtacccag atgtcattca ggaactcaag tttgacgagc acaataagta ctacgcccgc | 1860 |
| cattacctgt acacccgaaa taagccggcc gactacttca tcctcatcct gcaggggaag | 1920 |
| gtggaggtgg aggcagggaa ggagaacatg aagtttgaga cgggcgcctt ctcctactat | 1980 |
| gggactatgg ccctgacctc ggtccctcc gaccgttccc cagcacaccc caccccactc | 2040 |

-continued

```
agccgctcag cctccctcag ttacccagac cgcacagacg tctcaactgc agcaaccttg    2100
gcaggcagca gcaaccagtt tggcagctct gtcctgggcc agtacatctc tgacttcagc    2160
gtccgggcac tcgtggactt gcagtacatc aagatcactc ggcagcagta ccagaacggg    2220
ctgctggctt ctcgcatgga aacagccct cagtttccca tagacgggtg caccacccac     2280
atggagaact tggccgagaa gtctgagctg cctgtggtgg acgagaccac aactcttctc    2340
aacgagcgta actccttgct gcacaaagcc tcccacgaga atgccatctg acaggagggc    2400
ccggggcccc ctgcccaccc tgcggggggcc tccccagtgg gcccacatga agagagggaa   2460
cctgttagtc cagaaaggat acggatagat agcctgtctg actgaacagc cagatggccc    2520
ccagcctatg gggatctgg cctctgccag ggacctctga gtagctctga ggtggcactg     2580
tccagccctg datagggggg gcagtgggcc agctaccgta agcaaaggct gtttttttact   2640 gagagaattt ctaaagtagg ctcatcactt ttttttaaat atcatttttgg gaagggaaga   2700 cagggttaag gaactttatt taaaaaaaaa atatttttttt cctaaaaact ataaaagagg   2760
aagggtttct tgtcccggga agcaacggac ataatctgtt cccagccatg gccttccagc    2820
ttgtgtccct gattcaggga gctctccctt cctcctcctc ctcctcctcc ggaggtggga    2880
tcccagagcc tgccagtgga ggcttatctg ttgggaggaa gacagctctt cacagaagca    2940
aagaacaaaa tggcatggag atcagctgcc tgagcacctg cgctgtagct tatctgacaa    3000
cgctgaggcc acgagctcct gggtagctgt gatcagggac atgataatct gagctatgca    3060
gaggagcaca tctgttgtca actgctgtac ccagaaatct agaactctgc cgacagcctc    3120
tcctggtgag tcgggactca gctgaggaca catccccacc ctgcctccca tctggccctt    3180
tggacaactg gccctttgtg acagggctga ctcaagtgtt aggcagggtc tcaggccttt    3240
gattgctcac ccctgctccc caggccctgc cctcactttt accaaaggtt ctccctcggc    3300
gggagggcat ctgtgttgga ggtgatttgt ctgggttctt ccttttggtt ccagaaggaa    3360
ctgtcagtca tcagcatctg cgttgttagc agtcagtacc accccgcccc cacaatgaca    3420
gtcaaggctg acttgttgac tgaagccttt ttcccagacc ccttatttcg aatcccccaag   3480 cttcagtccc tcttgggggt ggagacaaga ggacatgtgg gaagccacgg aagcaggttc    3540
tttatgtcct ctcctctgtg gctggcaagg ctcacctggc cttatccacc cacttatgga    3600
acctcaggag aggagggctc ctcctaaagg catgcagctt gcagcccctc tttctcacac    3660
gtgtgatcct agcgtgagag gtcatcctgc ccttgctgaa gttagtagta ctgtactaag    3720
agctctgccc tcatgtgaat tcctgccctg gtgcctcttc cctggggctg aatcaggccc    3780
tgctgcaaaa ctccaggctt ccagggttg gggaggctgt gggaccaagg tccatgttgg     3840
tccttccact gggtgcagca ggagctgggt cccgagagcc tggcaggtga aactctgcag    3900
gccttccgcc tgattattat ttattcactc cttttcctcac cccaagtgcc ctgctctcca   3960
ggtgcctaga gtatcctaac tcttaggacc agggattgtc ttgcaccaag tatgcctacc    4020
cctggccagt ctgaggtctc ctagccatag aactgactcc tggaagcctg gagagaaggt    4080
ggtgacaccc atgggttctc aactgtaagg aaaaaagaca ccagactttt gttccctagt    4140
gggggaaagc ccttagtctt gtacaggagc agcttgctcc caagtccttt tggaagctgg    4200
cagagctata ttcctgacag ccctgactgc caggtagagc aaaagacatt ggtgggggta    4260
tgtgaagcaa aaggggcagg tgcacacacc tccacagtga cctctgtgca cacggttacc    4320
accaactggc tggccctcct cctcttccct ggcccattga tcatcccttc tcacagaggg    4380
tcatcattat ttccaaatat tgtttgtctg atgacttcct cttcccagtg caatttttcc    4440
```

-continued

| | |
|---|---|
| cttcctattt caacctctgg ttcctgggat gagccatacc ctggaactgg cccacccact | 4500 |
| gtgtcttcca cgtaagggag acctttgcaa agggcatcca aatgggtagg caggtgacag | 4560 |
| ccgccgtatt tattttgcat aatatttaa tttgtatatt tttgtgattt attttggcgt | 4620 |
| tatgagtttg actctcgggg agttttgttg ttatgactct tgtgtctttt gtcacaaaac | 4680 |
| aatgatattt gctaaacgat atatggaatt tattttgat tggtaataaa aaatcaaata | 4740 |
| tgtataaaaa aaaaaaaaaa aaaaa | 4765 |

<210> SEQ ID NO 5
<211> LENGTH: 3631
<212> TYPE: DNA
<213> ORGANISM: Mus musculus

<400> SEQUENCE: 5

| | |
|---|---|
| tcgcgctcgg cttgctgcag tatcacgtgc aaccgcgccg ggtgcaggat ggcggcggcg | 60 |
| gccgcggcgg cagcagcgct gggtgtcagg ctccgggact gctgcagccg gggcgccgta | 120 |
| ctcctgctct tcttctccct gtcccctcgg cccccggccg ccgctgcctg gttactgggt | 180 |
| ctgcgacccg aagacactgc cggagcccgc gtgtctctgg aggggggcac cctgcgggcg | 240 |
| gccgaaggca ccagcttcct cctgcgggtc tacttccagc ctggcccgcc ggtccccgcc | 300 |
| gcgcccgtgc ccgcacccctc cctggccccg ggggaaaacg gcacgggcga ttgggccccg | 360 |
| cggctcgtgt tcatcgagga gccccggggc gctggcggcg cggcgccag cgcggtcccc | 420 |
| acgcgtcccc cggaccctca gcgctgccgc gagcagagcg actgggcgtc ggacgtggag | 480 |
| gtcctggggc cctgcgcccc cggggcgtg gcgggctcgg ccctggtcca ggtgcgggtg | 540 |
| cgggagctgc ggaagggcga ggcggagcgc ggcggcgcgg gcggcggcgg aaagctcttt | 600 |
| tcgctgtgcg cctgggacgg gcgcgcttgg caccaccacg gcgccgccgg cggcttcctg | 660 |
| ctgcgcgtcc gcccgcgcct ctacggcccg ggtgggggacc tgctgccgcc cgcgtggctg | 720 |
| cgagcgctcg gggcgctcct gctgctggcc ctgtccgccc tgttcagcgg cctgcgcctg | 780 |
| agcctgctct cgctggaccc ggtggagtta cgggtgctgc ggaacagtgg ctcggccgcc | 840 |
| gagcaggagc aggcgcgccg cgtgcaggcc gtgcgcggca gggggaccca tctgctctgc | 900 |
| accctgctcc tggccaagc cggagccaat ccgcgctgg ccggctggct gtacgcctcg | 960 |
| ctgccgccgg gcgtcgggga ccccggggag gactccggcg aggcgggggt tcacttcccg | 1020 |
| tggctgccgg cgctggtgtg caccggcgcc gtgttcctgg gagccgagat ctgtccgtac | 1080 |
| tcggtgtgct cgcgccacgg gttggccatc gcctcgcaca gtgtgtgcct gacccggctc | 1140 |
| ctcatggcgc ctgccttccc ggtgtgctac cctctgggcc gcctcctgga ctgggctctg | 1200 |
| cgccaggaga tcagcacctt ctacacgagg gaaaagctgc tggagacgct gcgggccgcc | 1260 |
| gacccttaca cgacctggt gaaggaagag ctcaacatca ttcagggagc cctgagctg | 1320 |
| cgcaccaagg tggtagagga ggtgctgacc cctctagggg actgcttcat gttgcgctct | 1380 |
| gacgccgtgc ttgacttcgc cactgtatcc gagatcctcc gtagtggcta cactcgcatc | 1440 |
| ccggtgtatg agggcgacca gaggcacaac attgtggaca ttctgttcgt caaagacttg | 1500 |
| gcctttgtgg acccgacga ctgtaccccg ctgctcacag tcacccgctt ctacaacagg | 1560 |
| cccctgcatt gtgtcttcaa tgatacccgg ctggacactg tactggagga gtttaagaag | 1620 |
| ggaaaatctc acttggccat tgtccagaga gtgaacaacg agggtgaagg agacccttc | 1680 |
| tatgaggtga tgggcattgt gactctggag gacatcatag aagagatcat caagtcggag | 1740 |

| | |
|---|---|
| atcctcgacg aaactgacct ctacactgac aatcggaaaa agcagagggt cccacaccgg | 1800 |
| gagagaaggc ggcatgattt ctctctgttc aagctttcag actccagat cagagtcaag | 1860 |
| atctcgccac agctgctgct tgccacacac cgcttcatgg ccacagaagt ggagcccttt | 1920 |
| aagtccctgt acctttcgga agatcctg ctccggcttc tgaaacatcc caacgtgatc | 1980 |
| caggagctta agtttgatga gaggaacaag aaagccccag aacactacct ctaccagcgc | 2040 |
| aaccgcccgg tggactattt tgtgctgctc ttacagggga agtggaagt ggaggttggt | 2100 |
| aaggaaggcc ttcgctttga aacggagcc tttacctact atggtgttcc agccatcatg | 2160 |
| accagcgctt tctcagataa tgacgtgcgg aaggttggaa gtctggctgg atcctctgtc | 2220 |
| ttcctaaacc ggtccccttc tcgctgcagc gggttgaatc gctccgagtc tccaaaccga | 2280 |
| gagcgcagtg acttcggcgg aagcaacacg caactgtaca gcagcagcaa caacctctac | 2340 |
| acacctgact actcggtgca cattctcagt gatgtgcagt tcgtgaagat cacacgacaa | 2400 |
| cagtaccaga acgcactcac ggcctgccac atggacagct caccccagtc cccggatatg | 2460 |
| gaagccttca ctgatgggga ctccaccaag gcccccacca ccggggcac accccagact | 2520 |
| ccaaaggacg acccggtcct caccctcctg agcaacagga ccagcttgcc atgcagccgc | 2580 |
| tcggatggtc tgagaagccc aggcgaggtt gtgtacctga ggatggagga gatggccttc | 2640 |
| ccccaagaag agatgcccaa ctttgaggag cacaggtcac agcaagtctc gctgtcccct | 2700 |
| gtcgcagttc ctacaacagc agcttcggat cctgaatgct gtaatatcca cctggatcca | 2760 |
| gaggccagcc cctgcagcag cgactctgag gaaaacatgg gcaagaagct gctgagaacc | 2820 |
| ttgagtggcc ggaaaagaaa gaagtccgca gacggggagc gagcctccga ggaaaactcc | 2880 |
| aatttaacgc ccctgatcac atgaccaggt cttccctcat ggctgagtg tgagactctg | 2940 |
| aggctttggg ggaagaccca ccctcccgtc actcgccacc cccaaggcct cccatcagtg | 3000 |
| acagaacatt cggcccttca cccttcaccc ctcagtcagt ctggcacgtt ttatcagttg | 3060 |
| cctccagtct gacacagaag gagacgcctg taatggaaga cgctagaaat ggttttgtct | 3120 |
| gtagcatagt ctaagaactg gccagggccg acgcaaagct gagaatgcca ttctgaggct | 3180 |
| cccaataata atctttgttc tttggtgtcc ctgggccaca ggagacccat gtcctggaat | 3240 |
| tcaccattct ttcttccagg acaaaataat gctttctacc atagttcatg cttagcattc | 3300 |
| gctcagacag tgatgcgggc agagaggtgt actggagtct agaggagccg gtgtgaaaat | 3360 |
| cagctccagg gatggacaga tggacaagga ttgttccctg ttagtgtgtg gattctcccc | 3420 |
| acagcctggg gaagggcagt tcggctgcag tgaagaaaga gagggaagc cctgagtccc | 3480 |
| tgtatctccc agagacgtca gtttgggctt cccgagtcta taagcttgct tcagaagagg | 3540 |
| aggttcaggg gacacagaga ccaagttgtg agccagatac agaacttcag gttttaagtg | 3600 |
| aaaataaaag caggaaaaaa aaaaaaaaa a | 3631 |

<210> SEQ ID NO 6
<211> LENGTH: 3204
<212> TYPE: DNA
<213> ORGANISM: Mus musculus

<400> SEQUENCE: 6

| | |
|---|---|
| agcagccacc ctatgattgg ctgtggcgct tgtgaacccg aagtaaagat ggcgggcggg | 60 |
| caggcagccg ccgcactgcc cacttggaag atggcggcgc gccgcagcct cagtgcccgc | 120 |
| ggccgggggg tcctgcaagc agctgcgggc cggctgctgc cgctgctact gctgagctgc | 180 |
| tgctggggag cgggcggctg cacagcgggc ggcgagaccg aggagaccgt gatcatcggg | 240 |

-continued

```
ctgcggctgg aggatacgaa cgacgtgtcg ttcatggaag ggggtgctct gcgggtgagc      300
gaacggaccc gggtcaagct gcgggtgtac gggcagaaca tcaacaacga cgtggtcc        360 cgcatcgcct tcactgagca cgagcggcgc cggcacacac ccggcgagcg tgggctgggg      420
ggccccgcgc ctccggagcc ggacagcggc cccagcgct gcggcatccg caccctcagac     480 atcatcatct tgccccacat cattctcaat cgccgcacat cgggcatcat cgagatcgag      540
attaaaccgc tgcgcaagat ggagaagagc aagtcttatt acctgtgcac gtctctctcc      600
acgcccgcac taggcgccgg cggctccggg tctgcgagtg gcaccgtcgg gggcaagggt      660
ggcgcggggg tggccggact cccgcctcct ccgtgggccg agaccacctg gatttaccac      720
gacggtgagg acaccaagat gatagtgggc gaggagaaga agttcttgct gcccttctgg      780
ctgcaagtga tcttcatctc gctgctgctg tgcctgtcgg gcatgttcag cggcctcaac      840
ctggggctca tggctctgga cccgatggag ctgcgcatcg tgcaaaactg cggcacggag      900
aaagagaaga attatgccaa gcgcatcgag ccggtgcgca ggcagggcaa ctacctgctg      960
tgctcgctgc tgctgggcaa cgtactggtc aacaccacgc tcaccatcct gctggacgac     1020
attgcgggct caggccttgt ggcggtggtg gtctccacca ttggcatcgt catcttcgga     1080
gaaatcgtgc cccaagccat ctgctcccga cacggcctgg cggtaggggc caacaccatc     1140
ttcctcacca gttttttcat gatgatgaca ttccccgctt cttatccggt tagcaaactg     1200
ctggactgcg tcctgggcca ggagataggc acggtctata accgggaaaa actgctggag     1260
atgctccggg ttactgaccc ctataacgac ctcgttaagg aagagctgaa catcatccaa     1320
ggggcgctgg agctccgcac caagacggtg gaggacgtga tgactcccct cagggactgc     1380
ttcatgataa ccggcgaggc tatcctggac ttcaacacca tgtcggagat catggagagt     1440
ggctacactc gaatcccggt gttcgaggga gaacgttcca acatcgtgga cctgctcttt     1500
gtcaaagact tggccttcgt ggatccggat gactgtactc ccttgaaaac catcaccaag     1560
ttttacaatc acccttttgca cttcgttttc aacgacacca agttggacgc tatgctggaa     1620
gaatttaaga aagggaaatc ccacctggcc attgtgcagc gagtgaacaa tgagggtgaa     1680
ggggacccat tttatgaagt tctgggaatt gtcaccttgg aagatgtgat tgaagaaatc     1740
atcaaatctg aaatcttgat gagacagacc tgtacaccga taacagaaca aaaaagaaag     1800
tggcccaccg tgaaagaaag caagatttct ctgcctttaa gcagacggac agcgagatga     1860
aggttaaaat atcaccgcag cttctcctgg ccatgcaccg tttcctagca acagaagtag     1920
aagcgtttag cccatcccag atgtcagaga agatcctcct aaggctgcta aagcaccca     1980 atgtcatcca ggagctgaag tacgacgaga gaaacaagaa agcccctgag tgctacctct     2040
accagcggaa caagcccgta gactacttcg tcctcattct tcaggggaag gtggaggtgg     2100
aagctgggaa agaaggcatg aagtttgaag ccagcgcttt ctcctactat ggtgtgatgg     2160
ccctcacagc ctctccagtt cctttgtccc tgtctcgcac ctttgttgtc agcaggacag     2220
aggtgttagc tgcgggctct ccaggggaaa ataagtcacc tcctcgcccc tgtggcctga     2280
atcactcaga ttctctcagt cggagcgacc ggattgacgc catgacgcca accttgggga     2340
gcagcaacaa ccagctcagc tcttccttcc ttcaagtcta catccctgac tactcagtac     2400
gagccctctc tgacctacag ttcgtcaaga tctccagaca gcaataccaa aatgccttga     2460
tggcgtctcg gatggacaaa acgcctcagt cttcagacag tgaaaatact aaaattgaat     2520
tgactcttac ggagctgcat gacggcttgc cagatgagac ggccaacttg ctcaatgaac     2580
```

| | |
|---|---:|
| agaactgtgt gtcacacaac aaggccaacc acagcctgca cagtgaaggc gccatctagg | 2640 |
| gcccctcggg cccccttgtc cggccctcct ggacttggtc tgaccatgac ttccgctagt | 2700 |
| tgagcttgtc tgccatgctg cgtcctacag ccttgagacc aaagactttg cccctttccc | 2760 |
| tggaagccgc ggaggacggc tgggggaggg atggaaactg gacacgtgac atccacagct | 2820 |
| ggggcatggc tttcaagaat tcggagacaa acttcttcca cccaaataga atcatgttta | 2880 |
| ttttttcaga acctttatc gtttctttca tccctcaatt tgcatgaaat ttaaaaattg | 2940 |
| tttcattatg ttttttcca agagatcatg tttttgtttc taagtgtctt ttgcagagtt | 3000 |
| tgaagttggt ctttccaagc taactctgct gtagccccac cgtgtgaccc cgacaggatg | 3060 |
| gacttgcccc tttaacggcc ttccctggcc gtccccagga gggatacctt tcctctgtgc | 3120 |
| ccggtgggtg tcgctgtcga acttgatgga tgaatgaaga aaaatcatgt ccctgcaaaa | 3180 |
| aaaaaaaaaa aaaaaaaaaa aaaa | 3204 |

<210> SEQ ID NO 7
<211> LENGTH: 2684
<212> TYPE: DNA
<213> ORGANISM: Mus musculus

<400> SEQUENCE: 7

| | |
|---|---:|
| attggctgca acaacagagg cgcgggtgag tggggtaggc tgcgcccgag gcccagaagg | 60 |
| ggtagcaggc catggcggcg gctgctgcgg ctgtggtggg ttggttgggc tgggtgcttg | 120 |
| ccgcgttctg tctgggcagc accgcagggg aggcggcgcc ggcgccgggc gcggactgc | 180 |
| tgaacttctg cacggaagag gacagcgcac cgggcgcggg ctccctgcgc ggaagggcag | 240 |
| cgccagaggc cactttgtgc ttgcgactct tctgctccgg cttggccaac agctcctgga | 300 |
| cctgggtagc cgccgagggc gcaggctgcc cggagggcgg acgggccacg gagcccgagg | 360 |
| aggcggccgc cccgacgggc gagtggcgcg cgctgctgcg cctgcgcgcc gaggccggcc | 420 |
| acccgcgctc cgcgctgctg gcggtgcgcg tggagccggg tggtggggcc gcggaggagg | 480 |
| cggcgccgcc ctgggcgctg gggctggggg cggccgggct gctggccctg gcggcggtgg | 540 |
| cgcgcggcct gcagctgagc gcgctggcgc tggcgccggc cgaggtgcag gtgctgcgcg | 600 |
| agagcggctc ggaggcggag cgcgcggcgg cgcggcgcct ggaacccgcg cggcgctggg | 660 |
| ccggctgcgc cctgggcgcg ctgctgcttc tggccagcct ggcgcaggcg gcactggccg | 720 |
| tgctgctgta cggggcggcg ggccagcgcg ccgtgcccgc cgtgctgggt tgcgcggggc | 780 |
| tggtgttcct ggtgggtgag gtgctgccgg ccgccgtgag cggacgctgg gcgctggcgc | 840 |
| tggcgccgcg cgcgttgggc ctcagccgcc tggcggtgct gctcaccttg cccgtggcgc | 900 |
| tgccggtcgg gcagctgctg gagctggcag cgcggccggg gcgtctgcgg gagcgcgtgc | 960 |
| tggagctggc gcgcggcggc ggcgacccct acagcgacct cagcaaggga gtgctgcgct | 1020 |
| cccgaccgt ggaggacgtg ctcacgccgc tcgaagactg ctttatgctg gactccggca | 1080 |
| ctgtcctaga cttcagcgtc ctcgccagca tcatgcagag cggccacacg cgcatcccag | 1140 |
| tgtacgagga ggagcgctcc aacatcgtgg acatgctcta cctcaaagac ttggctatcg | 1200 |
| ttgagcccga ggactgcaca ccgctcagca ccatcacccg cttctacaac catccactcc | 1260 |
| actttgtctt caacgatacc aaactggacg ctgtcctgga ggagttcaag cgaggcaagt | 1320 |
| cccacctggc cattgtgcag aaggtgaaca atgagggcga gggcgacccc ttctacgagg | 1380 |
| tgctgggcct ggtcacccct gaggacgtca tcgaggagat catcaagtct gagatcttgg | 1440 |
| atgagtctga agactactca gacacaaagg tgaggaagaa gaccgtcgcc ctgggagctc | 1500 |

-continued

| | |
|---|---|
| ctctcaagcg aaaggaggaa ttctcottat tcaaggtgtc tgatgatgaa tataaagtaa | 1560 |
| aaatctcgcc tcagctgctc ctggccaccc agcgcttcct ttcccgagag gtggatgtgt | 1620 |
| tcagcccatt gcgagtctct gagaaagtct tgctgcacct gctgaagcat cccagtgtca | 1680 |
| accaggaggt gacgtttgac gagagcaacc gcctggccgc acaccattat ctgtaccagc | 1740 |
| gcagccagcc agtagattac ttcattctca ttctgcaggg cagagtcgag gtcgaaattg | 1800 |
| ggaaagaggg cctgaagttc gagaacgggg ccttcacgta ctatggagtg tccgccctga | 1860 |
| cagccccatc ctcagctcac cagtccccag tgtcttcacg ccagctcatc cgccatgacg | 1920 |
| tgcagcctga accagccgat ggtacccgct cctgcacata ctgtcctgac tacactgtga | 1980 |
| gggcccttc cgacctgcag ctcattaagg tcacacggct gcagtacctt aatgcactcc | 2040 |
| tggctacccg agcccaaagc ttgcctccat ccccagagaa cgctgagctc caggctatcc | 2100 |
| caggcagcca gaccaggctc cttggtgaca agtccagaga cagcagggg tccaccaaca | 2160 |
| gcagacccag catcccagtg gaggagagcc ctgggcggaa cccaggagtg taactgcttg | 2220 |
| ccggacagcc ccgagctgga aatggacaag cgtttgggga gctgggagag ccgagcagga | 2280 |
| gcttcatgcc agcctgtccc cacctatcct ggccacgttt tagatggccc ttgtaagctg | 2340 |
| tgggtcctga gccgcctcgg tgccagagcc tccagccgtc ctgctgtcct tgaggagatg | 2400 |
| gggttgacaa agcggccctc cagaagcctg tttccgaggg gacaaaagaa acagcgtcat | 2460 |
| ctctagtccc cagctcccag cttccccggt gctgtaacag cacagtgtgt ttatgtgtct | 2520 |
| ccctgagccc agggccatgc gggtacagcc actgccttta catggccctg gcctgtgctc | 2580 |
| attctgcttt tggttggcca accctctgtc agtggcgcca ctttctgagc aagccaagag | 2640 |
| tgctgagttt tgatggaagt gttcaaaaaa aaaaaaaaaa aaaa | 2684 |

<210> SEQ ID NO 8
<211> LENGTH: 2743
<212> TYPE: DNA
<213> ORGANISM: Mus musculus

<400> SEQUENCE: 8

| | |
|---|---|
| aggagcggag gcgccgagtg aggcgcgcgg cggggcgcgg gcagcggcgg ggccggagca | 60 |
| acatggcgcc ggggggcggg ggcggccggc gggacggctg gccggcccga gggcgcctcc | 120 |
| tcctggctgc gctgctgctg ctatggacgc gggcggccag cggccagagc agcccccagc | 180 |
| agagcgtgat cctaggcatg aggctagcga gctgcaacaa gtcgtgcggg atgaacccgg | 240 |
| atggcatcat cttcgtgtcc gagggcagca cggtgaactt gaggctctat ggccacagcc | 300 |
| tgggcgatat ctccagcaac ctgatctcct tcaccgaggt ggacgacgcc gaggcggtcc | 360 |
| acaactccac caactgcctg gagctcacca aggacttagt ggtccagcgg ctggtcaacg | 420 |
| tgagccgcgg gaacacgtcg gggatgctag tggtgattac caagttcctg cggaggagcg | 480 |
| agaacatgaa gctgtacgcg ctgtgcaccc ggccccgggc cgacgggccc tggaccagat | 540 |
| ggacggacaa ggactccctg ctcttcatgg tggaggagca tgggaggttt ctgccgctct | 600 |
| ggctgcacat ccttctcgtt atggtgctgt tggtgctgtc gggcatcttt tctggcctca | 660 |
| acctggggct tatggccctg gacccgatgg agctgcgcat cgtgcagaac tgtgaactg | 720 |
| agaaggagag aaagtatgct cgcaagatag agcccatcag gcgcaagggc aactacctgc | 780 |
| tctgctcgct gctcctgggg aacgtgctag tcaacacctc cctcaccatc cttcagaca | 840 |
| acctcatcgg gtctggcatc atggcagtgg cctcctctac cattggcatt gtcatctttg | 900 |

-continued

```
gggagatctt acctcaagcc ctgtgctccc ggcacgggct ggctgtgggt gccaacacta    960
ttgttctcac caaagtcttt atgctcctca cttttccctt gagtttcccc attagcaaac   1020
tcctggactt cgtcttaggt caggagattc gcactgttta caatcgggag aagctgatgg   1080
agatgttgaa ggtgacagag ccctataatg acttggtgaa ggaggagtta aatatgatcc   1140
agggtgccct ggaactaagg accaaaactg tggaggatat catgacccag ctacacgact   1200
gcttcatgat ccgcagtgat gccattctgg acttcaacac catgtcggag attatggaga   1260
gtggctacac tcgcattcct gtgtttgaag atgagcaatc caatattgta gatatcctgt   1320
atgtcaaaga cttggctttt gttgacccgg atgactcaca cccgctcaag accatcactc   1380
gcttctacaa ccacccggta cattttgttt tcatgacac caagctggat gccatgctag   1440
aggaatttaa gaagggcaag tcccacctgg ccatcgtgca aaggtgaac aatgagggcg   1500
agggcgaccc cttctacgag gtgctgggcc tggtcactct ggaggacgtc atcgaggaga   1560
tcatcaagtc cgagatcctc gatgagtcgg acatgtacac tgataatcgg acccggaaac   1620
gggtgtccgt gaaaaacaag cgtgacttct ctgccttcaa ggacactgac aatgaactca   1680
aagtgaaaat ctcacctcag cttcttctgg ctgctcatcg cttcctggcc acagaggtgc   1740
cccagtttag cccctctctg atgtcagaga agatcctgct ccggctgctc aagtaccccg   1800
acgtcattca ggagctcagg ttcaatgagc acaacaggta ctgcgttcgc cactacctgt   1860
acacccggaa caagccggcc gattgcttcg tcctcatcct gcaggggaag gtggaggtag   1920
aagcaggcaa ggagaacatg aagtttgaga cgggcgcctt ctcgtactat ggaaccatgg   1980
cactctccgt ggcaccccca gaccggtccc cagccctccc aactccactc agccgctcag   2040
cttccctcag ttacccggac cgcaacacag acttgacatc cacctccctg gcaggcagca   2100
accagtttgg cagctgcatt ctgggccagt atgtctctga cttcagtgtg cgggcgctca   2160
cggacctgca gtacattaag atcacaaggc agcagtacca gaatgggctg atggcctccc   2220
gcatggacaa cagcccccag cctaccttcg atggctgtgc cacctgctca gagaacttta   2280
tggagaggcc tgagctgccc ccggtggacg agaccacgac tcttctcaat gaacgcaact   2340
cgttgctgca cagagcctcc gaagaggaaa ccatctgaca ggagggcccg ggactcccg   2400
cccaccctgc gggggtctcc ccagtgggcc cacatgaagt caggagcctg ttaggctaga   2460
aggggtgcag gtagatatcc tgcatgactg agcaaccaga catccctgtc cagggctct   2520
ggctgcagat agggacctct gaacagctct gacatgatgc ctgccctgcc cagctagtga   2580
gcaaaggctg ttgggttgtt gttggttttt tttttttttt tttttttttt taaacactga   2640
gagaagtttt aagctaggct cattgctcct ctttaaaat atcatttggg gaagggaaga   2700
cagggttaag gaactttatg taaaaaaaaa aaaaaaaaa aaa                     2743
```

<210> SEQ ID NO 9
<211> LENGTH: 951
<212> TYPE: PRT
<213> ORGANISM: Homo sapiens

<400> SEQUENCE: 9

```
Met Ala Ala Ala Ala Ala Ala Ala Ala Val Gly Val Arg Leu Arg
1               5                  10                  15

Asp Cys Cys Ser Arg Gly Ala Val Leu Leu Phe Phe Ser Leu Ser
                20                  25                  30

Pro Arg Pro Pro Ala Ala Ala Trp Leu Leu Gly Leu Arg Pro Glu
                35                  40                  45
```

```
Asp Thr Ala Gly Gly Arg Val Ser Leu Glu Gly Gly Thr Leu Arg Ala
 50                  55                  60

Ala Glu Gly Thr Ser Phe Leu Leu Arg Val Tyr Phe Gln Pro Gly Pro
 65                  70                  75                  80

Pro Ala Thr Ala Ala Pro Val Pro Ser Pro Thr Leu Asn Ser Gly Glu
                 85                  90                  95

Asn Gly Thr Gly Asp Trp Ala Pro Arg Leu Val Phe Ile Glu Glu Pro
            100                 105                 110

Pro Gly Gly Gly Val Ala Pro Ser Ala Val Pro Thr Arg Pro Pro
        115                 120                 125

Gly Pro Gln Arg Cys Arg Glu Gln Ser Asp Trp Ala Ser Asp Val Glu
        130                 135                 140

Val Leu Gly Pro Leu Arg Pro Gly Gly Val Ala Gly Ser Ala Leu Val
145                 150                 155                 160

Gln Val Arg Val Arg Glu Leu Arg Lys Gly Glu Ala Glu Arg Gly Gly
                165                 170                 175

Ala Gly Gly Gly Lys Leu Phe Ser Leu Cys Ala Trp Asp Gly Arg
            180                 185                 190

Ala Trp His His His Gly Ala Ala Gly Gly Phe Leu Leu Arg Val Arg
        195                 200                 205

Pro Arg Leu Tyr Gly Pro Gly Gly Asp Leu Leu Pro Pro Ala Trp Leu
        210                 215                 220

Arg Ala Leu Gly Ala Leu Leu Leu Ala Leu Ser Ala Leu Phe Ser
225                 230                 235                 240

Gly Leu Arg Leu Ser Leu Leu Ser Leu Asp Pro Val Glu Leu Arg Val
                245                 250                 255

Leu Arg Asn Ser Gly Ser Ala Ala Glu Gln Glu Gln Ala Arg Arg Val
            260                 265                 270

Gln Ala Val Arg Gly Arg Gly Thr His Leu Leu Cys Thr Leu Leu Leu
        275                 280                 285

Gly Gln Ala Gly Ala Asn Ala Ala Leu Ala Gly Trp Leu Tyr Thr Ser
    290                 295                 300

Leu Pro Pro Gly Phe Gly Gly Thr Gly Glu Asp Tyr Ser Glu Glu Gly
305                 310                 315                 320

Ile His Phe Pro Trp Leu Pro Ala Leu Val Cys Thr Gly Ala Val Phe
                325                 330                 335

Leu Gly Ala Glu Ile Cys Pro Tyr Ser Val Cys Ser Arg His Gly Leu
            340                 345                 350

Ala Ile Ala Ser His Ser Val Cys Leu Thr Arg Leu Leu Met Ala Ala
        355                 360                 365

Ala Phe Pro Val Cys Tyr Pro Leu Gly Arg Leu Leu Asp Trp Ala Leu
        370                 375                 380

Arg Gln Glu Ile Ser Thr Phe Tyr Thr Arg Glu Lys Leu Leu Glu Thr
385                 390                 395                 400

Leu Arg Ala Ala Asp Pro Tyr Ser Asp Leu Val Lys Glu Glu Leu Asn
                405                 410                 415

Ile Ile Gln Gly Ala Leu Glu Leu Arg Thr Lys Val Val Glu Val
            420                 425                 430

Leu Thr Pro Leu Gly Asp Cys Phe Met Leu Arg Ser Asp Ala Val Leu
        435                 440                 445

Asp Phe Ala Thr Val Ser Glu Ile Leu Arg Ser Gly Tyr Thr Arg Ile
450                 455                 460

Pro Val Tyr Glu Gly Asp Gln Arg His Asn Ile Val Asp Ile Leu Phe
```

```
                465                 470                 475                 480
Val Lys Asp Leu Ala Phe Val Asp Pro Asp Cys Thr Pro Leu Leu
                    485                 490                 495

Thr Val Thr Arg Phe Tyr Asn Arg Pro Leu His Cys Val Phe Asn Asp
                500                 505                 510

Thr Arg Leu Asp Thr Val Leu Glu Glu Phe Lys Lys Gly Lys Ser His
            515                 520                 525

Leu Ala Ile Val Gln Arg Val Asn Asn Glu Gly Gly Asp Pro Phe
        530                 535                 540

Tyr Glu Val Met Gly Ile Val Thr Leu Glu Asp Ile Ile Glu Glu Ile
545                 550                 555                 560

Ile Lys Ser Glu Ile Leu Asp Glu Thr Asp Leu Tyr Thr Asp Asn Arg
                565                 570                 575

Lys Lys Gln Arg Val Pro Gln Arg Glu Arg Lys Arg His Asp Phe Ser
                580                 585                 590

Leu Phe Lys Leu Ser Asp Thr Glu Met Arg Val Lys Ile Ser Pro Gln
            595                 600                 605

Leu Leu Leu Ala Thr His Arg Phe Met Ala Thr Glu Val Glu Pro Phe
        610                 615                 620

Lys Ser Leu Tyr Leu Ser Glu Lys Ile Leu Arg Leu Leu Lys His
625                 630                 635                 640

Pro Asn Val Ile Gln Glu Leu Lys Phe Asp Glu Lys Asn Lys Lys Ala
                645                 650                 655

Pro Glu His Tyr Leu Tyr Gln Arg Asn Arg Pro Val Asp Tyr Phe Val
                660                 665                 670

Leu Leu Leu Gln Gly Lys Val Glu Val Glu Val Gly Lys Glu Gly Leu
            675                 680                 685

Arg Phe Glu Asn Gly Ala Phe Thr Tyr Tyr Gly Val Pro Ala Ile Met
        690                 695                 700

Thr Thr Ala Cys Ser Asp Asn Asp Val Arg Lys Val Gly Ser Leu Ala
705                 710                 715                 720

Gly Ser Ser Val Phe Leu Asn Arg Ser Pro Ser Arg Cys Ser Gly Leu
                725                 730                 735

Asn Arg Ser Glu Ser Pro Asn Arg Glu Arg Ser Asp Phe Gly Gly Ser
                740                 745                 750

Asn Thr Gln Leu Tyr Ser Ser Asn Asn Leu Tyr Met Pro Asp Tyr
            755                 760                 765

Ser Val His Ile Leu Ser Asp Val Gln Phe Val Lys Ile Thr Arg Gln
        770                 775                 780

Gln Tyr Gln Asn Ala Leu Thr Ala Cys His Met Asp Ser Ser Pro Gln
785                 790                 795                 800

Ser Pro Asp Met Glu Ala Phe Thr Asp Gly Asp Ser Thr Lys Ala Pro
                805                 810                 815

Thr Thr Arg Gly Thr Pro Gln Thr Pro Lys Asp Asp Pro Ala Ile Thr
                820                 825                 830

Leu Leu Asn Asn Arg Asn Ser Leu Pro Cys Ser Arg Ser Asp Gly Leu
            835                 840                 845

Arg Ser Pro Ser Glu Val Val Tyr Leu Arg Met Glu Glu Leu Ala Phe
        850                 855                 860

Thr Gln Glu Glu Met Thr Asp Phe Glu Glu His Ser Thr Gln Gln Leu
865                 870                 875                 880

Thr Leu Ser Pro Ala Ala Val Pro Thr Arg Ala Ala Ser Asp Ser Glu
                885                 890                 895
```

```
Cys Cys Asn Ile Asn Leu Asp Thr Glu Thr Ser Pro Cys Ser Ser Asp
            900                 905                 910

Phe Glu Glu Asn Val Gly Lys Lys Leu Leu Arg Thr Leu Ser Gly Gln
            915                 920                 925

Lys Arg Lys Arg Ser Pro Glu Gly Glu Arg Thr Ser Glu Asp Asn Ser
            930                 935                 940

Asn Leu Thr Pro Leu Ile Thr
945                 950

<210> SEQ ID NO 10
<211> LENGTH: 875
<212> TYPE: PRT
<213> ORGANISM: Homo sapiens

<400> SEQUENCE: 10

Met Ile Gly Cys Gly Ala Cys Glu Pro Lys Val Lys Met Ala Gly Gly
1               5                   10                  15

Gln Ala Ala Ala Leu Pro Thr Trp Lys Met Ala Ala Arg Arg Ser
            20                  25                  30

Leu Ser Ala Arg Gly Arg Gly Ile Leu Gln Ala Ala Gly Arg Leu
            35                  40                  45

Leu Pro Leu Leu Leu Ser Cys Cys Gly Ala Gly Gly Cys Ala
        50                  55                  60

Ala Val Gly Glu Asn Glu Glu Thr Val Ile Ile Gly Leu Arg Leu Glu
65                  70                  75                  80

Asp Thr Asn Asp Val Ser Phe Met Glu Gly Ala Leu Arg Val Ser
                85                  90                  95

Glu Arg Thr Arg Val Lys Leu Arg Val Tyr Gly Gln Asn Ile Asn Asn
            100                 105                 110

Glu Thr Trp Ser Arg Ile Ala Phe Thr Glu His Glu Arg Arg His
            115                 120                 125

Ser Pro Gly Glu Arg Gly Leu Gly Gly Pro Ala Pro Pro Glu Pro Asp
        130                 135                 140

Ser Gly Pro Gln Arg Cys Gly Ile Arg Thr Ser Asp Ile Ile Leu
145                 150                 155                 160

Pro His Ile Ile Leu Asn Arg Arg Thr Ser Gly Ile Ile Glu Ile Glu
                165                 170                 175

Ile Lys Pro Leu Arg Lys Met Glu Lys Ser Lys Ser Tyr Tyr Leu Cys
            180                 185                 190

Thr Ser Leu Ser Thr Pro Ala Leu Gly Ala Gly Gly Ser Gly Ser Thr
            195                 200                 205

Gly Gly Ala Val Gly Gly Lys Gly Gly Ser Gly Val Ala Gly Leu Pro
        210                 215                 220

Pro Pro Pro Trp Ala Glu Thr Thr Trp Ile Tyr His Asp Gly Glu Asp
225                 230                 235                 240

Thr Lys Met Ile Val Gly Glu Glu Lys Lys Phe Leu Leu Pro Phe Trp
                245                 250                 255

Leu Gln Val Ile Phe Ile Ser Leu Leu Cys Leu Ser Gly Met Phe
            260                 265                 270

Ser Gly Leu Asn Leu Gly Leu Met Ala Leu Asp Pro Met Glu Leu Arg
        275                 280                 285

Ile Val Gln Asn Cys Gly Thr Glu Lys Glu Lys Asn Tyr Ala Lys Arg
    290                 295                 300

Ile Glu Pro Val Arg Arg Gln Gly Asn Tyr Leu Leu Cys Ser Leu Leu
```

-continued

```
            305                 310                 315                 320
Leu Gly Asn Val Leu Val Asn Thr Thr Leu Thr Ile Leu Leu Asp Asp
                325                 330                 335
Ile Ala Gly Ser Gly Leu Val Ala Val Val Ser Thr Ile Gly Ile
                340                 345                 350
Val Ile Phe Gly Glu Ile Val Pro Gln Ala Ile Cys Ser Arg His Gly
                355                 360                 365
Leu Ala Val Gly Ala Asn Thr Ile Phe Leu Thr Lys Phe Phe Met Met
                370                 375                 380
Met Thr Phe Pro Ala Ser Tyr Pro Val Ser Lys Leu Leu Asp Cys Val
385                 390                 395                 400
Leu Gly Gln Glu Ile Gly Thr Val Tyr Asn Arg Glu Lys Leu Leu Glu
                405                 410                 415
Met Leu Arg Val Thr Asp Pro Tyr Asn Asp Leu Val Lys Glu Glu Leu
                420                 425                 430
Asn Ile Ile Gln Gly Ala Leu Glu Leu Arg Thr Lys Thr Val Glu Asp
                435                 440                 445
Val Met Thr Pro Leu Arg Asp Cys Phe Met Ile Thr Gly Glu Ala Ile
    450                 455                 460
Leu Asp Phe Asn Thr Met Ser Glu Ile Met Glu Ser Gly Tyr Thr Arg
465                 470                 475                 480
Ile Pro Val Phe Glu Gly Glu Arg Ser Asn Ile Val Asp Leu Leu Phe
                485                 490                 495
Val Lys Asp Leu Ala Phe Val Asp Pro Asp Asp Cys Thr Pro Leu Lys
                500                 505                 510
Thr Ile Thr Lys Phe Tyr Asn His Pro Leu His Phe Val Phe Asn Asp
                515                 520                 525
Thr Lys Leu Asp Ala Met Leu Glu Glu Phe Lys Lys Gly Lys Ser His
                530                 535                 540
Leu Ala Ile Val Gln Arg Val Asn Asn Glu Gly Glu Gly Asp Pro Phe
545                 550                 555                 560
Tyr Glu Val Leu Gly Ile Val Thr Leu Glu Asp Val Ile Glu Glu Ile
                565                 570                 575
Ile Lys Ser Glu Ile Leu Asp Glu Thr Asp Leu Tyr Thr Asp Asn Arg
                580                 585                 590
Thr Lys Lys Lys Val Ala His Arg Glu Arg Lys Gln Asp Phe Ser Ala
                595                 600                 605
Phe Lys Gln Thr Asp Ser Glu Met Lys Val Lys Ile Ser Pro Gln Leu
    610                 615                 620
Leu Leu Ala Met His Arg Phe Leu Ala Thr Glu Val Glu Ala Phe Ser
625                 630                 635                 640
Pro Ser Gln Met Ser Glu Lys Ile Leu Leu Arg Leu Lys His Pro
                645                 650                 655
Asn Val Ile Gln Glu Leu Lys Tyr Asp Glu Lys Asn Lys Lys Ala Pro
                660                 665                 670
Glu Tyr Tyr Leu Tyr Gln Arg Asn Lys Pro Val Asp Tyr Phe Val Leu
                675                 680                 685
Ile Leu Gln Gly Lys Val Glu Val Glu Ala Gly Lys Glu Gly Met Lys
                690                 695                 700
Phe Glu Ala Ser Ala Phe Ser Tyr Tyr Gly Val Met Ala Leu Thr Ala
705                 710                 715                 720
Ser Pro Val Pro Leu Ser Leu Ser Arg Thr Phe Val Val Ser Arg Thr
                725                 730                 735
```

```
Glu Leu Leu Ala Ala Gly Ser Pro Gly Glu Asn Lys Ser Pro Pro Arg
            740                 745                 750

Pro Cys Gly Leu Asn His Ser Asp Ser Leu Ser Arg Ser Asp Arg Ile
            755                 760                 765

Asp Ala Val Thr Pro Thr Leu Gly Ser Ser Asn Asn Gln Leu Asn Ser
            770                 775                 780

Ser Leu Leu Gln Val Tyr Ile Pro Asp Tyr Ser Val Arg Ala Leu Ser
785                 790                 795                 800

Asp Leu Gln Phe Val Lys Ile Ser Arg Gln Gln Tyr Gln Asn Ala Leu
                805                 810                 815

Met Ala Ser Arg Met Asp Lys Thr Pro Gln Ser Ser Asp Ser Glu Asn
            820                 825                 830

Thr Lys Ile Glu Leu Thr Leu Thr Glu Leu His Asp Gly Leu Pro Asp
            835                 840                 845

Glu Thr Ala Asn Leu Leu Asn Glu Gln Asn Cys Val Thr His Ser Lys
            850                 855                 860

Ala Asn His Ser Leu His Asn Glu Gly Ala Ile
865                 870                 875

<210> SEQ ID NO 11
<211> LENGTH: 707
<212> TYPE: PRT
<213> ORGANISM: Homo sapiens

<400> SEQUENCE: 11

Met Ala Ala Ala Val Ala Ala Ala Gly Arg Leu Gly Trp Leu Phe Ala
1               5                   10                  15

Ala Leu Cys Leu Gly Asn Ala Ala Gly Glu Ala Ala Pro Gly Pro Arg
            20                  25                  30

Val Leu Gly Phe Cys Leu Glu Glu Asp Gly Ala Ala Gly Ala Gly Trp
            35                  40                  45

Val Arg Gly Gly Ala Ala Arg Asp Thr Pro Asp Ala Thr Phe Leu Leu
    50                  55                  60

Arg Leu Phe Gly Pro Gly Phe Ala Asn Ser Ser Trp Ser Trp Val Ala
65                  70                  75                  80

Pro Glu Gly Ala Gly Cys Arg Glu Glu Ala Ser Pro Ala Gly Glu
            85                  90                  95

Trp Arg Ala Leu Leu Arg Leu Arg Leu Arg Ala Glu Ala Val Arg Pro
            100                 105                 110

His Ser Ala Leu Leu Ala Val Arg Val Glu Pro Gly Gly Gly Ala Ala
            115                 120                 125

Glu Glu Ala Ala Pro Pro Trp Ser Leu Gly Leu Gly Ala Ala Gly Leu
            130                 135                 140

Leu Ala Leu Ala Ala Leu Ala Arg Gly Leu Gln Leu Ser Ala Leu Ala
145                 150                 155                 160

Leu Ala Pro Ala Glu Val Gln Val Leu Arg Glu Ser Gly Ser Glu Ala
            165                 170                 175

Glu Arg Ala Ala Ala Arg Arg Leu Glu Pro Ala Arg Arg Trp Ala Gly
            180                 185                 190

Cys Ala Leu Gly Ala Leu Leu Leu Ala Ile Leu Ala His Ala Ala
            195                 200                 205

Leu Ala Val Leu Leu Tyr Arg Ala Ala Gly Gln Arg Ala Val Pro Ala
            210                 215                 220

Val Leu Gly Ser Ala Gly Leu Val Phe Leu Val Gly Glu Val Val Pro
```

```
                    225                 230                 235                 240
         Ala Ala Val Ser Gly Arg Trp Thr Leu Ala Leu Ala Pro Arg Ala Leu
                         245                 250                 255
         Gly Leu Ser Arg Leu Ala Val Leu Leu Thr Leu Pro Val Ala Leu Pro
                         260                 265                 270
         Val Gly Gln Leu Leu Glu Leu Ala Ala Arg Pro Gly Arg Leu Arg Glu
                         275                 280                 285
         Arg Val Leu Glu Leu Ala Arg Gly Gly Asp Pro Tyr Ser Asp Leu
                         290                 295                 300
         Ser Lys Gly Val Leu Arg Cys Arg Thr Val Glu Asp Val Leu Thr Pro
         305                 310                 315                 320
         Leu Glu Asp Cys Phe Met Leu Asp Ala Ser Thr Val Leu Asp Phe Gly
                             325                 330                 335
         Val Leu Ala Ser Ile Met Gln Ser Gly His Thr Arg Ile Pro Val Tyr
                             340                 345                 350
         Glu Glu Glu Arg Ser Asn Ile Val Asp Met Leu Tyr Leu Lys Asp Leu
                             355                 360                 365
         Ala Phe Val Asp Pro Glu Asp Cys Thr Pro Leu Ser Thr Ile Thr Arg
                 370                 375                 380
         Phe Tyr Asn His Pro Leu His Phe Val Phe Asn Asp Thr Lys Leu Asp
         385                 390                 395                 400
         Ala Val Leu Glu Glu Phe Lys Arg Gly Lys Ser His Leu Ala Ile Val
                             405                 410                 415
         Gln Lys Val Asn Asn Glu Gly Glu Gly Asp Pro Phe Tyr Glu Val Leu
                             420                 425                 430
         Gly Leu Val Thr Leu Glu Asp Val Ile Glu Glu Ile Ile Arg Ser Glu
                             435                 440                 445
         Ile Leu Asp Glu Ser Glu Asp Tyr Arg Asp Thr Val Val Lys Arg Lys
                 450                 455                 460
         Pro Ala Ser Leu Met Ala Pro Leu Lys Arg Lys Glu Glu Phe Ser Leu
         465                 470                 475                 480
         Phe Lys Val Ser Asp Asp Glu Tyr Lys Val Thr Ile Ser Pro Gln Leu
                             485                 490                 495
         Leu Leu Ala Thr Gln Arg Phe Leu Ser Arg Glu Val Asp Val Phe Ser
                             500                 505                 510
         Pro Leu Arg Ile Ser Glu Lys Val Leu Leu His Leu Lys His Pro
                     515                 520                 525
         Ser Val Asn Gln Glu Val Arg Phe Asp Glu Ser Asn Arg Leu Ala Thr
                 530                 535                 540
         His His Tyr Leu Tyr Gln Arg Ser Gln Pro Val Asp Tyr Phe Ile Leu
         545                 550                 555                 560
         Ile Leu Gln Gly Arg Val Glu Val Glu Ile Gly Lys Glu Gly Leu Lys
                             565                 570                 575
         Phe Glu Asn Gly Ala Phe Thr Tyr Tyr Gly Val Ser Ala Leu Thr Val
                         580                 585                 590
         Pro Ser Ser Val His Gln Ser Pro Val Ser Leu Gln Pro Ile Arg
                     595                 600                 605
         His Asp Leu Gln Pro Asp Pro Gly Asp Gly Thr His Ser Ser Ala Tyr
                     610                 615                 620
         Cys Pro Asp Tyr Thr Val Arg Ala Leu Ser Asp Leu Gln Leu Ile Lys
         625                 630                 635                 640
         Val Thr Arg Leu Gln Tyr Leu Asn Ala Leu Leu Ala Thr Arg Ala Gln
                             645                 650                 655
```

```
Asn Leu Pro Gln Ser Pro Glu Asn Thr Asp Leu Gln Val Ile Pro Gly
            660                 665                 670

Ser Gln Thr Arg Leu Leu Gly Glu Lys Thr Thr Ala Ala Gly Ser
        675                 680                 685

Ser His Ser Arg Pro Gly Val Pro Val Glu Gly Ser Pro Gly Arg Asn
        690                 695                 700

Pro Gly Val
705

<210> SEQ ID NO 12
<211> LENGTH: 775
<212> TYPE: PRT
<213> ORGANISM: Homo sapiens

<400> SEQUENCE: 12

Met Ala Pro Val Gly Gly Gly Arg Pro Val Gly Pro Ala Arg
1               5                   10                  15

Gly Arg Leu Leu Leu Ala Ala Pro Val Leu Leu Val Leu Leu Trp Ala
            20                  25                  30

Leu Gly Ala Arg Gly Gln Gly Ser Pro Gln Gly Thr Ile Val Gly
            35                  40                  45

Met Arg Leu Ala Ser Cys Asn Lys Ser Cys Gly Thr Asn Pro Asp Gly
50                  55                  60

Ile Ile Phe Val Ser Glu Gly Ser Thr Val Asn Leu Arg Leu Tyr Gly
65                  70                  75                  80

Tyr Ser Leu Gly Asn Ile Ser Ser Asn Leu Ile Ser Phe Thr Glu Val
                85                  90                  95

Asp Asp Ala Glu Thr Leu His Lys Ser Thr Ser Cys Leu Glu Leu Thr
            100                 105                 110

Lys Asp Leu Val Val Gln Gln Leu Val Asn Val Ser Arg Gly Asn Thr
        115                 120                 125

Ser Gly Val Leu Val Val Leu Thr Lys Phe Leu Arg Arg Ser Glu Ser
    130                 135                 140

Met Lys Leu Tyr Ala Leu Cys Thr Arg Ala Gln Pro Asp Gly Pro Trp
145                 150                 155                 160

Leu Lys Trp Thr Asp Lys Asp Ser Leu Leu Phe Met Val Glu Glu Pro
                165                 170                 175

Gly Arg Phe Leu Pro Leu Trp Leu His Ile Leu Leu Ile Thr Val Leu
            180                 185                 190

Leu Val Leu Ser Gly Ile Phe Ser Gly Leu Asn Leu Gly Leu Met Ala
        195                 200                 205

Leu Asp Pro Met Glu Leu Arg Ile Val Gln Asn Cys Gly Thr Glu Lys
    210                 215                 220

Glu Arg Arg Tyr Ala Arg Lys Ile Glu Pro Ile Arg Arg Lys Gly Asn
225                 230                 235                 240

Tyr Leu Leu Cys Ser Leu Leu Leu Gly Asn Val Leu Val Asn Thr Ser
                245                 250                 255

Leu Thr Ile Leu Leu Asp Asn Leu Ile Gly Ser Gly Leu Met Ala Val
            260                 265                 270

Ala Ser Ser Thr Ile Gly Ile Val Ile Phe Gly Glu Ile Leu Pro Gln
        275                 280                 285

Ala Leu Cys Ser Arg His Gly Leu Ala Val Gly Ala Asn Ile Ile Leu
    290                 295                 300

Leu Thr Lys Phe Phe Met Leu Leu Thr Phe Pro Leu Ser Phe Pro Ile
```

-continued

```
                305                 310                 315                 320
Ser Lys Leu Leu Asp Phe Phe Leu Gly Gln Glu Ile Arg Thr Val Tyr
                    325                 330                 335
Asn Arg Glu Lys Leu Met Glu Met Leu Lys Val Thr Glu Pro Tyr Asn
                340                 345                 350
Asp Leu Val Lys Glu Glu Leu Asn Met Ile Gln Gly Ala Leu Glu Leu
                355                 360                 365
Arg Thr Lys Thr Val Glu Asp Ile Met Thr Gln Leu Gln Asp Cys Phe
                370                 375                 380
Met Ile Arg Ser Asp Ala Ile Leu Asp Phe Asn Thr Met Ser Glu Ile
385                 390                 395                 400
Met Glu Ser Gly Tyr Thr Arg Ile Pro Val Phe Glu Asp Gln Ser
                    405                 410                 415
Asn Ile Val Asp Ile Leu Tyr Val Lys Asp Leu Ala Phe Val Asp Pro
                420                 425                 430
Asp Asp Cys Thr Pro Leu Lys Thr Ile Thr Arg Phe Tyr Asn His Pro
                435                 440                 445
Val His Phe Val Phe His Asp Thr Lys Leu Asp Ala Met Leu Glu Glu
            450                 455                 460
Phe Lys Lys Gly Lys Ser His Leu Ala Ile Val Gln Lys Val Asn Asn
465                 470                 475                 480
Glu Gly Glu Gly Asp Pro Phe Tyr Glu Val Leu Gly Leu Val Thr Leu
                    485                 490                 495
Glu Asp Val Ile Glu Glu Ile Ile Lys Ser Glu Ile Leu Asp Glu Ser
                500                 505                 510
Asp Met Tyr Thr Asp Asn Arg Ser Arg Lys Arg Val Ser Glu Lys Asn
            515                 520                 525
Lys Arg Asp Phe Ser Ala Phe Lys Asp Ala Asp Asn Glu Leu Lys Val
        530                 535                 540
Lys Ile Ser Pro Gln Leu Leu Leu Ala Ala His Arg Phe Leu Ala Thr
545                 550                 555                 560
Glu Val Ser Gln Phe Ser Pro Ser Leu Ile Ser Glu Lys Ile Leu Leu
                    565                 570                 575
Arg Leu Leu Lys Tyr Pro Asp Val Ile Gln Glu Leu Lys Phe Asp Glu
                580                 585                 590
His Asn Lys Tyr Tyr Ala Arg His Tyr Leu Tyr Thr Arg Asn Lys Pro
            595                 600                 605
Ala Asp Tyr Phe Ile Leu Ile Leu Gln Gly Lys Val Glu Val Glu Ala
        610                 615                 620
Gly Lys Glu Asn Met Lys Phe Glu Thr Gly Ala Phe Ser Tyr Tyr Gly
625                 630                 635                 640
Thr Met Ala Leu Thr Ser Val Pro Ser Asp Arg Ser Pro Ala His Pro
                    645                 650                 655
Thr Pro Leu Ser Arg Ser Ala Ser Leu Ser Tyr Pro Asp Arg Thr Asp
                660                 665                 670
Val Ser Thr Ala Ala Thr Leu Ala Gly Ser Ser Asn Gln Phe Gly Ser
            675                 680                 685
Ser Val Leu Gly Gln Tyr Ile Ser Asp Phe Ser Val Arg Ala Leu Val
        690                 695                 700
Asp Leu Gln Tyr Ile Lys Ile Thr Arg Gln Gln Tyr Gln Asn Gly Leu
705                 710                 715                 720
Leu Ala Ser Arg Met Glu Asn Ser Pro Gln Phe Pro Ile Asp Gly Cys
                    725                 730                 735
```

```
Thr Thr His Met Glu Asn Leu Ala Glu Lys Ser Glu Leu Pro Val Val
        740                 745                 750

Asp Glu Thr Thr Thr Leu Leu Asn Glu Arg Asn Ser Leu Leu His Lys
        755                 760                 765

Ala Ser His Glu Asn Ala Ile
        770                 775

<210> SEQ ID NO 13
<211> LENGTH: 951
<212> TYPE: PRT
<213> ORGANISM: Mus musculus

<400> SEQUENCE: 13

Met Ala Ala Ala Ala Ala Ala Ala Leu Gly Val Arg Leu Arg
1               5                   10                  15

Asp Cys Cys Ser Arg Gly Ala Val Leu Leu Phe Phe Ser Leu Ser
                20                  25                  30

Pro Arg Pro Ala Ala Ala Trp Leu Leu Gly Leu Arg Pro Glu
        35                  40                  45

Asp Thr Ala Gly Ala Arg Val Ser Leu Glu Gly Thr Leu Arg Ala
    50                  55                  60

Ala Glu Gly Thr Ser Phe Leu Leu Arg Val Tyr Phe Gln Pro Gly Pro
65              70                  75                      80

Pro Val Pro Ala Ala Pro Val Pro Ala Pro Ser Leu Ala Pro Gly Glu
                85                  90                  95

Asn Gly Thr Gly Asp Trp Ala Pro Arg Leu Val Phe Ile Glu Pro
            100                 105                 110

Pro Gly Ala Gly Ala Ala Pro Ser Ala Val Pro Thr Arg Pro Pro
        115                 120                 125

Gly Pro Gln Arg Cys Arg Glu Gln Ser Asp Trp Ala Ser Asp Val Glu
    130                 135                 140

Val Leu Gly Pro Leu Arg Pro Gly Gly Val Ala Gly Ser Ala Leu Val
145                 150                 155                 160

Gln Val Arg Val Arg Glu Leu Arg Lys Gly Glu Ala Glu Arg Gly Gly
                165                 170                 175

Ala Gly Gly Gly Lys Leu Phe Ser Leu Cys Ala Trp Asp Gly Arg
            180                 185                 190

Ala Trp His His His Gly Ala Ala Gly Gly Phe Leu Leu Arg Val Arg
                195                 200                 205

Pro Arg Leu Tyr Gly Pro Gly Gly Asp Leu Leu Pro Pro Ala Trp Leu
    210                 215                 220

Arg Ala Leu Gly Ala Leu Leu Leu Ala Leu Ser Ala Leu Phe Ser
225                 230                 235                 240

Gly Leu Arg Leu Ser Leu Leu Ser Leu Asp Pro Val Glu Leu Arg Val
                245                 250                 255

Leu Arg Asn Ser Gly Ser Ala Ala Glu Gln Glu Gln Ala Arg Arg Val
            260                 265                 270

Gln Ala Val Arg Gly Arg Gly Thr His Leu Leu Cys Thr Leu Leu Leu
        275                 280                 285

Gly Gln Ala Gly Ala Asn Ala Ala Leu Ala Gly Trp Leu Tyr Ala Ser
    290                 295                 300

Leu Pro Pro Gly Val Gly Asp Pro Gly Glu Asp Ser Gly Glu Ala Gly
305                 310                 315                 320

Val His Phe Pro Trp Leu Pro Ala Leu Val Cys Thr Gly Ala Val Phe
```

-continued

```
                325                 330                 335
Leu Gly Ala Glu Ile Cys Pro Tyr Ser Val Cys Ser Arg His Gly Leu
            340                 345                 350
Ala Ile Ala Ser His Ser Val Cys Leu Thr Arg Leu Leu Met Ala Ala
        355                 360                 365
Ala Phe Pro Val Cys Tyr Pro Leu Gly Arg Leu Leu Asp Trp Ala Leu
    370                 375                 380
Arg Gln Glu Ile Ser Thr Phe Tyr Thr Arg Glu Lys Leu Leu Glu Thr
385                 390                 395                 400
Leu Arg Ala Ala Asp Pro Tyr Ser Asp Leu Val Lys Glu Leu Asn
            405                 410                 415
Ile Ile Gln Gly Ala Leu Glu Leu Arg Thr Lys Val Val Glu Glu Val
            420                 425                 430
Leu Thr Pro Leu Gly Asp Cys Phe Met Leu Arg Ser Asp Ala Val Leu
        435                 440                 445
Asp Phe Ala Thr Val Ser Glu Ile Leu Arg Ser Gly Tyr Thr Arg Ile
    450                 455                 460
Pro Val Tyr Glu Gly Asp Gln Arg His Asn Ile Val Asp Ile Leu Phe
465                 470                 475                 480
Val Lys Asp Leu Ala Phe Val Asp Pro Asp Asp Cys Thr Pro Leu Leu
            485                 490                 495
Thr Val Thr Arg Phe Tyr Asn Arg Pro Leu His Cys Val Phe Asn Asp
            500                 505                 510
Thr Arg Leu Asp Thr Val Leu Glu Glu Phe Lys Lys Gly Lys Ser His
        515                 520                 525
Leu Ala Ile Val Gln Arg Val Asn Asn Glu Gly Glu Gly Asp Pro Phe
    530                 535                 540
Tyr Glu Val Met Gly Ile Val Thr Leu Glu Asp Ile Ile Glu Glu Ile
545                 550                 555                 560
Ile Lys Ser Glu Ile Leu Asp Glu Thr Asp Leu Tyr Thr Asp Asn Arg
            565                 570                 575
Lys Lys Gln Arg Val Pro His Arg Glu Arg Arg His Asp Phe Ser
            580                 585                 590
Leu Phe Lys Leu Ser Asp Ser Glu Ile Arg Val Lys Ile Ser Pro Gln
        595                 600                 605
Leu Leu Leu Ala Thr His Arg Phe Met Ala Thr Glu Val Glu Pro Phe
    610                 615                 620
Lys Ser Leu Tyr Leu Ser Glu Lys Ile Leu Leu Arg Leu Leu Lys His
625                 630                 635                 640
Pro Asn Val Ile Gln Glu Leu Lys Phe Asp Glu Arg Asn Lys Lys Ala
            645                 650                 655
Pro Glu His Tyr Leu Tyr Gln Arg Asn Arg Pro Val Asp Tyr Phe Val
            660                 665                 670
Leu Leu Leu Gln Gly Lys Val Glu Val Gly Lys Glu Gly Leu
        675                 680                 685
Arg Phe Glu Asn Gly Ala Phe Thr Tyr Tyr Gly Val Pro Ala Ile Met
    690                 695                 700
Thr Ser Ala Phe Ser Asp Asn Asp Val Arg Lys Val Gly Ser Leu Ala
705                 710                 715                 720
Gly Ser Ser Val Phe Leu Asn Arg Ser Pro Ser Arg Cys Ser Gly Leu
            725                 730                 735
Asn Arg Ser Glu Ser Pro Asn Arg Glu Arg Ser Asp Phe Gly Gly Ser
            740                 745                 750
```

-continued

```
Asn Thr Gln Leu Tyr Ser Ser Asn Asn Leu Tyr Thr Pro Asp Tyr
        755                 760                 765

Ser Val His Ile Leu Ser Asp Val Gln Phe Val Lys Ile Thr Arg Gln
    770                 775                 780

Gln Tyr Gln Asn Ala Leu Thr Ala Cys His Met Asp Ser Ser Pro Gln
785                 790                 795                 800

Ser Pro Asp Met Glu Ala Phe Thr Asp Gly Asp Ser Thr Lys Ala Pro
                805                 810                 815

Thr Thr Arg Gly Thr Pro Gln Thr Pro Lys Asp Asp Pro Val Leu Thr
                820                 825                 830

Leu Leu Ser Asn Arg Thr Ser Leu Pro Cys Ser Arg Ser Asp Gly Leu
            835                 840                 845

Arg Ser Pro Gly Glu Val Val Tyr Leu Arg Met Glu Glu Met Ala Phe
    850                 855                 860

Pro Gln Glu Glu Met Pro Asn Phe Glu Glu His Arg Ser Gln Gln Val
865                 870                 875                 880

Ser Leu Ser Pro Val Ala Val Pro Thr Thr Ala Ala Ser Asp Pro Glu
                885                 890                 895

Cys Cys Asn Ile His Leu Asp Pro Glu Ala Ser Pro Cys Ser Ser Asp
                900                 905                 910

Ser Glu Glu Asn Met Gly Lys Lys Leu Leu Arg Thr Leu Ser Gly Arg
            915                 920                 925

Lys Arg Lys Lys Ser Ala Asp Gly Glu Arg Ala Ser Glu Glu Asn Ser
    930                 935                 940

Asn Leu Thr Pro Leu Ile Thr
945                 950

<210> SEQ ID NO 14
<211> LENGTH: 862
<212> TYPE: PRT
<213> ORGANISM: Mus musculus

<400> SEQUENCE: 14

Met Ala Gly Gly Gln Ala Ala Ala Leu Pro Thr Trp Lys Met Ala
1               5                   10                  15

Ala Arg Arg Ser Leu Ser Ala Arg Gly Arg Gly Val Leu Gln Ala Ala
            20                  25                  30

Ala Gly Arg Leu Leu Pro Leu Leu Leu Ser Cys Cys Trp Gly Ala
        35                  40                  45

Gly Gly Cys Thr Ala Gly Gly Glu Thr Glu Glu Thr Val Ile Ile Gly
    50                  55                  60

Leu Arg Leu Glu Asp Thr Asn Asp Val Ser Phe Met Glu Gly Gly Ala
65                  70                  75                  80

Leu Arg Val Ser Glu Arg Thr Arg Val Lys Leu Arg Val Tyr Gly Gln
                85                  90                  95

Asn Ile Asn Asn Glu Thr Trp Ser Arg Ile Ala Phe Thr Glu His Glu
            100                 105                 110

Arg Arg Arg His Thr Pro Gly Glu Arg Gly Leu Gly Pro Ala Pro
            115                 120                 125

Pro Glu Pro Asp Ser Gly Pro Gln Arg Cys Gly Ile Arg Thr Ser Asp
    130                 135                 140

Ile Ile Ile Leu Pro His Ile Ile Leu Asn Arg Arg Thr Ser Gly Ile
145                 150                 155                 160

Ile Glu Ile Glu Ile Lys Pro Leu Arg Lys Met Glu Lys Ser Lys Ser
```

-continued

```
                165                 170                 175
Tyr Tyr Leu Cys Thr Ser Leu Ser Thr Pro Ala Leu Gly Ala Gly Gly
            180                 185                 190

Ser Gly Ser Ala Ser Gly Thr Val Gly Gly Lys Gly Gly Ala Gly Val
        195                 200                 205

Ala Gly Leu Pro Pro Pro Trp Ala Glu Thr Thr Trp Ile Tyr His
    210                 215                 220

Asp Gly Glu Asp Thr Lys Met Ile Val Gly Glu Lys Lys Phe Leu
225                 230                 235                 240

Leu Pro Phe Trp Leu Gln Val Ile Phe Ile Ser Leu Leu Cys Leu
                245                 250                 255

Ser Gly Met Phe Ser Gly Leu Asn Leu Gly Leu Met Ala Leu Asp Pro
            260                 265                 270

Met Glu Leu Arg Ile Val Gln Asn Cys Gly Thr Glu Lys Glu Lys Asn
        275                 280                 285

Tyr Ala Lys Arg Ile Glu Pro Val Arg Arg Gln Gly Asn Tyr Leu Leu
    290                 295                 300

Cys Ser Leu Leu Leu Gly Asn Val Leu Val Asn Thr Thr Leu Thr Ile
305                 310                 315                 320

Leu Leu Asp Asp Ile Ala Gly Ser Gly Leu Val Ala Val Val Ser
                325                 330                 335

Thr Ile Gly Ile Val Ile Phe Gly Glu Ile Val Pro Gln Ala Ile Cys
            340                 345                 350

Ser Arg His Gly Leu Ala Val Gly Ala Asn Thr Ile Phe Leu Thr Lys
        355                 360                 365

Phe Phe Met Met Met Thr Phe Pro Ala Ser Tyr Pro Val Ser Lys Leu
370                 375                 380

Leu Asp Cys Val Leu Gly Gln Glu Ile Gly Thr Val Tyr Asn Arg Glu
385                 390                 395                 400

Lys Leu Leu Glu Met Leu Arg Val Thr Asp Pro Tyr Asn Asp Leu Val
                405                 410                 415

Lys Glu Glu Leu Asn Ile Ile Gln Gly Ala Leu Glu Leu Arg Thr Lys
            420                 425                 430

Thr Val Glu Asp Val Met Thr Pro Leu Arg Asp Cys Phe Met Ile Thr
        435                 440                 445

Gly Glu Ala Ile Leu Asp Phe Asn Thr Met Ser Glu Ile Met Glu Ser
    450                 455                 460

Gly Tyr Thr Arg Ile Pro Val Phe Glu Gly Glu Arg Ser Asn Ile Val
465                 470                 475                 480

Asp Leu Leu Phe Val Lys Asp Leu Ala Phe Val Asp Pro Asp Cys
                485                 490                 495

Thr Pro Leu Lys Thr Ile Thr Lys Phe Tyr Asn His Pro Leu His Phe
            500                 505                 510

Val Phe Asn Asp Thr Lys Leu Asp Ala Met Leu Glu Phe Lys Lys
        515                 520                 525

Gly Lys Ser His Leu Ala Ile Val Gln Arg Val Asn Asn Glu Gly Glu
    530                 535                 540

Gly Asp Pro Phe Tyr Glu Val Leu Gly Ile Val Thr Leu Glu Asp Val
545                 550                 555                 560

Ile Glu Glu Ile Ile Lys Ser Glu Leu Asp Glu Thr Asp Leu Tyr Thr
                565                 570                 575

Asp Asn Arg Thr Lys Lys Lys Val Ala His Arg Glu Arg Lys Gln Asp
            580                 585                 590
```

```
Phe Ser Ala Phe Lys Gln Thr Asp Ser Glu Met Lys Val Lys Ile Ser
            595                 600                 605

Pro Gln Leu Leu Leu Ala Met His Arg Phe Leu Ala Thr Glu Val Glu
        610                 615                 620

Ala Phe Ser Pro Ser Gln Met Ser Glu Lys Ile Leu Leu Arg Leu Leu
625                 630                 635                 640

Lys His Pro Asn Val Ile Gln Glu Leu Lys Tyr Asp Glu Lys Asn Lys
            645                 650                 655

Lys Ala Pro Glu Cys Tyr Leu Tyr Gln Arg Asn Lys Pro Val Asp Tyr
        660                 665                 670

Phe Val Leu Ile Leu Gln Gly Lys Val Glu Val Glu Ala Gly Lys Glu
            675                 680                 685

Gly Met Lys Phe Glu Ala Ser Ala Phe Ser Tyr Tyr Gly Val Met Ala
        690                 695                 700

Leu Thr Ala Ser Pro Val Pro Leu Ser Leu Ser Arg Thr Phe Val Val
705                 710                 715                 720

Ser Arg Thr Glu Val Leu Ala Ala Gly Ser Pro Gly Glu Asn Lys Ser
            725                 730                 735

Pro Pro Arg Pro Cys Gly Leu Asn His Ser Asp Ser Leu Ser Arg Ser
        740                 745                 750

Asp Arg Ile Asp Ala Met Thr Pro Thr Leu Gly Ser Ser Asn Asn Gln
            755                 760                 765

Leu Ser Ser Ser Phe Leu Gln Val Tyr Ile Pro Asp Tyr Ser Val Arg
        770                 775                 780

Ala Leu Ser Asp Leu Gln Phe Val Lys Ile Ser Arg Gln Gln Tyr Gln
785                 790                 795                 800

Asn Ala Leu Met Ala Ser Arg Met Asp Lys Thr Pro Gln Ser Ser Asp
            805                 810                 815

Ser Glu Asn Thr Lys Ile Glu Leu Thr Leu Thr Glu Leu His Asp Gly
        820                 825                 830

Leu Pro Asp Glu Thr Ala Asn Leu Leu Asn Glu Gln Asn Cys Val Ser
        835                 840                 845

His Asn Lys Ala Asn His Ser Leu His Ser Glu Gly Ala Ile
850                 855                 860

<210> SEQ ID NO 15
<211> LENGTH: 712
<212> TYPE: PRT
<213> ORGANISM: Mus musculus

<400> SEQUENCE: 15

Met Ala Ala Ala Ala Ala Val Val Gly Trp Leu Gly Trp Val Leu
1               5                   10                  15

Ala Ala Phe Cys Leu Gly Ser Thr Ala Gly Glu Ala Ala Pro Ala Pro
            20                  25                  30

Gly Ala Gly Leu Leu Asn Phe Cys Thr Glu Glu Asp Ser Ala Pro Gly
        35                  40                  45

Ala Gly Ser Leu Arg Gly Arg Ala Ala Pro Glu Ala Thr Leu Cys Leu
    50                  55                  60

Arg Leu Phe Cys Ser Gly Leu Ala Asn Ser Ser Trp Thr Trp Val Ala
65                  70                  75                  80

Ala Glu Gly Ala Gly Cys Pro Glu Gly Gly Arg Ala Thr Glu Pro Glu
            85                  90                  95

Glu Ala Ala Ala Pro Thr Gly Glu Trp Arg Ala Leu Leu Arg Leu Arg
```

-continued

```
              100                 105                 110
Ala Glu Ala Gly His Pro Arg Ser Ala Leu Leu Ala Val Arg Val Glu
            115                 120                 125
Pro Gly Gly Ala Ala Glu Ala Ala Pro Pro Trp Ala Leu Gly
130                 135                 140
Leu Gly Ala Ala Gly Leu Leu Ala Leu Ala Ala Val Ala Arg Gly Leu
145                 150                 155                 160
Gln Leu Ser Ala Leu Ala Leu Ala Pro Ala Glu Val Gln Val Leu Arg
                165                 170                 175
Glu Ser Gly Ser Glu Ala Glu Arg Ala Ala Arg Arg Leu Glu Pro
            180                 185                 190
Ala Arg Arg Trp Ala Gly Cys Ala Leu Gly Ala Leu Leu Leu Ala
            195                 200                 205
Ser Leu Ala Gln Ala Ala Leu Ala Val Leu Leu Tyr Gly Ala Ala Gly
    210                 215                 220
Gln Arg Ala Val Pro Ala Val Leu Gly Cys Ala Gly Leu Val Phe Leu
225                 230                 235                 240
Val Gly Glu Val Leu Pro Ala Ala Val Ser Gly Arg Trp Ala Leu Ala
                245                 250                 255
Leu Ala Pro Arg Ala Leu Gly Leu Ser Arg Leu Ala Val Leu Leu Thr
            260                 265                 270
Leu Pro Val Ala Leu Pro Val Gly Gln Leu Leu Glu Leu Ala Ala Arg
        275                 280                 285
Pro Gly Arg Leu Arg Glu Arg Val Leu Glu Leu Ala Arg Gly Gly Gly
        290                 295                 300
Asp Pro Tyr Ser Asp Leu Ser Lys Gly Val Leu Arg Ser Arg Thr Val
305                 310                 315                 320
Glu Asp Val Leu Thr Pro Leu Glu Asp Cys Phe Met Leu Asp Ser Gly
                325                 330                 335
Thr Val Leu Asp Phe Ser Val Leu Ala Ser Ile Met Gln Ser Gly His
            340                 345                 350
Thr Arg Ile Pro Val Tyr Glu Glu Arg Ser Asn Ile Val Asp Met
            355                 360                 365
Leu Tyr Leu Lys Asp Leu Ala Ile Val Glu Pro Glu Asp Cys Thr Pro
370                 375                 380
Leu Ser Thr Ile Thr Arg Phe Tyr Asn His Pro Leu His Phe Val Phe
385                 390                 395                 400
Asn Asp Thr Lys Leu Asp Ala Val Leu Glu Glu Phe Lys Arg Gly Lys
                405                 410                 415
Ser His Leu Ala Ile Val Gln Lys Val Asn Asn Glu Gly Glu Gly Asp
            420                 425                 430
Pro Phe Tyr Glu Val Leu Gly Leu Val Thr Leu Glu Asp Val Ile Glu
            435                 440                 445
Glu Ile Ile Lys Ser Glu Ile Leu Asp Glu Ser Glu Asp Tyr Ser Asp
        450                 455                 460
Thr Lys Val Arg Lys Thr Val Ala Leu Gly Ala Pro Leu Lys Arg
465                 470                 475                 480
Lys Glu Glu Phe Ser Leu Phe Lys Val Ser Asp Asp Glu Tyr Lys Val
                485                 490                 495
Lys Ile Ser Pro Gln Leu Leu Leu Ala Thr Gln Arg Phe Leu Ser Arg
            500                 505                 510
Glu Val Asp Val Phe Ser Pro Leu Arg Val Ser Glu Lys Val Leu Leu
            515                 520                 525
```

-continued

```
His Leu Leu Lys His Pro Ser Val Asn Gln Glu Val Thr Phe Asp Glu
    530                 535                 540

Ser Asn Arg Leu Ala Ala His His Tyr Leu Tyr Gln Arg Ser Gln Pro
545                 550                 555                 560

Val Asp Tyr Phe Ile Leu Ile Leu Gln Gly Arg Val Glu Val Glu Ile
                565                 570                 575

Gly Lys Glu Gly Leu Lys Phe Glu Asn Gly Ala Phe Thr Tyr Tyr Gly
            580                 585                 590

Val Ser Ala Leu Thr Ala Pro Ser Ser Ala His Gln Ser Pro Val Ser
        595                 600                 605

Ser Arg Gln Leu Ile Arg His Asp Val Gln Pro Glu Pro Ala Asp Gly
    610                 615                 620

Thr Arg Ser Cys Thr Tyr Cys Pro Asp Tyr Thr Val Arg Ala Leu Ser
625                 630                 635                 640

Asp Leu Gln Leu Ile Lys Val Thr Arg Leu Gln Tyr Leu Asn Ala Leu
                645                 650                 655

Leu Ala Thr Arg Ala Gln Ser Leu Pro Pro Ser Pro Glu Asn Ala Glu
            660                 665                 670

Leu Gln Ala Ile Pro Gly Ser Gln Thr Arg Leu Leu Gly Asp Lys Ser
        675                 680                 685

Arg Thr Ala Gly Ser Thr Asn Ser Arg Pro Ser Ile Pro Val Glu Glu
    690                 695                 700

Ser Pro Gly Arg Asn Pro Gly Val
705                 710
```

<210> SEQ ID NO 16
<211> LENGTH: 771
<212> TYPE: PRT
<213> ORGANISM: Mus musculus

<400> SEQUENCE: 16

```
Met Ala Pro Gly Gly Gly Gly Arg Arg Asp Gly Trp Pro Ala Arg
1               5                   10                  15

Gly Arg Leu Leu Leu Ala Ala Leu Leu Leu Trp Thr Arg Ala Ala
            20                  25                  30

Ser Gly Gln Ser Ser Pro Gln Gln Ser Val Ile Leu Gly Met Arg Leu
        35                  40                  45

Ala Ser Cys Asn Lys Ser Cys Gly Met Asn Pro Asp Gly Ile Ile Phe
    50                  55                  60

Val Ser Glu Gly Ser Thr Val Asn Leu Arg Leu Tyr Gly His Ser Leu
65                  70                  75                  80

Gly Asp Ile Ser Ser Asn Leu Ile Ser Phe Thr Glu Val Asp Asp Ala
                85                  90                  95

Glu Ala Val His Asn Ser Thr Asn Cys Leu Glu Leu Thr Lys Asp Leu
            100                 105                 110

Val Val Gln Arg Leu Val Asn Val Ser Arg Gly Asn Thr Ser Gly Met
        115                 120                 125

Leu Val Val Ile Thr Lys Phe Leu Arg Arg Ser Glu Asn Met Lys Leu
    130                 135                 140

Tyr Ala Leu Cys Thr Arg Pro Arg Ala Asp Gly Pro Trp Thr Arg Trp
145                 150                 155                 160

Thr Asp Lys Asp Ser Leu Leu Phe Met Val Glu Glu His Gly Arg Phe
                165                 170                 175

Leu Pro Leu Trp Leu His Ile Leu Leu Val Met Val Leu Leu Val Leu
```

-continued

```
            180                 185                 190
Ser Gly Ile Phe Ser Gly Leu Asn Leu Gly Leu Met Ala Leu Asp Pro
            195                 200                 205
Met Glu Leu Arg Ile Val Gln Asn Cys Gly Thr Glu Lys Glu Arg Lys
        210                 215                 220
Tyr Ala Arg Lys Ile Glu Pro Ile Arg Arg Lys Gly Asn Tyr Leu Leu
225                 230                 235                 240
Cys Ser Leu Leu Leu Gly Asn Val Leu Val Asn Thr Ser Leu Thr Ile
                    245                 250                 255
Leu Leu Asp Asn Leu Ile Gly Ser Gly Ile Met Ala Val Ala Ser Ser
                260                 265                 270
Thr Ile Gly Ile Val Ile Phe Gly Glu Ile Leu Pro Gln Ala Leu Cys
            275                 280                 285
Ser Arg His Gly Leu Ala Val Gly Ala Asn Thr Ile Val Leu Thr Lys
        290                 295                 300
Val Phe Met Leu Leu Thr Phe Pro Leu Ser Phe Pro Ile Ser Lys Leu
305                 310                 315                 320
Leu Asp Phe Val Leu Gly Gln Glu Ile Arg Thr Val Tyr Asn Arg Glu
                    325                 330                 335
Lys Leu Met Glu Met Leu Lys Val Thr Glu Pro Tyr Asn Asp Leu Val
                340                 345                 350
Lys Glu Glu Leu Asn Met Ile Gln Gly Ala Leu Glu Leu Arg Thr Lys
            355                 360                 365
Thr Val Glu Asp Ile Met Thr Gln Leu His Asp Cys Phe Met Ile Arg
        370                 375                 380
Ser Asp Ala Ile Leu Asp Phe Asn Thr Met Ser Glu Ile Met Glu Ser
385                 390                 395                 400
Gly Tyr Thr Arg Ile Pro Val Phe Glu Asp Glu Gln Ser Asn Ile Val
                    405                 410                 415
Asp Ile Leu Tyr Val Lys Asp Leu Ala Phe Val Asp Pro Asp Asp Cys
                420                 425                 430
Thr Pro Leu Lys Thr Ile Thr Arg Phe Tyr Asn His Pro Val His Phe
            435                 440                 445
Val Phe His Asp Thr Lys Leu Asp Ala Met Leu Glu Glu Phe Lys Lys
        450                 455                 460
Gly Lys Ser His Leu Ala Ile Val Gln Lys Val Asn Asn Glu Gly Glu
465                 470                 475                 480
Gly Asp Pro Phe Tyr Glu Val Leu Gly Leu Val Thr Leu Glu Asp Val
                    485                 490                 495
Ile Glu Glu Ile Ile Lys Ser Glu Ile Leu Asp Glu Ser Asp Met Tyr
                500                 505                 510
Thr Asp Asn Arg Thr Arg Lys Arg Val Ser Val Lys Asn Lys Arg Asp
            515                 520                 525
Phe Ser Ala Phe Lys Asp Thr Asp Asn Glu Leu Lys Val Lys Ile Ser
        530                 535                 540
Pro Gln Leu Leu Leu Ala Ala His Arg Phe Leu Ala Thr Glu Val Pro
545                 550                 555                 560
Gln Phe Ser Pro Ser Leu Met Ser Glu Lys Ile Leu Leu Arg Leu Leu
                    565                 570                 575
Lys Tyr Pro Asp Val Ile Gln Glu Leu Arg Phe Asn Glu His Asn Arg
                580                 585                 590
Tyr Cys Val Arg His Tyr Leu Tyr Thr Arg Asn Lys Pro Ala Asp Cys
            595                 600                 605
```

```
Phe Val Leu Ile Leu Gln Gly Lys Val Glu Val Glu Ala Gly Lys Glu
    610                 615                 620
Asn Met Lys Phe Glu Thr Gly Ala Phe Ser Tyr Tyr Gly Thr Met Ala
625                 630                 635                 640
Leu Ser Val Ala Pro Pro Asp Arg Ser Pro Ala Leu Pro Thr Pro Leu
                645                 650                 655
Ser Arg Ser Ala Ser Leu Ser Tyr Pro Asp Arg Asn Thr Asp Leu Thr
                660                 665                 670
Ser Thr Ser Leu Ala Gly Ser Asn Gln Phe Gly Ser Cys Ile Leu Gly
            675                 680                 685
Gln Tyr Val Ser Asp Phe Ser Val Arg Ala Leu Thr Asp Leu Gln Tyr
        690                 695                 700
Ile Lys Ile Thr Arg Gln Gln Tyr Gln Asn Gly Leu Met Ala Ser Arg
705                 710                 715                 720
Met Asp Asn Ser Pro Gln Pro Thr Phe Asp Gly Cys Ala Thr Cys Ser
                725                 730                 735
Glu Asn Phe Met Glu Arg Pro Glu Leu Pro Pro Val Asp Glu Thr Thr
                740                 745                 750
Thr Leu Leu Asn Glu Arg Asn Ser Leu Leu His Arg Ala Ser Glu Glu
        755                 760                 765
Glu Thr Ile
770
```

ACTIVATORS OF CYCLIN-DEPENDENT KINASES

CROSS-REFERENCE TO RELATED APPLICATIONS

This application claims priority from U.S. provisional patent application Ser. No. 60/306,835 filed Jul. 19, 2001.

STATEMENT AS TO FEDERALLY SPONSORED RESEARCH

This invention was made with United States Government support under grant number 1RO1DK53266-01 awarded by the National Institutes of Health. The United States Government has certain rights in the invention.

FIELD OF THE INVENTION

The invention relates generally to the fields of cell biology and biochemistry. More particularly, the invention relates to proteins and polynucleotides associated with regulation of cell division.

BACKGROUND

The production of two daughter cells from one parent cell is a complex yet elegant process that is essential for the normal growth and maintenance healthy tissue. This process, known as the cell cycle, involves a series of sequential steps termed $G_1$ (gap 1), S (synthesis), $G_2$ (gap 2), and M (mitosis). S phase is characterized by a doubling of a parent cell's chromosomal DNA. In M phase, a cell precisely halves the doubled DNA and then divides itself into two daughter cells in a process termed cytokinesis. $G_1$ is the period following M phase but before S phase during which time the cell prepares for replication of its chromosomal DNA. $G_2$ is the period between S phase and M phase during which the cell prepares for mitosis and cytokinesis.

Several distinct families of cytoplasmic proteins are known to regulate passage of cells through the various phases of the cell cycle. Among the better characterized of these is the cyclin family of proteins. The cyclin family is subdivided into three groups according to the phase of the cell cycle in which they act, i.e., the $G_1$-, S-, and M-phase cyclins. The amount of a particular cyclin expressed by a cell fluctuates through the progression of the cell cycle. For example, $G_1$ cyclin levels rise during the $G_1$ phase and S cyclin levels rise during the S phase.

A second family of cell cycle regulatory proteins is the cyclin-dependent kinase (CDK) family. Proteins in the CDK family are also classified in one of three groups, i.e., $G_1$-, S-, and M-phase CDKs. These proteins are capable of phosphorylating a variety of protein substrates that control various processes at different phases of the cell cycle. Cyclins are also known to physically interact with CDKs in a process that leads to modulatation of CDK kinase activity. For example, M-phase CDK and M-cyclins complex with each other to form an M-phase promoting factor. This factor is instrumental in initiating events leading up to the metaphase stage of mitosis, including assembly of the mitotic spindle, condensation of the chromosomes and breakdown of the nuclear envelope.

A third recognized regulator of the cell cycle is the retinoblastoma protein (pRb). This protein is known as a growth suppressor gene because it can prevent the progression of a cell towards the S phase. Recent research has indicated that pRb plays a major role in regulation of the cell cycle, differentiation, and apoptosis. This protein may cooperate with another protein termed p53 which is known to prevent the division of cells with abnormal DNA and force abnormal cells to self-destruct through apoptosis.

From the foregoing, it is apparent that cell division is an extraordinarily complex and tightly-orchestrated event, with each phase of the cell cycle in itself comprising a complicated series of cellular and molecular events. Unfortunately, many of the molecular bases for these events remain poorly understood. Discovery and characterization of new molecules involved in cell cycle regulation should lead to more complete understanding of this process.

SUMMARY OF THE INVENTION

A new gene family involved in cell cycle regulation has been discovered. This family has been termed activators of cyclin-dependent kinases (ACDKs). A number of ACDK genes have been cloned and sequenced, and the proteins they encode have been characterized structurally and functionally. Structural modeling studies suggested that ACDK proteins are involved in regulating CDK activity. In particular, the energy-minimized structure of ACDK proteins revealed that they possess cyclin-like epitopes. However, ACDK proteins were determined to lack significant sequence homology with cyclins (e.g., no classic cyclin box was present) suggesting that they were a new family of CDK regulators.

ACDKs were also characterized functionally. Binding studies showed that proteins encoded by ACDK genes were able to specifically interact with various CDKs as well as pRb. Phosphorylation assays showed that ACDKs were able to upregulate the kinase activity of a CDK using pRb as a substrate. Utilizing expression vector constructs to express sense and antisense ACDK oligonucleotides in Hela cells, cell cycle analysis showed that significantly more cells were in S phase when ACDK levels were decreased (using the antisense construct) compared to cells with increased levels of ACDK (those with the sense constructs). Taken together, these findings suggested that ACDKs act in concert with CDKs, and pRb to regulate the intracellular signaling events that are involved in cell cycle regulation, particularly in the $S/G_2$ transition.

Protein localization studies showed that ACDK proteins are predominantly localized within the nuclei of cells able to undergo mitosis. Surprisingly, however, in cells that do not undergo mitosis (e.g., terminally differentiated neurons), the ACDK proteins were found to localize in the cytoplasm.

Accordingly, the invention features a purified nucleic acid that includes a nucleotide sequence that encodes a protein that: (a) shares at least 75% (e.g., 80, 90, 95, 99, or 100%) sequence identity with one of SEQ ID NOs:9–16 and (b) has at least one functional activity of a native ACDK protein. This purified nucleic acid of claim 1 can include a polynucleotide whose complement hybridizes under high stringency conditions to one of SEQ ID NOs:1–8. The nucleotide sequence can be one that shares at least 70% (e.g., 80, 90, 95, or 100%) sequence identity with one of SEQ ID NOs: 1–8.

Also within the invention is a vector and a cell that includes one of the foregoing nucleic acids. In the vector, the nucleic acid can be operably linked to one or more expression control sequences, and can also be within a cell. Cells of the invention can be those within an animal (e.g., a mammal such as a human being).

In another aspect, the invention features a purified protein that: (a) shares at least 75% (e.g., 80, 90, 95, 99, or 100%) sequence identity with one of SEQ ID NOs:9–16 and (b) has at least one functional activity of a native ACDK protein. Proteins with the invention can be fused to a heterologous polypeptide, and can be included in a cell, e.g, one within an animal.

The invention further features a purified antibody that specifically binds to the foregoing protein. The antibody can include a detectable label.

The invention also encompasses several methods. For example, a method for detecting an ACDK marker in a biological sample is within the invention. This method includes the step of analyzing the sample for the presence of an ACDK marker, wherein presence of the ACDK marker in the sample indicates that the sample contains the ACDK marker. In some variations of this method, the ACDK marker is an ACDK nucleic acid (e.g., an ACDK mRNA or a native ACDK nucleic acid). The step of analyzing the sample for the presence of an ACDK marker can include contacting the sample with an oligonucleotide probe that hybridizes under stringent hybridization conditions to a polynucleotide having a nucleic acid sequence of one of SEQ ID NOs:1–8 or one of the complements of SEQ ID NOs:1–8. The oligonucleotide probe can include a detectable label. In other variations of this method, the ACDK marker is an ACDK protein, e.g., a native ACDK protein such as one having a sequence of one of SEQ ID NOs:9–16.

Also within the invention is a screening method for identifying a substance that modulates binding of an ACDK protein to a CDK protein. This method includes the steps of: (a) providing an ACDK protein, a CDK protein, and a candidate substance; (b) combining the ACDK protein, the CDK protein, and a candidate substance to form a mixture; (c) placing the mixture under conditions in which the ACDK protein would bind the CDK protein in the absence of the candidate substance; and (d) detecting an increase or decrease in binding of the ACDK protein to CDK protein in the presence of the candidate substance, compared to the binding of the ACDK protein to CDK protein in the absence of the candidate substance, as an indication that the candidate substance modulates binding of the ACDK protein to the CDK protein.

Further featured in the invention is a screening method for identifying a substance that modulates expression of a gene encoding an ACDK protein. This method includes the steps of: (a) providing a test cell; (b) contacting the test cell with a candidate substance; and (c) detecting an increase or decrease in the expression level of the gene encoding the ACDK protein in the presence of the candidate substance, compared to the expression level of the gene encoding the ACDK protein in the absence of the candidate substance, as an indication that the candidate substance modulates the level of expression of the gene encoding the ACDK protein.

Another method within the invention is one for isolating a substance that binds an ACDK protein (e.g., a CDK protein). This method includes the steps of: (a) providing a sample of an immobilized ACDK protein; (b) contacting a mixture containing the ACDK protein-binding substance with the immobilized ACDK protein; (c) separating unbound components of the mixture from bound components of the mixture; and (d) recovering the ACDK protein-binding substance from the immobilized ACDK protein.

The invention also includes a method of modulating ACDK gene expression. This method includes the steps of: (a) providing a cell that expresses an ACDK gene; and (b) introducing into the cell an agent that modulates the expression of the ACDK gene in the cell. The agent can be an oligonucleotide such as an antisense oligonucleotide, e.g., one that hybridizes under stringent hybridization conditions to a polynucleotide that encodes a protein having a sequence of one of SEQ ID NOs: 9–16. The antisense oligonucleotide can also be one that is at least 18 nucleotides in length and includes a sequence that is a complement of a nucleic acid that encodes a native ACDK protein such as one having a sequence of one of SEQ ID NOs:1–8.

As the ACDK proteins of the invention are involved in cell-cycle regulation, the invention additionally includes a method for modulating mitosis in a cell. This method includes the step of contacting the cell with an agent that modulates expression of an ACDK protein in the cell. The agent can be an oligonucleotide such as an antisense oligonucleotide, e.g., one that hybridizes under stringent hybridization conditions to a polynucleotide that encodes a protein having a sequence of one of SEQ ID NOs: 9–16. The antisense oligonucleotide can also be one that is at least 18 nucleotides in length and includes a sequence that is a complement of a nucleic acid that encodes a native ACDK protein such as one having a sequence of one of SEQ ID NOs:1–8. The cell can be one in an animal.

Unless otherwise defined, all technical terms used herein have the same meaning as commonly understood by one of ordinary skill in the art to which this invention belongs. Commonly understood definitions of molecular biology terms can be found in Rieger et al., Glossary of Genetics: Classical and Molecular, 5th edition, Springer-Verlag: New York, 1991; and Lewin, Genes V, Oxford University Press: New York, 1994.

By the term "gene" is meant a nucleic acid molecule that codes for a particular protein, or in certain cases, a functional or structural RNA molecule. For example, an ACDK gene encodes an ACDK protein.

As used herein, a "nucleic acid" or a "nucleic acid molecule" means a chain of two or more nucleotides such as RNA (ribonucleic acid) and DNA (deoxyribonucleic acid). A "purified" nucleic acid molecule is one that has been substantially separated or isolated away from other nucleic acid sequences in a cell or organism in which the nucleic acid naturally occurs (e.g., 30, 40, 50, 60, 70, 80, 90, 95, 96, 97, 98, 99, 100% free of contaminants). The term includes, e.g., a recombinant nucleic acid molecule incorporated into a vector, a plasmid, a virus, or a genome of a prokaryote or eukaryote. Examples of purified nucleic acids include cDNAs, fragments of genomic nucleic acids, nucleic acids produced polymerase chain reaction (PCR), nucleic acids formed by restriction enzyme treatment of genomic nucleic acids, recombinant nucleic acids, and chemically synthesized nucleic acid molecules. A "recombinant" nucleic acid molecule is one made by an artificial combination of two otherwise separated segments of sequence, e.g., by chemical synthesis or by the manipulation of isolated segments of nucleic acids by genetic engineering techniques.

By the terms "ACDK gene," "ACDK polynucleotide," or "ACDK nucleic acid" is meant a native ACDK-encoding nucleic acid sequence, e.g., one of a native ACDK cDNAs SEQ ID NOs:1–8); a nucleic acid having sequences from which an ACDK cDNA can be transcribed; and/or allelic variants and homologs of the foregoing. The terms encompass double-stranded DNA, single-stranded DNA, and RNA.

As used herein, "protein" or "polypeptide" are used synonymously to mean any peptide-linked chain of amino acids, regardless of length or post-translational modification, e.g., glycosylation or phosphorylation. An "purified"

polypeptide is one that has been substantially separated or isolated away from other polypeptides in a cell or organism in which the polypeptide naturally occurs (e.g., 30, 40, 50, 60, 70, 80, 90, 95, 96, 97, 98, 99, 100% free of contaminants).

By the terms "ACDK protein" or "ACDK polypeptide" is meant an expression product of an ACDK gene such as one of a native ACDK proteins of SEQ ID NOs:9–16 or a protein that shares at least 65% (but preferably 75, 80, 85, 90, 95, 96, 97, 98, or 99%) amino acid sequence identity with one of the proteins of SEQ ID NOs:9–16 and displays a functional activity of an ACDK protein. A "functional activity" of a protein is any activity associated with the physiological function of the protein. For example, functional activities of ACDKs may include regulation of the cell cycle, specific binding to a CDK, or contributing to the phosphorylation of a substrate such as pRb.

When referring to a nucleic acid molecule or polypeptide, the term "native" refers to a naturally-occurring (e.g., a "wild-type") nucleic acid or polypeptide. A "homolog" of an ACDK gene is a gene sequence encoding an ACDK polypeptide isolated from an organism other than the animal from which a native gene was isolated. Similarly, a "homolog" of a native ACDK polypeptide is an expression product of an ACDK homolog.

A "fragment" of an ACDK nucleic acid is a portion of an ACDK nucleic acid that is less than full-length and comprises at least a minimum length capable of hybridizing specifically with a native ACDK nucleic acid under stringent hybridization conditions. The length of such a fragment is preferably at least 15 nucleotides, more preferably at least 20 nucleotides, and most preferably at least 30 nucleotides of a native ACDK nucleic acid sequence. A "fragment" of an ACDK polypeptide is a portion of an ACDK polypeptide that is less than full-length (e.g., a polypeptide consisting of 5, 10, 15, 20, 30, 40, 50, 75, 100 or more amino acids of native ACDK polypeptide), and preferably retains at least one functional activity of a native ACDK polypeptide.

When referring to hybridization of one nucleic to another, "low stringency conditions" means in 10% formamide, 5× Denhart's solution, 6×SSPE, 0.2% SDS at 42° C., followed by washing in 1×SSPE, 0.2% SDS, at 50° C.; "moderate stringency conditions" means in 50% formamide, 5× Denhart's solution, 5×SSPE, 0.2% SDS at 42° C., followed by washing in 0.2×SSPE, 0.2% SDS, at 65° C.; and "high stringency conditions" means in 50% formamide, 5× Denhart's solution, 5×SSPE, 0.2% SDS at 42° C., followed by washing in 0.1×SSPE, and 0.1% SDS at 65° C. The phrase "stringent hybridization conditions" means low, moderate, or high stringency conditions.

As used herein, "sequence identity" means the percentage of identical subunits at corresponding positions in two sequences when the two sequences are aligned to maximize subunit matching, i.e., taking into account gaps and insertions. When a subunit position in both of the two sequences is occupied by the same monomeric subunit, e.g., if a given position is occupied by an adenine in each of two DNA molecules, then the molecules are identical at that position. For example, if 7 positions in a sequence 10 nucleotides in length are identical to the corresponding positions in a second 10-nucleotide sequence, then the two sequences have 70% sequence identity. As another example, if 12 positions in a protein sequence 20 amino acids in length are identical to the corresponding positions in a second 20-amino acid sequence, then the two sequences have 60% sequence identity. Preferably, the length of the compared nucleic acid sequences is at least 60 nucleotides, more preferably at least 75 nucleotides, and most preferably 100 nucleotides; and the length of compared polypeptide sequences is at least 15, 25, and 50 amino acids. Sequence identity is typically measured using sequence analysis software (e.g., Sequence Analysis Software Package of the Genetics Computer Group, University of Wisconsin Biotechnology Center, 1710 University Avenue, Madison, Wis. 53705).

When referring to mutations in a nucleic acid molecule, "silent" changes are those that substitute of one or more base pairs in the nucleotide sequence, but do not change the amino acid sequence of the polypeptide encoded by the sequence. "Conservative" changes are those in which at least one codon in the protein-coding region of the nucleic acid has been changed such that at least one amino acid of the polypeptide encoded by the nucleic acid sequence is substituted with another amino acid having similar characteristics. Examples of conservative amino acid substitutions are ser for ala, thr, or cys; lys for arg; gln for asn, his, or lys; his for asn; glu for asp or lys; asn for his or gln; asp for glu; pro for gly; leu for ile, phe, met, or val; val for ile or leu; ile for leu, met, or val; arg for lys; met for phe; tyr for phe or trp; thr for ser; trp for tyr; and phe for tyr.

As used herein, the term "vector" refers to a nucleic acid molecule capable of transporting another nucleic acid to which it has been linked. One type of preferred vector is an episome, i.e., a nucleic acid capable of extra-chromosomal replication. Preferred vectors are those capable of autonomous replication and/expression of nucleic acids to which they are linked. Vectors capable of directing the expression of genes to which they are operatively linked are referred to herein as "expression vectors."

A first nucleic acid sequence is "operably" linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked nucleic acid sequences are contiguous and, where necessary to join two protein coding regions, in reading frame.

A cell, tissue, or organism into which has been introduced a foreign nucleic acid, such as a recombinant vector, is considered "transformed," "transfected," or "transgenic." A "transgenic" or "transformed" cell or organism (e.g., a mammal) also includes progeny of the cell or organism. For example, an organism transgenic for ACDK is one in which an ACDK nucleic acid has been introduced.

By the term "ACDK-specific antibody" is meant an antibody that binds an ACDK protein, and displays no substantial binding to other naturally occurring proteins other than those sharing the same antigenic determinants as an ACDK protein. The term includes polyclonal and monoclonal antibodies.

As used herein, "bind," "binds," or "interacts with" means that one molecule recognizes and adheres to a particular second molecule in a sample, but does not substantially recognize or adhere to other structurally unrelated molecules in the sample. Generally, a first molecule that "specifically binds" a second molecule has a binding affinity greater than about $10^5$ to $10^6$ moles/liter for that second molecule.

The term "labeled," with regard to a probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin.

Although methods and materials similar or equivalent to those described herein can be used in the practice or testing of the present invention, suitable methods and materials are described below. All publications, patent applications, patents, and other references mentioned herein are incorporated by reference in their entirety. In the case of conflict, the present specification, including definitions will control. In addition, the particular embodiments discussed below are illustrative only and not intended to be limiting.

BRIEF DESCRIPTION OF THE DRAWINGS

The invention is pointed out with particularity in the appended claims. The above and the further advantages of this invention may be better understood by referring to the following description taken in conjunction with the accompanying drawings, in which:

FIG. 1 is a multiple sequence alignment showing the ACDK conserved domain in various species. DroM is *Drosophila melanogaster* hypothetical protein, the accession number is AE002742. SSC is SCDNACHXV *Saccharomyces cerevisiae* hypothetical protein, the accession number for this proteins is X91067. CanG represents *Candida Glabrata* hypothetical protein, the accession number for this protein is AF196836. SCHP represents *Schizosaccharomyces pombe* hypothetical protein (D89137), while PM70 represents hypothetical protein from *Pasteurella multocida* (AE006144). HaeI represents *Haemophilus influenzae* hypothetical protein (U32716). PA01 is *Pseudomonas aeruginosa* hypothetical protein (AE004948), and CaeE represents hypothetical protein from the *Caenorhabditis elegans*, the accession number for this protein is AC006622.

DETAILED DESCRIPTION

Figure 2:
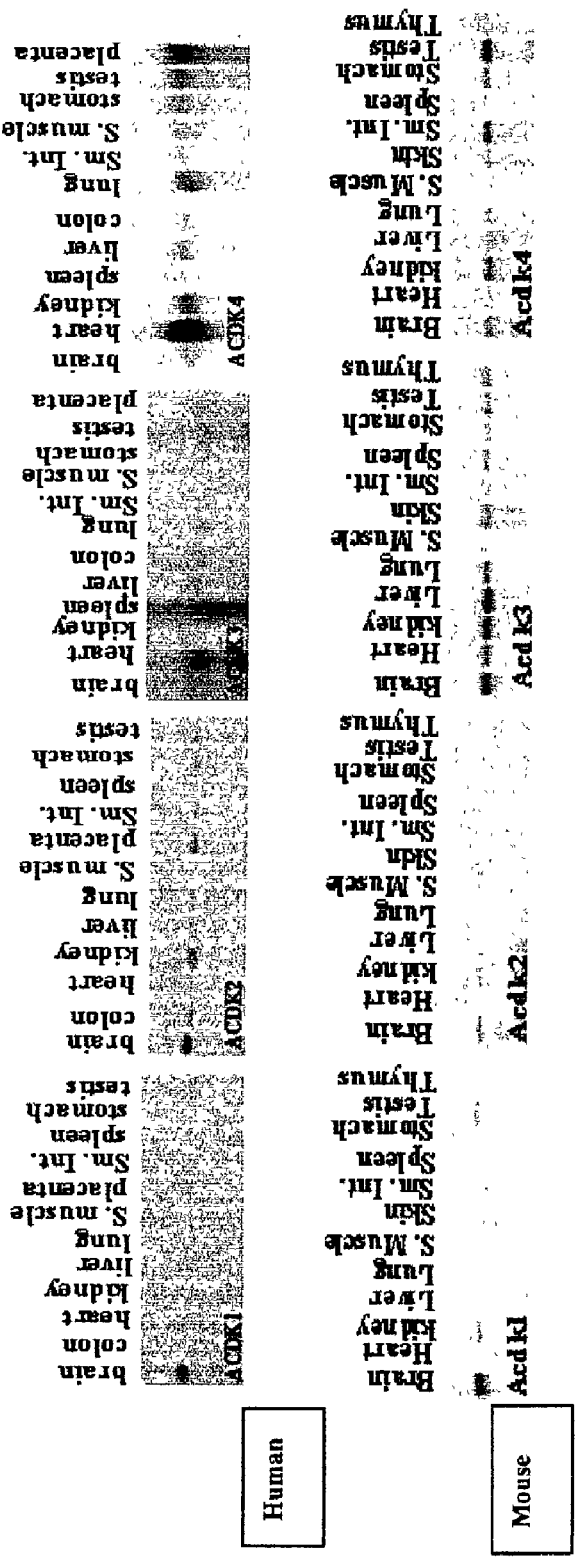
FIG. 2 is an expression analysis of the human ACDK gene family and its mouse homologue. S. muscle represents skeletal muscle, Sm. Int. represents small intestine. Multiple Choice Northern Blot filters were purchased from Origene (HB-2010 and MB-2010).

The invention encompasses compositions and methods relating to the ACDK family of proteins. The below described preferred embodiments illustrate adaptations of these compositions and methods. Nonetheless, from the description of these embodiments, other aspects of the invention can be made and/or practiced based on the description provided below.

Biological Methods

Methods involving conventional molecular biology techniques are described herein. Such techniques are generally known in the art and are described in detail in methodology treatises such as Molecular Cloning: A Laboratory Manual, 2nd ed., vol. 1–3, ed. Sambrook et al., Cold Spring Harbor Laboratory Press, Cold Spring Harbor, N.Y., 1989; and Current Protocols in Molecular Biology, ed. Ausubel et al., Greene Publishing and Wiley-Interscience, New York, 1992 (with periodic updates). Various techniques using polymerase chain reaction (PCR) are described, e.g., in Innis et al., PCR Protocols: A Guide to Methods and Applications, Academic Press: San Diego, 1990. PCR-primer pairs can be derived from known sequences by known techniques such as using computer programs intended for that purpose (e.g., Primer, Version 0.5, 1991, Whitehead Institute for Biomedical Research, Cambridge, Mass.). Methods for chemical synthesis of nucleic acids are discussed, for example, in Beaucage and Carruthers, Tetra. Letts. 22:1859–1862, 1981, and Matteucci et al., J. Am. Chem. Soc. 103:3185, 1981. Chemical synthesis of nucleic acids can be performed, for example, on commercial automated oligonucleotide synthesizers. Immunological methods (e.g., preparation of antigen-specific antibodies, immunoprecipitation, and immunoblotting) are described, e.g., in Current Protocols in Immunology, ed. Coligan et al., John Wiley & Sons, New York, 1991; and Methods of Immunological Analysis, ed. Masseyeff et al., John Wiley & Sons, New York, 1992. Conventional methods of gene transfer and gene therapy can also be adapted for use in the present invention. See, e.g., Gene Therapy: Principles and Applications, ed. T. Blackenstein, Springer Verlag, 1999; Gene Therapy Protocols (Methods in Molecular Medicine), ed. P. D. Robbins, Humana Press, 1997; and Retro-vectors for Human Gene Therapy, ed. C. P. Hodgson, Springer Verlag, 1996.

Nucleic Acids Encoding ACDK

The present invention utilizes ACDK genes, several of which have now been cloned and sequenced. A preferred nucleic acid molecule of for use in the invention is one of the native ACDK polynucleotides listed as SEQ ID NOs:1–8. Another nucleic acid that can be used in various aspects of the invention includes a purified nucleic acid (polynucleotide) that encodes a polypeptide having the amino acid sequence of one of the proteins listed as SEQ ID NOs:9–16.

Nucleic acid molecules utilized in the present invention may be in the form of RNA or in the form of DNA (e.g., cDNA, genomic DNA, and synthetic DNA). The DNA may be double-stranded or single-stranded, and if single-stranded may be the coding (sense) strand or non-coding (anti-sense) strand. The coding sequence which encodes a native ACDK protein may be identical to one of the nucleotide sequences listed as SEQ ID NOs:1–8. It may also be a different coding sequence which, as a result of the redundancy or degeneracy of the genetic code, encodes the same polypeptide as one of these polynucleotides.

Other nucleic acid molecules within the invention are variants of a native ACDK gene such as those that encode fragments (e.g., post-translationally processed forms of), analogs and derivatives of a native ACDK protein. Such variants may be, e.g., a naturally occurring allelic variant of a native ACDK gene, a homolog of a native ACDK gene, or a non-naturally occurring variant of a native ACDK gene. These variants have a nucleotide sequence that differs from a native ACDK gene in one or more bases. For example, the nucleotide sequence of such variants can feature a deletion, addition, or substitution of one or more nucleotides of a native ACDK gene. Nucleic acid insertions are preferably of about 1 to 10 contiguous nucleotides, and deletions are preferably of about 1 to 30 contiguous nucleotides.

In other applications, variant ACDK proteins displaying substantial changes in structure can be generated by making nucleotide substitutions that cause less than conservative changes in the encoded polypeptide. Examples of such nucleotide substitutions are those that cause changes in (a) the structure of the polypeptide backbone; (b) the charge or hydrophobicity of the polypeptide; or (c) the bulk of an amino acid side chain. Nucleotide substitutions generally expected to produce the greatest changes in protein properties are those that cause non-conservative changes in codons. Examples of codon changes that are likely to cause major changes in protein structure are those that cause substitution of (a) a hydrophilic residue, e.g., serine or threonine, for (or by) a hydrophobic residue, e.g., leucine, isoleucine, phenylalanine, valine or alanine; (b) a cysteine or proline for (or by) any other residue; (c) a residue having an electropositive side chain, e.g., lysine, arginine, or histadine, for (or by) an electronegative residue, e.g., glutamine or aspartine; or (d) a residue having a bulky side chain, e.g., phenylalanine, for (or by) one not having a side chain, e.g., glycine.

Naturally occurring allelic variants of a native ACDK gene within the invention are nucleic acids isolated from human or murine tissue that have at least 75% (e.g., 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, and 99%) sequence identity with a native ACDK gene, and encode polypeptides having structural similarity to native ACDK protein. Homologs of a native ACDK gene within the invention are nucleic acids isolated from other species that have at least 75% (e.g., 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, and 99%) sequence identity with a native ACDK gene, and encode polypeptides having structural similarity to native ACDK protein. Public and/or proprietary nucleic acid databases can be searched in an attempt to identify other nucleic acid molecules having a high percent (e.g., 70, 80, 90% or more) sequence identity to a native ACDK gene.

Non-naturally occurring ACDK gene variants are nucleic acids that do not occur in nature (e.g., are made by the hand of man), have at least 75% (e.g., 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, and 99%) sequence identity with a native ACDK gene, and encode polypeptides having structural similarity to native ACDK protein. Examples of non-naturally occurring ACDK gene variants are those that encode a fragment of an ACDK protein, those that hybridize to a native ACDK gene or a complement of to a native ACDK gene under stringent conditions, those that share at least 65% (e.g., 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, and 99%) sequence identity with a native ACDK gene or a complement of a native ACDK gene, and those that encode an ACDK fusion protein.

Nucleic acids encoding fragments of native ACDK protein within the invention are those that encode, e.g., 2, 5, 10, 25, 30, 40, 50, 60, 70, 80, 90, 100, or more amino acid residues of a native ACDK protein. Shorter oligonucleotides (e.g., those of 6, 7, 8, 9, 10, 11, 12, 13, 14, 15, 16, 17, 18, 19, 20, 30, 50, 100, base pairs in length) that encode or hybridize with nucleic acids that encode fragments of a native ACDK protein can be used as probes, primers, or antisense molecules. Longer polynucleotides (e.g., those of 125, 150, 175, 200, 225, 250, 275, 300, or more base pairs) that encode or hybridize with nucleic acids that encode fragments of native ACDK protein can also be used in various aspects of the invention. Nucleic acids encoding fragments of native ACDK protein can be made by enzymatic digestion (e.g., using a restriction enzyme) or chemical degradation of the full length native ACDK gene or variants thereof.

Nucleic acids that hybridize under stringent conditions to a nucleic acid selected from SEQ ID NOs:1–8 or a complement of SEQ ID NOs:1–8 can also be used in the invention. For example, such nucleic acids can be those that hybridize to one of SEQ ID NOs:1–8 or the complement of SEQ ID NOs:1–8 under low stringency conditions, moderate stringency conditions, or high stringency conditions. Preferred such nucleotide acids are those having a nucleotide sequence that is the complement of all or a portion of one of SEQ ID NOs:1–8.

Nucleic acid molecules encoding ACDK fusion proteins are also within the invention. Such nucleic acids can be made by preparing a construct (e.g., an expression vector) that expresses an ACDK fusion protein when introduced into a suitable host. For example, such a construct can be made by ligating a first polynucleotide encoding an ACDK protein fused in frame with a second polynucleotide encoding another protein (e.g., a detectable label or affinity tag) such that expression of the construct in a suitable expression system yields a fusion protein.

The nucleic acids of the invention can be modified at the base moiety, sugar moiety, or phosphate backbone, for example, to improve stability of the molecule, hybridization, etc. The nucleic acids within the invention may additionally include other appended groups such as peptides (e.g., for targeting host cell receptors in vivo), or agents facilitating transport across the cell membrane (see, e.g., Letsinger et al. (1989) Proc. Natl. Acad. Sci. U.S.A. 86:6553–6556; Lemaitre et al. (1987) Proc. Natl. Acad. Sci. USA 84:648–652; PCT Publication No. WO 88/09810, published Dec. 15, 1988), hybridization-triggered cleavage agents. (See, e.g., Krol et al. (1988) BioTechniques 6:958–976) or intercalating agents. (See, e.g, Zon (1988) Pharm. Res. 5:539–549).

Vectors for Expressing ACDK

Natural or synthetic nucleic acids according to the present invention can be incorporated into recombinant nucleic acid constructs, typically DNA constructs, capable of introduction into and replication in a host cell. Such a construct preferably is a vector that includes a replication system and sequences that are capable of transcription and translation of a polypeptide-encoding sequence in a given host cell. For the present invention, conventional compositions and methods for preparing and using vectors and host cells can be employed, as described, e.g., in Sambrook et al., supra, or Ausubel et al., supra.

Expression of an ACDK gene in a host cell (e.g., one in an animal) is achieved by introducing into the host cell a nucleic acid sequence containing an ACDK gene encoding an ACDK polypeptide. An "expression vector" is a vector capable of expressing a DNA (or cDNA) molecule cloned into the vector and, in certain cases, producing a polypeptide or protein. Appropriate transcriptional and/or translational control sequences are included in the vector to allow it to be expressed in a cell. Expression of the cloned sequences occurs when the expression vector is introduced into an appropriate host cell. If a prokaryotic expression vector is employed, then the appropriate host cell would be any prokaryotic cell capable of expressing the cloned sequences. Similarly, if a eukaryotic expression vector is employed, then the appropriate host cell would be any eukaryotic cell capable of expressing the cloned sequences. A number of vectors suitable for stable transformation of animal cells or for the establishment of transgenic animals are known. See, e.g., Pouwels et al., Cloning Vectors: A Laboratory Manual, 1985, Supp. 1987.

The precise nature of regulatory regions needed for gene expression may vary from organism to organism, but in general include a promoter which directs the initiation of RNA transcription. Such regions may include those 5'-non-coding sequences involved with initiation of transcription such as the TATA box. The promoter may be constitutive or regulatable. Constitutive promoters are those which cause an operably linked gene to be expressed essentially at all times. Regulatable promoters are those which can be activated or deactivated. Regulatable promoters include inducible promoters, which are usually "off" but which may be induced to turn "on", and "repressible" promoters, which are usually "on" but may be turned "off." Many different regulatable promoters are known, including those regulated by temperature, hormones, heavy metals, the product of the natively lined gene, and regulatory proteins. These distinctions are not absolute; a constitutive promoter may be regulatable to some degree.

The regulatability of a promoter may be associated with a particular genetic element, often called an "operator", to which an inducer or repressor binds. The operator may be modified to alter its regulation. Hybrid promoters may be constructed in which the operator of one promoter is transferred into another.

The promoter may be an "ubiquitous" promoter active in essentially all cells of the host organism, e.g., the beta-actin or optomegalovirus promoters, or it may be a promoter whose expression is more or less specific to the target cells. Preferably, the tissue-specific promoters are essentially not active outside a given tissue type, and the activity of the promoter optionally may be higher in some components of the tissue type than in others.

Typically, animal expression vectors include (1) one or more cloned animal genes under the transcriptional control of 5' and 3' regulatory sequences and (2) a dominant selectable marker. Such animal expression vectors may also contain, if desired, a promoter regulatory region (e.g., a regulatory region controlling inducible or constitutive, environmentally- or developmentally-regulated, or cell- or tissue-specific expression), a transcription initiation start site, a ribosome binding site, an RNA processing signal, a transcription termination site, and/or a polyadenylation signal.

An example of a useful promoter which could be used to express a gene according to the invention is a cytomegalovirus (CMV) immediate early promoter (CMV IE) (Xu et al., Gene 272: 149–156, 2001). These promoters confer high levels of expression in most animal tissues, and are generally not dependent on the particular encoded proteins to be expressed. In most tissues of transgenic animals, the CMV IE promoter is a strong promoter. Other promoters that may be useful in the invention may include Rous sarcoma virus promoter, Adenovirus major late promoter (MLP), Herpes Simplex Virus promoter, Mouse mammary tumor virus LTR promoter, HIV long terminal repeat (LTR) promoter, beta actin promoter (Genbank # K00790), or murine metallothionein promoter (Stratagene San Diego Calif.). Synthetic promoters, hybrid promoters, and the like are also useful in the invention and are known in the art.

Animal expression vectors may also include RNA processing signals such as introns, which have been shown to increase gene expression. Yu et al. (2002) 81: 155–163 and Gough et al. (2001) Immunology 103: 351–361. The location of the RNA splice sequences can influence the level of transgene expression in animals. In view of this fact, an intron may be positioned upstream or downstream of an ACDK polypeptide-encoding sequence in the transgene to modulate levels of gene expression.

Expression vectors within the invention may also include regulatory control regions which are generally present in the 3' regions of animal genes. See, e.g., Jacobson et al. (1996) Annu. Rev. Biochem. 65:693–739; and Rajagopalan et al., (1997) Prog. Nucleic Acid Res. Mol. Biol. 56:257–286. For example, a 3' terminator region may be included in the expression vector to increase stability of the mRNA.

Animal expression vectors within the invention preferably contain a selectable marker gene used to identify the cells that have become transformed. Suitable selectable marker genes for animal systems include genes encoding enzymes that produce antibiotic resistance (e.g., those conferring resistance to hygromycin, kanamycin, bleomycin, G418, streptomycin).

Cells Transformed with ACDK

Upon construction of the expression vector, several standard methods are known for introduction of the recombinant genetic material into the host animal for the generation of a transgenic animal. Examples of such methods include (1) the particle delivery system (See e.g., Novakovic S et al. (1999) J Exp Clin Cancer Res 18:531–6; Tanigawa et al. (2000) Cancer Immunol Immunother 48:635–43; or BioRad Technical Bulletin 1687, supra), (2) microinjection protocols (See, e.g., Krisher et al. (1994) Transgenic Res. 3: 226–231; Robinett C C and Dunaway M (1999) Modeling transcriptional regulation using microinjection into *Xenopus* oocytes. In, Methods: A Companion to Methods in Enzymology 17: 151–160; or Pinkert C A and Trounce I A (2002) Methods 26:348–57), (3) polyethylene glycol (PEG) procedures (See e.g., Meyer O et al. (1998) J Biol Chem 273: 15621–7; or Park et al. (2002) Bioconj Chem, 13: 232–239), (4) liposome-mediated DNA uptake (See, e.g., Hofland H E J and Sullivan S M (1997) J. Liposome Res. 7: 187–205; or Hui S W et al. (1996) Biophys. J. 71:590–599), (5) electroporation protocols (See e.g., Dev S B and Hofmann G A (1996) Clinical Applications of Electroporation. In: Lynch P T, Davey M R (Eds): Electrical Manipulation of Cells. Chapman & Hall, New York: 185–199). In one example, animal cells may be transformed by shooting into the cell tungsten microprojectiles on which cloned DNA is precipitated. In the Biolistic Apparatus (Bio-Rad, Hercules, Calif.) used for the shooting, a gunpowder charge (.22 caliber Power Piston Tool Charge) or an air-driven blast drives a plastic macroprojectile through a gun barrel. An aliquot of a suspension of tungsten particles on which DNA has been precipitated is placed on the front of the plastic macroprojectile. The latter is fired at an acrylic stopping plate that has a hole through it that is too small for the macroprojectile to go through. As a result, the plastic macroprojectile smashes against the stopping plate and the tungsten microprojectiles continue toward their target through the hole in the plate. For the instant invention, the target can be any animal cell, tissue, seed, or embryo.

Transgenic Animals

Transgenic animals within the invention can be made by regenerating animal cells transformed with a animal expression vector by standard animal tissue culture techniques. The polypeptides of the invention can be expressed in humans and non-human transgenic animals including but not limited to mice, rats, rabbits, guinea pigs, micro-pigs, goats, sheep, pigs, non-human primates (e.g. baboons, monkeys, and chimpanzees). See e.g., Hammer et al. (1985) Nature 315: 680–683; Palmiter et al. (1983) Science 222:809–814; Brinster et al. (1985) Proc Natl. Acad. Sci USA 82:4438–4442; Palmiter and Brinster (1985) Cell. 41:343–345; and U.S. Pat. No. 4,736,866. Procedures known in the art may be used to introduce a nucleic acid molecule of the invention encoding an ACDK polypeptide into animals to produce the founder lines of transgenic animals. Such procedures include pronuclear microinjection, retrovirus mediated gene transfer into germ lines, gene targeting in embryonic stem cells, electroporation of embryos, and sperm-mediated gene transfer.

The present invention contemplates a transgenic animal that carries one or more ACDK genes in all their cells, and animals which carry the transgene in some but not all their cells. The transgene may be integrated as a single transgene or in concatamers. The transgene may be selectively introduced into and activated in specific cell types. See e.g., Lasko et al, 1992 Proc. Natl. Acad. Sci. USA 89: 6236. The transgene may be integrated into the chromosomal site of the endogenous gene by gene targeting. The transgene may be selectively introduced into a particular cell type inactivating the endogenous gene in that cell type. See e.g., Gu et al Science 265: 103–106.

The expression of a recombinant ACDK polypeptide, or an in a transgenic animal may be assayed using standard techniques. Initial screening may be conducted by Southern Blot analysis, or PCR methods to analyze whether the transgene has been integrated. The level of mRNA expression in the tissues of transgenic animals may also be assessed using techniques including Northern blot analysis of tissue samples, in situ hybridization, and RT-PCR. Tissues may also be evaluated immunocytochemically using antibodies against an ACDK of the invention.

Transgenic lines are evaluated for levels of transgene expression. Expression at the RNA level is determined initially to identify and quantitate expression-positive animals. Standard techniques for RNA analysis are employed and include PCR amplification assays using oligonucleotide primers designed to amplify only transgene RNA templates and solution hybridization assays using transgene-specific probes. See, e.g., Ausubel et al., supra. The RNA-positive animals are then analyzed for protein expression by Western immunoblot analysis using ACDK polypeptide-specific antibodies. See e.g. Ausubel et al., supra. In addition, in situ hybridization and immunocytochemistry according to standard protocols can be done using transgene-specific nucleotide probes and antibodies, respectively, to localize sites of expression within transgenic tissue.

Antisense, Ribozyme, Triplex Techniques

Another aspect of the invention relates to the use of purified antisense nucleic acids to inhibit expression of ACDK. Antisense nucleic acid molecules within the invention are those that specifically hybridize (e.g. bind) under cellular conditions to cellular mRNA and/or genomic DNA encoding an ACDK protein in a manner that inhibits expression of the ACDK protein, e.g., by inhibiting transcription and/or translation. The binding may be by conventional base pair complementarity, or, for example, in the case of binding to DNA duplexes, through specific interactions in the major groove of the double helix.

Antisense constructs can be delivered, for example, as an expression plasmid which, when transcribed in the cell, produces RNA which is complementary to at least a unique portion of the cellular mRNA which encodes an ACDK protein. Alternatively, the antisense construct can take the form of an oligonucleotide probe generated ex vivo which, when introduced into an ACDK protein expressing cell, causes inhibition of the ACDK protein expression by hybridizing with an mRNA and/or genomic sequences coding for ACDK protein. Such oligonucleotide probes are preferably modified oligonucleotides that are resistant to endogenous nucleases, e.g. exonucleases and/or endonucleases, and are therefore stable in vivo. Exemplary nucleic acid molecules for use as antisense oligonucleotides are phosphoramidate, phosphothioate and methylphosphonate analogs of DNA (see, e.g., U.S. Pat. Nos. 5,176,996; 5,264,564; and 5,256, 775). Additionally, general approaches to constructing oligomers useful in antisense therapy have been reviewed, for example, by Van der Krol et al. (1988) Biotechniques 6:958–976; and Stein et al. (1988) Cancer Res 48:2659–2668. With respect to antisense DNA, oligodeoxyribonucleotides derived from the translation initiation site, e.g., between the −10 and +10 regions of an ACDK protein encoding nucleotide sequence, are preferred.

Antisense approaches involve the design of oligonucleotides (either DNA or RNA) that are complementary to an ACDK mRNA. The antisense oligonucleotides will bind to ACDK mRNA transcripts and prevent translation. Absolute complementarity, although preferred, is not required. The ability to hybridize will depend on both the degree of complementarity and the length of the antisense nucleic acid. Generally, the longer the hybridizing nucleic acid, the more base mismatches with an RNA it may contain and still form a stable duplex (or triplex, as the case may be). One skilled in the art can ascertain a tolerable degree of mismatch by use of standard procedures to determine the melting point of the hybridized complex.

Oligonucleotides that are complementary to the 5' end of the message, e.g., the 5' untranslated sequence up to and including the AUG initiation codon, should work most efficiently at inhibiting translation. However, sequences complementary to the 3' untranslated sequences of mRNAs have been shown to be effective at inhibiting translation of mRNAs as well. (Wagner, R. (1994) Nature 372:333). Therefore, oligonucleotides complementary to either the 5' or 3' untranslated, non-coding regions of an ACDK gene could be used in an antisense approach to inhibit translation of an endogenous ACDK mRNA. Oligonucleotides complementary to the 5' untranslated region of the mRNA should include the complement of the AUG start codon. Antisense oligonucleotides complementary to mRNA coding regions are less efficient inhibitors of translation but could be used in accordance with the invention. Whether designed to hybridize to the 5', 3' or coding region of an ACDK mRNA, antisense nucleic acids should be at least eighteen nucleotides in length (e.g., 18, 20, 25, 30, 35, 40, 45, 50, 60, 70, 80, 90 nucleotides in length), and are preferably less than about 100 nucleotides in length.

Regardless of the choice of target sequence, it is preferred that in vitro studies are first performed to quantitate the ability of the antisense oligonucleotide to inhibit gene expression. It is preferred that these studies utilize controls that distinguish between antisense gene inhibition and non-specific biological effects of oligonucleotides. It is also preferred that these studies compare levels of the target RNA or protein with that of an internal control RNA or protein. Additionally, it is envisioned that results obtained using the antisense oligonucleotide are compared with those obtained using a control oligonucleotide. It is preferred that the control oligonucleotide is of approximately the same length as the test oligonucleotide and that the nucleotide sequence of the oligonucleotide differs from the antisense sequence no more than is necessary to prevent specific hybridization to the target sequence.

Antisense oligonucleotides of the invention may comprise at least one modified base moiety which is selected from the group including but not limited to 5-fluorouracil, 5-bromouracil, 5-chlorouracil, 5-iodouracil, hypoxanthine, xanthine, 4-acetylcytosine, 5-(carboxyhydroxyethyl) uracil, 5-carboxymethylaminomethyl-2-thiouridine, 5-carboxymethylaminomethyluracil, dihydrouricil, beta-D-galactosylqueosine, inosine, N6-isopentenyladenine, 1-methylguanine, 1-methylinosine, 2,2-idimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N-6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine. Antisense oligonucleotides of the invention may also comprise at least one modified sugar moiety selected from the group including but not limited to arabinose, 2-fluoroarabinose, xylulose, and hexose; and may additionally include at least one modified phosphate backbone selected from the group consisting of a phosphorothioate, a phosphorodithioate, a phosphoramidothioate, a phosphoramidate, a phosphordiamidate, a methylphosphonate, an alkyl phosphotriester, and a formacetal or analog thereof.

In yet a further embodiment, the antisense oligonucleotide is an alpha-anomeric oligonucleotide. An alpha-anomeric oligonucleotide forms specific double-stranded hybrids with complementary RNA in which, contrary to the usual beta-units, the strands run parallel to each other (Gautier et al. (1987) Nucl. Acids Res. 15:6625–6641). Such oligonucleotide can be a 2'-O-methylribonucleotide (Inoue et al. (1987) Nucl. Acids Res. 15:6131–6148), or a chimeric RNA-DNA analogue (Inoue et al. (1987) FEBS Lett. 215:327–330).

Oligonucleotides of the invention may be synthesized by standard methods known in the art, e.g., by use of an automated DNA synthesizer (such as are commercially available from Biosearch, Applied Biosystems, etc.). As examples, phosphorothioate oligonucleotides may be synthesized by the method of Stein et al. ((1988) Nucl. Acids Res. 16:3209), and methylphosphonate oligonucleotides can be prepared by use of controlled pore glass polymer supports (Sarin et al. (1988) Proc. Natl. Acad. Sci. U.S.A. 85:7448–7451).

To exert their effect, the antisense molecules are delivered into cells that express an ACDK protein in vivo. A number of methods have been developed for delivering antisense DNA or RNA into cells. For instance, antisense molecules can be introduced directly into the tissue site by such standard techniques as electroporation, liposome-mediated transfection, CaCl-mediated transfection, or the use of a gene gun. Alternatively, modified antisense molecules, designed to target the desired cells (e.g., antisense linked to peptides or antibodies that specifically bind receptors or antigens expressed on the target cell surface) can be used.

Because it is often difficult to achieve intracellular concentrations of the antisense sufficient to suppress translation on endogenous mRNAs, a preferred approach utilizes a recombinant DNA construct in which the antisense oligonucleotide is placed under the control of a strong promoter (e.g., the CMV promoter). The use of such a construct to transform cells will result in the transcription of sufficient amounts of single stranded RNAs that will form complementary base pairs with the endogenous ACDK transcripts and thereby prevent translation of ACDK mRNA.

Other types of promoters can also be used to express the antisense oligonucleotide (and other oligonucleotides) of the invention. For example, where it is desired to control expression of the antisense sequence, the antisense oligonucleotide is placed under the control of an inducible (regulatable) promoter, e.g., a tetracycline inducible promoter. As another example, where tissue-selective expression is desired, the antisense oligonucleotide is placed under the control of a tissue-specific or tissue-selective promoter.

Ribozyme molecules designed to catalytically cleave ACDK mRNA transcripts can also be used to prevent translation of ACDK mRNA and expression of ACDK protein (See, e.g., PCT Publication No. WO 90/11364, published Oct. 4, 1990; Sarver et al. (1990) Science 247: 1222–1225 and U.S. Pat. No. 5,093,246). While ribozymes that cleave mRNA at site specific recognition sequences can be used to destroy ACDK mRNAs, the use of hammerhead ribozymes is preferred. Hammerhead ribozymes cleave mRNAs at locations dictated by flanking regions that form complementary base pairs with the target mRNA. The sole requirement is that the target mRNA have the following sequence of two bases: 5'-UG-3'. The construction and production of hammerhead ribozymes is well known in the art and is described more fully in Haseloff and Gerlach (1988) Nature 334:585–591. There are several potential hammerhead ribozyme cleavage sites within the nucleotide sequence of a native ACDK gene. Preferably the ribozyme is engineered so that the cleavage recognition site is located near the 5' end of ACDK mRNA; i.e., to increase efficiency and minimize the intracellular accumulation of non-functional mRNA transcripts. Ribozymes within the invention can be delivered to a cell using a vector as described below.

Endogenous ACDK gene expression can also be reduced by inactivating or "knocking out" the ACDK gene or its promoter using targeted homologous recombination. See, e.g, Kempin et al., Nature 389: 802 (1997); Smithies et al. (1985) Nature 317:230–234; Thomas and Capecchi (1987) Cell 51:503–512; and Thompson et al. (1989) Cell 5:313–321. For example, a mutant, non-functional ACDK gene variant (or a completely unrelated DNA sequence) flanked by DNA homologous to an endogenous ACDK gene (either the coding regions or regulatory regions of an ACDK gene) can be used, with or without a selectable marker and/or a negative selectable marker, to transfect cells that express an ACDK protein in vivo.

Alternatively, endogenous ACDK gene expression might be reduced by targeting deoxyribonucleotide sequences complementary to the regulatory region of an ACDK gene (i.e., the ACDK promoter and/or enhancers) to form triple helical structures that prevent transcription of the ACDK gene in target cells. (See generally, Helene, C. (1991) Anticancer Drug Des. 6(6):569–84; Helene, C., et al. (1992) Ann. N.Y. Acad. Sci. 660:27–36; and Maher, L. J. (1992) Bioassays 14(12):807–15.

Nucleic acid molecules to be used in triple helix formation for the inhibition of transcription are preferably single stranded and composed of deoxyribonucleotides. The base composition of these oligonucleotides should promote triple helix formation via Hoogsteen base pairing rules, which generally require sizable stretches of either purines or pyrimidines to be present on one strand of a duplex. Nucleotide sequences may be pyrimidine-based, which will result in TAT and CGC triplets across the three associated strands of the resulting triple helix. The pyrimidine-rich molecules provide base complementarity to a purine-rich region of a single strand of the duplex in a parallel orientation to that strand. In addition, nucleic acid molecules may be chosen that are purine-rich, for example, containing a stretch of G residues. These molecules will form a triple helix with a DNA duplex that is rich in GC pairs, in which the majority of the purine residues are located on a single strand of the targeted duplex, resulting in CGC triplets across the three strands in the triplex.

Alternatively, the potential sequences that can be targeted for triple helix formation may be increased by creating a so called "switchback" nucleic acid molecule. Switchback molecules are synthesized in an alternating 5'-3', 3'-5' manner, such that they base pair with first one strand of a duplex and then the other, eliminating the necessity for a sizable stretch of either purines or pyrimidines to be present on one strand of a duplex.

Anti sense RNA and DNA, ribozyme, and triple helix molecules of the invention may be prepared by any method known in the art for the synthesis of DNA and RNA molecules. These include techniques for chemically synthesizing oligodeoxyribonucleotides and oligoribonucleotides well known in the art such as for example solid phase phosphoramide chemical synthesis. Alternatively, RNA molecules may be generated by in vitro and in vivo transcription of DNA sequences encoding the antisense RNA molecule. Such DNA sequences may be incorporated into a wide variety of vectors which incorporate suitable RNA polymerase promoters. Alternatively, antisense cDNA constructs that synthesize antisense RNA constitutively or inducibly, depending on the promoter used, can be introduced stably into cell lines.

Moreover, various well-known modifications to nucleic acid molecules may be introduced as a means of increasing intracellular stability and half-life. Possible modifications include but are not limited to the addition of flanking sequences of ribonucleotides or deoxyribonucleotides to the 5' and/or 3' ends of the molecule or the use of phosphorothioate or 2' O-methyl rather than phosphodiesterase linkages within the oligodeoxyribonucleotide backbone.

Probes and Primers

The invention also includes oligonucleotide probes (i.e., isolated nucleic acid molecules conjugated with a detectable label or reporter molecule, e.g., a radioactive isotope, ligand, chemiluminescent agent, or enzyme); and oligonucleotide primers (i.e., isolated nucleic acid molecules that can be annealed to a complementary target DNA strand by nucleic acid hybridization to form a hybrid between the primer and the target DNA strand, then extended along the target DNA strand by a polymerase, e.g., a DNA polymerase). Primer pairs can be used for amplification of a nucleic acid sequence, e.g., by the polymerase chain reaction (PCR) or other conventional nucleic-acid amplification methods. Probes and primers within the invention are generally 15 nucleotides or more in length, preferably 20 nucleotides or more, more preferably 25 nucleotides, and most preferably 30 nucleotides or more. Preferred probes and primers are those that hybridize to a native ACDK gene sequence under high stringency conditions, and those that hybridize ACDK gene homologs under at least moderate stringency conditions. Preferably, probes and primers according to the present invention have complete sequence identity with a native ACDK gene sequence, although probes differing from a native ACDK gene sequence and that retain the ability to hybridize to native ACDK gene sequences under stringent conditions may be designed by conventional methods. Primers and probes based on native ACDK gene sequences disclosed herein can be used to confirm (and, if necessary, to correct) the disclosed native ACDK gene sequences by conventional methods, e.g., by re-cloning and sequencing a native ACDK cDNA.

ACDK Proteins

In other aspects, the present invention utilizes a purified ACDK protein encoded by a nucleic acid of the invention. Preferred forms of ACDK protein include a purified native ACDK protein that has the deduced amino acid sequence of one of SEQ ID NOs:1–8. Variants of native ACDK proteins such as fragments, analogs and derivatives of a native ACDK are also within the invention. Such variants include, e.g., a polypeptide encoded by a naturally occurring allelic variant of a native ACDK gene, a polypeptide encoded by a homolog of a native ACDK gene, and a polypeptide encoded by a non-naturally occurring variant of native ACDK gene.

ACDK protein variants have a peptide sequence that differs from a native ACDK protein in one or more amino acids. The peptide sequence of such variants can feature a deletion, addition, or substitution of one or more amino acids of a native ACDK polypeptide. Amino acid insertions are preferably of about 1 to 4 contiguous amino acids, and deletions are preferably of about 1 to 10 contiguous amino acids. In some applications, variant ACDK proteins substantially maintain a native ACDK protein functional activity. For other applications, variant ACDK proteins lack or feature a significant reduction in an ACDK protein functional activity. Where it is desired to retain a functional activity of a native ACDK protein, preferred ACDK protein variants can be made by expressing nucleic acid molecules within the invention that feature silent or conservative changes. Variant ACDK proteins with substantial changes in functional activity can be made by expressing nucleic acid molecules within the invention that feature less than conservative changes.

ACDK protein fragments corresponding to one or more particular motifs and/or domains or to arbitrary sizes, for example, at least 5, 10, 25, 30, 40, 50, 50, 70, 75, 80, 90, and 100 amino acids in length are within the scope of the present invention. Isolated peptidyl portions of ACDK proteins can be obtained by screening peptides recombinantly produced from the corresponding fragment of the nucleic acid encoding such peptides. In addition, fragments can be chemically synthesized using techniques known in the art such as conventional Merrifield solid phase f-Moc or t-Boc chemistry. For example, an ACDK protein of the present invention may be arbitrarily divided into fragments of desired length with no overlap of the fragments, or preferably divided into overlapping fragments of a desired length. The fragments can be produced (recombinantly or by chemical synthesis) and tested to identify those peptidyl fragments which can function as either agonists or antagonists of a native ACDK protein.

Another aspect of the present invention concerns recombinant forms of the ACDK proteins. Recombinant polypeptides preferred by the present invention are encoded by a nucleic acid that has at least 85% sequence identity (e.g., 85, 86, 87, 88, 89, 90, 91, 92, 93, 94, 95, 96, 97, 98, 99, 100%) with the nucleic acid sequence of one of SEQ ID NOs:1–8. In a preferred embodiment, variant ACDK proteins have one or more functional activities of a native ACDK protein.

ACDK protein variants can be generated through various techniques known in the art. For example, ACDK protein variants can be made by mutagenesis, such as by introducing discrete point mutation(s), or by truncation. Mutation can give rise to an ACDK protein variant having substantially the same, or merely a subset of the functional activity of a native ACDK protein. Alternatively, antagonistic forms of the protein can be generated which are able to inhibit the function of the naturally occurring form of the protein, such as by competitively binding to another molecule that interacts with an ACDK protein. In addition, agonistic forms of the protein may be generated that constitutively express one or more ACDK functional activities. Other variants of ACDK proteins that can be generated include those that are resistant to proteolytic cleavage, as for example, due to mutations which alter protease target sequences. Whether a change in the amino acid sequence of a peptide results in an ACDK protein variant having one or more functional activities of native ACDK protein can be readily determined by testing the variant for a native ACDK protein functional activity.

As another example, ACDK protein variants can be generated from a degenerate oligonucleotide sequence. Chemical synthesis of a degenerate gene sequence can be carried out in an automatic DNA synthesizer, and the synthetic genes then ligated into an appropriate expression vector. The purpose of a degenerate set of genes is to provide, in one mixture, all of the sequences encoding the desired set of potential ACDK protein sequences. The synthesis of degenerate oligonucleotides is well known in the art (see for example, Narang, SA (1983) Tetrahedron 39:3; Itakura et al. (1981) Recombinant DNA, Proc 3rd Cleveland Sympos. Macromolecules, ed. A G Walton, Amsterdam: Elsevier pp 273–289; Itakura et al. (1984) Annu. Rev. Biochem. 53:323; Itakura et al. (1984) Science 198:1056; Ike et al. (1983) Nucleic Acid Res. 11:477. Such techniques have been employed in the directed evolution of other proteins (see, for example, Scott et al. (1990) Science 249:386–390; Roberts et al. (1992) Proc. Natl. Acad. Sci. USA 89:2429–2433; Devlin et al. (1990) Science 249: 404–406; Cwirla et al. (1990) Proc. Natl. Acad. Sci. USA 87: 6378–6382; as well as U.S. Pat. Nos. 5,223,409; 5,198,346; and 5,096,815).

Similarly, a library of coding sequence fragments can be provided for an ACDK gene clone in order to generate a variegated population of ACDK protein fragments for screening and subsequent selection of fragments having one or more native ACDK functional activities. A variety of techniques are known in the art for generating such libraries, including chemical synthesis. In one embodiment, a library of coding sequence fragments can be generated by (i) treating a double-stranded PCR fragment of an ACDK gene coding sequence with a nuclease under conditions wherein nicking occurs only about once per molecule; (ii) denaturing the double-stranded DNA; (iii) renaturing the DNA to form double-stranded DNA which can include sense/antisense pairs from different nicked products; (iv) removing single-stranded portions from reformed duplexes by treatment with S1 nuclease; and (v) ligating the resulting fragment library into an expression vector. By this exemplary method, an expression library can be derived which codes for N-terminal, C-terminal and internal fragments of various sizes.

A wide range of techniques are known in the art for screening gene products of combinatorial libraries made by point mutations or truncation, and for screening cDNA libraries for gene products having a certain property. Such techniques will be generally adaptable for rapid screening of the gene libraries generated by the combinatorial mutagenesis of ACDK gene variants. The most widely used techniques for screening large gene libraries typically comprise cloning the gene library into replicable expression vectors, transforming appropriate cells with the resulting library of vectors, and expressing the combinatorial genes under conditions in which detection of a desired activity facilitates relatively easy isolation of the vector encoding the gene whose product was detected.

Combinatorial mutagenesis has a potential to generate very large libraries of mutant proteins, e.g., in the order of $10^{26}$ molecules. Combinatorial libraries of this size may be technically challenging to screen even with high throughput screening assays. To overcome this problem, techniques such as recursive ensemble mutagenesis (REM) that allow one to avoid the very high proportion of non-functional proteins in a random library and simply enhance the frequency of functional proteins (thus decreasing the complexity required to achieve a useful sampling of sequence space) can be used. REM is an algorithm which enhances the frequency of functional mutants in a library when an appropriate selection or screening method is employed (Arkin and Yourvan (1992) Proc. Natl. Acad. Sci. USA 89:7811–7815;

Yourvan et al. (1992) Parallel Problem Solving from Nature, 2., In Maenner and Manderick, eds., Elsevier Publishing Co., Amsterdam, pp. 401–410; Delgrave et al. (1993) Protein Engineering 6(3):327–331).

The invention also provides for reduction of ACDK proteins to generate mimetics, e.g. peptide or non-peptide agents, that are able to disrupt binding of an ACDK protein to other proteins or molecules with which a native ACDK protein interacts. Thus, the mutagenic techniques described can also be used to map which determinants of an ACDK protein participate in protein—protein interactions involved in, for example, binding of an ACDK protein to other proteins which may function upstream (including both activators and repressors of its activity) of the ACDK protein or to proteins or nucleic acids which may function downstream of the ACDK protein, and whether such molecules are positively or negatively regulated by the ACDK protein. To illustrate, the critical residues of an ACDK protein which are involved in molecular recognition of, for example, a molecule having a moiety that binds the ACDK protein can be determined and used to generate ACDK protein-derived peptidomimetics which competitively inhibit binding of ACDK protein with that moiety. By employing, for example, scanning mutagenesis to map the amino acid residues of an ACDK protein that are involved in binding other proteins, peptidomimetic compounds can be generated which mimic those residues of native ACDK protein. Such mimetics may then be used to interfere with the normal function of an ACDK protein. For instance, non-hydrolyzable peptide analogs of such residues can be generated using benzodiazepine (e.g., see Freidinger et al. in Peptides: Chemistry and Biology, G. R. Marshall ed., ESCOM Publisher: Leiden, Netherlands, 1988), azepine (e.g., see Huffman et al. in Peptides: Chemistry and Biology, G. R. Marshall ed., ESCOM Publisher: Leiden, Netherlands, 1988), substituted gamma lactam rings (Garvey et al. in Peptides: Chemistry and Biology, G. R. Marshall ed., ESCOM Publisher: Leiden, Netherlands, 1988), keto-methylene pseudopeptides (Ewenson et al. (1986) J. Med. Chem. 29:295; and Ewenson et al. in Peptides: Structure and Function (Proceedings of the 9th American Peptide Symposium) Pierce Chemical Co. Rockland, Ill. 1985), beta-turn dipeptide cores (Nagai et al. (1985) Tetrahedron Lett 26:647; and Sato et al. (1986) J. Chem. Soc. Perkin. Trans. 1:1231), and b-aminoalcohols (Gordon et al. (1985) Biochem. Biophys. Res. Commun. 126:419; and Dann et al. (1986) Biochem. Biophys. Res. Commun. 134:71). ACDK proteins may also be chemically modified to create ACDK derivatives by forming covalent or aggregate conjugates with other chemical moieties, such as glycosyl groups, lipids, phosphate, acetyl groups and the like. Covalent derivatives of an ACDK protein can be prepared by linking the chemical moieties to functional groups on amino acid side chains of the protein or at the N-terminus or at the C-terminus of the polypeptide.

The present invention further pertains to methods of producing the subject ACDK proteins. For example, a host cell transfected with a nucleic acid vector directing expression of a nucleotide sequence encoding the subject polypeptides can be cultured under appropriate conditions to allow expression of the peptide to occur. The cells may be harvested, lysed, and the protein isolated. A recombinant ACDK protein can be isolated from host cells using techniques known in the art for purifying proteins including ion-exchange chromatography, gel filtration chromatography, ultrafiltration, electrophoresis, and immunoaffinity purification with antibodies specific for such protein.

For example, after an ACDK protein has been expressed in a cell, it can be isolated using any immuno-affinity chromatography. For instance, an ACDK-specific antibody (e.g., produced as described below) can be immobilized on a column chromatography matrix, and the matrix can be used for immuno-affinity chromatography to purify ACDK protein from cell lysates by standard methods (see, e.g., Ausubel et al., supra). After immuno-affinity chromatography, ACDK protein can be further purified by other standard techniques, e.g., high performance liquid chromatography (see, e.g., Fisher, Laboratory Techniques In Biochemistry And Molecular Biology, Work and Burdon, eds., Elsevier, 1980). In another embodiment, ACDK protein is expressed as a fusion protein containing an affinity tag (e.g., GST) that facilitates its purification.

ACDK-Specific Antibodies

ACDK proteins (or immunogenic fragments or analogs thereof) can be used to raise antibodies useful in the invention. Such proteins can be produced by recombinant techniques or synthesized as described above. In general, ACDK proteins can be coupled to a carrier protein, such as KLH, as described in Ausubel et al., supra, mixed with an adjuvant, and injected into a host animal. Antibodies produced in that animal can then be purified by peptide antigen affinity chromatography. In particular, various host animals can be immunized by injection with an ACDK protein or an antigenic fragment thereof. Commonly employed host animals include rabbits, mice, guinea pigs, and rats. Various adjuvants that can be used to increase the immunological response depend on the host species and include Freund's adjuvant (complete and incomplete), mineral gels such as aluminum hydroxide, surface active substances such as lysolecithin, pluronic polyols, polyanions, peptides, oil emulsions, keyhole limpet hemocyanin, and dinitrophenol. Other potentially useful adjuvants include BCG (bacille Calmette-Guerin) and *Corynebacterium parvum*.

Polyclonal antibodies are heterogeneous populations of antibody molecules that are contained in the sera of the immunized animals. Antibodies within the invention therefore include polyclonal antibodies and, in addition, monoclonal antibodies, single chain antibodies, Fab fragments, $F(ab')_2$ fragments, and molecules produced using a Fab expression library. Monoclonal antibodies, which are homogeneous populations of antibodies to a particular antigen, can be prepared using the ACDK proteins described above and standard hybridoma technology (see, for example, Kohler et al., Nature 256:495, 1975; Kohler et al., Eur. J. Immunol. 6:511, 1976; Kohler et al., Eur. J. Immunol. 6:292, 1976; Hammerling et al., "Monoclonal Antibodies and T Cell Hybridomas," Elsevier, N.Y., 1981; Ausubel et al., supra). In particular, monoclonal antibodies can be obtained by any technique that provides for the production of antibody molecules by continuous cell lines in culture such as described in Kohler et al., Nature 256:495, 1975, and U.S. Pat. No. 4,376,110; the human B-cell hybridoma technique (Kosbor et al., Immunology Today 4:72, 1983; Cole et al., Proc. Natl. Acad. Sci. USA 80:2026, 1983), and the EBV-hybridoma technique (Cole et al., "Monoclonal Antibodies and Cancer Therapy," Alan R. Liss, Inc., pp. 77–96, 1983). Such antibodies can be of any immunoglobulin class including IgG, IgM, IgE, IgA, IgD and any subclass thereof. A hybridoma producing a mAb of the invention may be cultivated in vitro or in vivo. The ability to produce high titers of mAbs in vivo makes this a particularly useful method of production.

Human or humanoid antibodies that specifically bind an ACDK protein can also be produced using known methods. For example, human antibodies against ACDK proteins can be made by adapting known techniques for producing human antibodies in animals such as mice. See, e.g., Fishwild, D. M. et al., Nature Biotechnology 14 (1996): 845–851; Heijnen, I. et al., Journal of Clinical Investigation 97 (1996): 331–338; Lonberg, N. et al., Nature 368 (1994): 856–859; Morrison, S. L., Nature 368 (1994): 812–813; Neuberger, M., Nature Biotechnology 14 (1996): 826; and U.S. Pat. Nos. 5,545,806; 5,569,825; 5,877,397; 5,939,598; 6,075,181; 6,091,001; 6,114,598; and 6,130,314. Humanoid antibodies against ACDK proteins can be made from non-human antibodies by adapting known methods such as those described in U.S. Pat. Nos. 5,530,101; 5,585,089; 5,693,761; and 5,693,762.

Once produced, polyclonal or monoclonal antibodies can be tested for specific ACDK recognition by Western blot or immunoprecipitation analysis by standard methods, for example, as described in Ausubel et al., supra. Antibodies that specifically recognize and bind to ACDK are useful in the invention. For example, such antibodies can be used in an immunoassay to monitor the level of ACDK produced by a mammal (e.g., to determine the amount or subcellular location of ACDK).

Preferably, the ACDK-specific antibodies of the invention are produced using fragments of the ACDK protein that lie outside highly conserved regions and appear likely to be antigenic, by criteria such as high frequency of charged residues. Cross-reactive anti-ACDK protein antibodies are produced using a fragment of an ACDK protein that is conserved among members of this family of proteins. In one specific example, such fragments are generated by standard techniques of PCR, and are then cloned into the pGEX expression vector (Ausubel et al., supra). Fusion proteins are expressed in E. coli and purified using a glutathione agarose affinity matrix as described in Ausubel, et al., supra.

In some cases it may be desirable to minimize the potential problems of low affinity or specificity of antisera. In such circumstances, two or three fusions can be generated for each protein, and each fusion can be injected into at least two rabbits. Antisera can be raised by injections in a series, preferably including at least three booster injections. Antiserum is also checked for its ability to immunoprecipitate recombinant ACDK proteins or control proteins, such as glucocorticoid receptor, CAT, or luciferase.

The antibodies of the invention can be used, for example, in the detection of ACDK protein in a biological sample. Antibodies also can be used in a screening assay to measure the effect of a candidate compound on expression or localization of an ACDK protein. Additionally, such antibodies can be used to interfere with the interaction of an ACDK protein and other molecules that bind an ACDK protein.

Techniques described for the production of single chain antibodies (e.g., U.S. Pat. Nos. 4,946,778, 4,946,778, and 4,704,692) can be adapted to produce single chain antibodies against an ACDK protein, or a fragment thereof. Single chain antibodies are formed by linking the heavy and light chain fragments of the Fv region via an amino acid bridge, resulting in a single chain polypeptide.

Antibody fragments that recognize and bind to specific epitopes can be generated by known techniques. For example, such fragments include but are not limited to $F(ab')_2$ fragments that can be produced by pepsin digestion of the antibody molecule, and Fab fragments that can be generated by reducing the disulfide bridges of $F(ab')_2$ fragments. Alternatively, Fab expression libraries can be constructed (Huse et al., Science 246:1275, 1989) to allow rapid and easy identification of monoclonal Fab fragments with the desired specificity.

Proteins that Associate with ACDK

The invention also features methods for identifying polypeptides that can associate with an ACDK protein. Any method that is suitable for detecting protein—protein interactions can be employed to detect polypeptides that associate with an ACDK protein. Among the traditional methods that can be employed are co-immunoprecipitation, crosslinking, and co-purification through gradients or chromatographic columns of cell lysates or proteins obtained from cell lysates and the use of an ACDK protein to identify proteins in the lysate that interact with it. For these assays, the ACDK protein can be a full-length ACDK protein, a particular domain of an ACDK protein, or some other suitable ACDK protein. Once isolated, such an interacting protein can be identified and cloned and then used, in conjunction with standard techniques, to alter the activity of the ACDK protein with which it interacts. For example, at least a portion of the amino acid sequence of a protein that interacts with ACDK protein can be ascertained using techniques well known to those of skill in the art, such as via the Edman degradation technique. The amino acid sequence obtained can be used as a guide for the generation of oligonucleotide mixtures that can be used to screen for gene sequences encoding the interacting protein. Screening can be accomplished, for example, by standard hybridization or PCR techniques. Techniques for the generation of oligonucleotide mixtures and the screening are well-known (Ausubel et al., supra; and Innis et al., supra).

Additionally, methods can be employed that result directly in the identification of genes that encode proteins that interact with an ACDK protein. These methods include, for example, screening expression libraries, in a manner similar to the well known technique of antibody probing of 1gt11 libraries, using a labeled ACDK protein or an ACDK fusion protein, for example, an ACDK protein or domain fused to a marker such as an enzyme, fluorescent dye, a luminescent protein, or to an IgFc domain.

There are also methods available that can detect protein—protein interaction in vivo. For example, as described herein the two-hybrid system can be used to detect such interactions in vivo. See, e.g., Chien et al., Proc. Natl. Acad. Sci. USA 88:9578, 1991. Briefly, as one example of utilizing such a system, plasmids are constructed that encode two hybrid proteins: one plasmid includes a nucleotide sequence encoding the DNA-binding domain of a transcription activator protein fused to a nucleotide sequence encoding a native ACDK protein, an ACDK protein variant, or an ACDK fusion protein, and the other plasmid includes a nucleotide sequence encoding the transcription activator protein's activation domain fused to a cDNA encoding an unknown protein which has been recombined into this plasmid as part of a cDNA library. The DNA-binding domain fusion plasmid and the cDNA library are transformed into a strain of the yeast Saccharomyces cerevisiae that contains a reporter gene (e.g., HBS or lacZ) whose regulatory region contains the transcription activator's binding site. Either hybrid protein alone cannot activate transcription of the reporter gene: the DNA-binding domain hybrid cannot because it does not provide activation function, and the activation domain hybrid cannot because it cannot localize to the activator's binding sites. Interaction of the two hybrid proteins reconstitutes the functional activator protein and results in expression of the reporter gene, which is detected by an assay for the reporter gene product.

The two-hybrid system or related methodology can be used to screen activation domain libraries for proteins that interact with the "bait" gene product. By way of example, and not by way of limitation, an ACDK protein may be used as the bait. Total genomic or cDNA sequences are fused to the DNA encoding an activation domain. This library and a plasmid encoding a hybrid of a bait ACDK protein fused to the DNA-binding domain are co-transformed into a yeast reporter strain, and the resulting transformants are screened for those that express the reporter gene. For example, a bait ACDK gene sequence, such as that encoding an ACDK protein or a domain of an ACDK protein can be cloned into a vector such that it is translationally fused to the DNA encoding the DNA-binding domain of the GAL4 protein. These colonies are purified and the library plasmids responsible for reporter gene expression are isolated. DNA sequencing is then used to identify the proteins encoded by the library plasmids.

A cDNA library of the cell line from which proteins that interact with a bait ACDK protein are to be detected can be made using methods routinely practiced in the art. For example, the cDNA fragments can be inserted into a vector such that they are translationally fused to the transcriptional activation domain of GAL4. This library can be co-transformed along with the ACDK-GAL4 encoding fusion plasmid into a yeast strain which contains a lacZ gene driven by a promoter which contains GAL4 activation sequence. A cDNA encoded protein, fused to GAL4 transcriptional activation domain, that interacts with bait ACDK protein will reconstitute an active GAL4 protein and thereby drive expression of the HIS3 gene. Colonies that express HIS3 can then be purified from these strains and used to produce and isolate bait ACDK protein-interacting proteins using techniques routinely practiced in the art.

Detection of ACDK Polynucleotides and Proteins

The invention encompasses methods for detecting the presence of an ACDK protein or an ACDK nucleic acid in a biological sample as well as methods for measuring the level of an ACDK protein or an ACDK nucleic acid in a biological sample.

An exemplary method for detecting the presence or absence of ACDK in a biological sample involves obtaining a biological sample from a test subject (e.g., a human patient), contacting the biological sample with a compound or an agent capable of detecting an ACDK protein or a nucleic acid encoding an ACDK protein (e.g., mRNA or genomic DNA), and analyzing binding of the compound or agent to the sample after washing. Those samples having specifically bound compound or agent are those that express an ACDK protein or a nucleic acid encoding an ACDK protein.

A preferred agent for detecting a nucleic acid encoding an ACDK protein is a labeled nucleic acid probe capable of hybridizing (e.g., under stringent hybridization conditions) to the nucleic acid encoding an ACDK protein. The nucleic acid probe can be, for example, all or a portion of a native ACDK gene itself or all or a portion of a complement of a native ACDK gene. Similarly, the probe can also be all or a portion of an ACDK gene variant, or all or a portion of a complement of an ACDK gene variant. For instance, oligonucleotides at least 15, 30, 50, 75, 100, 125, 150, 175, 200, 225, or 250 nucleotides in length that specifically hybridize under stringent conditions to a native ACDK gene or a complement of a native ACDK gene can be used as probes within the invention. A preferred agent for detecting an ACDK protein is an antibody capable of binding to an ACDK protein, preferably an antibody with a detectable label. Such antibodies can be polyclonal, or more preferably, monoclonal. An intact antibody, or a fragment thereof (e.g., Fab or F(ab')$_2$) can be used.

Detection methods of the invention can be used to detect an mRNA encoding an ACDK protein, a genomic DNA encoding an ACDK protein, or an ACDK protein in a biological sample in vitro as well as in vivo. For example, in vitro techniques for detection of mRNAs encoding an ACDK protein include Northern hybridizations and in situ hybridizations. In vitro techniques for detection of an ACDK protein include enzyme linked immunosorbent assays (ELISAs), Western blots, immunoprecipitations and immunofluorescence. In vitro techniques for detection of genomic DNA encoding an ACDK protein include Southern hybridizations. In vivo techniques for detection of an ACDK protein include introducing a labelled anti-ACDK-specific antibody into a biological sample or test subject. For example, the antibody can be labeled with a radioactive marker whose presence and location in a biological sample or test subject can be detected by standard imaging techniques.

Screening for Compounds that Interact with ACDK Protein

The invention also encompasses methods for identifying compounds that specifically bind to an ACDK protein. One such method involves the steps of providing immobilized purified ACDK protein and at least one test compound; contacting the immobilized protein with the test compound; washing away substances not bound to the immobilized protein; and detecting whether or not the test compound is bound to the immobilized protein. Those compounds remaining bound to the immobilized protein are those that specifically interact with the ACDK protein.

Assays for Compounds that Interfere with an ACDK Protein Binding to a CDK Protein The invention can be used to screen candidate substances for the ability to inhibit the interaction of an ACDK protein with a CDK protein. In an exemplary screening method, the two-hybrid expression system is used to screen for substances capable of inhibiting an ACDK-CDK protein interaction in vivo. In this system, a GAL4 binding site, linked to a reporter gene such as lacZ, is contacted in the presence and absence of a candidate substance with a GAL4 binding domain linked to a CDK protein fragment and a GAL4 transactivation domain II linked to an ACDK protein fragment. Expression of the reporter gene is monitored, and a decrease in its expression is an indication that the candidate substance inhibits the interaction of the ACDK protein with the CDK protein. One of ordinary skill in the art will recognize that other screening assays are known and can be used to identify candidate substances that inhibit an ACDK-CDK protein interaction.

For example, in another screening method, one of the protein components of an ACDK protein-CDK protein binding complex, such as an ACDK protein, a CDK protein-binding fragment of an ACDK protein, a CDK protein, or an ACDK protein-binding fragment of a CDK protein is immobilized. Polypeptides can be immobilized using methods known in the art. Such methods include adsorption onto a plastic microliter plate or specific binding of a glutathione-5-transferase (GST)-fusion protein to a polymeric bead containing glutathione. For example, a GST-CDK protein fusion protein can be bound to glutathione-Sepharose beads. The immobilized protein (e.g., GST-CDK protein) is then contacted with the labeled protein to which it binds (an ACDK protein in this example) in the presence and absence of a candidate substance. Unbound protein can be removed by washing. The complex can then be solubilized and analyzed to determine the amount of bound (labeled) protein. A decrease in binding is an indication that the candidate substance inhibits the interaction of the ACDK protein and the CDK protein. A variation of the above-described screening method can be used to screen for other classes of candidate substances, e.g., those that disrupt previously-formed ACDK protein-CDK protein complexes. In this variation, a complex containing an ACDK protein (or a CDK protein-binding ACDK protein fragment) bound to a CDK protein (or an ACDK protein-binding CDK protein fragment) is immobilized and contacted with a candidate compound. Detection of disruption of the ACDK protein-ACDK protein complex by the candidate substance identifies the candidate substance as a potential modulator of ACDK protein-mediated cellular events.

EXAMPLES

The present invention is further illustrated by the following specific examples. The examples are provided for illustration only and are not to be construed as limiting the scope or content of the invention in any way.

Example 1

Cloning and Characterization of Human ACDK1

RNA, cDNA clones, cDNA library and DNA samples. Human total fetal brain RNA was purchased from Clontech (64019-1). The IMAGE cDNA clone (R60797) for WI21848 was purchased from Genome System Co. A human fetal brain cDNA library was purchased from Origene. Screening of this library was conducted using PCR amplification according to the manufacturer's instruction.

5', and 3'RACE. 5' and 3' RACE were conducted using the SMART RACE kit purchased from Clontech (K1811-1) according to the manufacturer's instruction with some modifications. Fetal brain total RNA was used for reverse transcription. For 5' RACE, the first-strand cDNA synthesis was primed using a gene specific primer and a SMART oligo was also present in the reaction. After reverse transcription reached the end of the mRNA template, several dC residues were added to the end of the cDNA. The SMART oligo primer, which contains 3-dG at its 3' end, anneals to the tail of the newly synthesized cDNA and then serves as template for further extension of the cDNA by RT. For amplification of 5' end sequence, an internal gene-specific reverse primer and a UP primer, which is complimentary to SMART oligo was used to perform PCR using the RT products as templates. To increase the specificity and product yield of 5' RACE, nested PCR was then performed using another internal gene-specific primer and the NUP primer (internal primer of UP). For 3' RACE, the first-strand cDNA was synthesized using a modified oligo-dT with an UP primer tail. The UP primer and a gene specific forward primer were used for first round PCR. Nested PCR was performed using NUP and an internal gene-specific forward primer. PCR reactions were carried out in a final volume of 35 µl. After the RT reaction, the samples were denatured at 94° C. for 1 min. Amplifications were carried out with 2 cycles of 5-sec denaturing at 94° C. and 4-min extension at 72° C., then 2 cycles of 5-sec denaturing at 94° C. and 4-min extension at 70° C., and then an additional 25 cycles of 5-sec at 94° C. and 4-min at 68° C. PCR products obtained from nested PCR were loaded on to a 2.5% agarose gel and individual bands were excised from the gel for direct sequencing.

Northern blot analysis. Northern blot was carried out with two commercial mRNA filters, the Origene filter containing 2 µg polyA RNA from 6 adult tissues (lung, small intestine, skeletal muscle, stomach, testis and placenta) and the Clontech filter containing 2 µg polyA RNA from 4 fetal tissues (kidney, liver, lung and brain). The filters were probed with a 500-bp cDNA fragment labeled with $\alpha$-$^{32}$P dCTP using the random primer extension system (Life Technology). Hybridization was carried out overnight and the filters were then washed in a washing buffer (2×SSC, 0.1% SDS) at 50° C. for 20-min, then again for 10-min. Washed filters were exposed to X-ray films overnight or longer.

Real time PCR. A human fetal multiple tissue cDNA panel containing brain, heart, kidney, liver, skeleton muscle, spleen and thymus was purchased from Clontech (K1425-1). Real time PCR amplification was carried out using an iCycler iQ™ Real Time PCR Detection System (Bio-Rad, 170-8740). PCR was performed in triplicate for each tissue tested. PCR reactions were carried out in a final volume of 25 µl containing 0.25 µl of regular 10×PCR buffer, 0.25 µl of 10× dNTPs, 8 pMol of each primer, 0.75 U of regular Taq enzyme, and 0.5 µl of 10× CYBR Green dye (Molecular Probes, S-7567). The samples were denatured at 95° C. for 3-min. Amplifications were carried out with 40 cycles of 30-sec denaturing at 95° C. and 30-sec annealing at 58° C. and 30-sec extension at 72° C. After each cycle of amplification, the CYBR Green dye binds to the PCR products, which allows the CCD detector within the iCycler immediate feedback on reaction success, reports data on the PCR in progress in Real Time. The relative expression level is determined by comparing the mean value of minimum PCR cycle numbers (threshold) that the fluorescence dye bound with PCR products can be detected by the CCD detector.

DNA Sequencing. BAC DNA was purified using the Qiagen Plasmid Mini Kit (Qiagen 12125) according to the manufacturer's instructions. Each sequencing reaction (20 µl) contained 2–3 µg BAC DNA, 2 µl of BigDye reaction mix (Perkin Elmer), 1 µl of primer (3.2 pmol) and 3 µl of 5× sequencing buffer (400 mM Tris-HCl, 10 mM MgCl$_2$, pH 9.0). After 25 cycles of 96° C. for 10 seconds, 50° C. for 5 seconds and 60° C. for 4 minutes, 1/10 volume (2 µl) of 3 M NaOAC (pH 5.2) and 3 volumes (60 µl) of 95% EtOH were added to each sequencing reaction. After 10 minutes at room temperature, the samples were centrifuged for 20 minutes at room temperature. The pellet was washed once with 250 µl of 70% EtOH and dried in a vacuum drier, then dissolved in 20 µl of template suppression reagent (Perkin Elmer). The sequences were then read with an ABI 310 automated DNA sequencer.

For direct sequencing of PCR products, amplifications were carried out in a final volume of 22 µl consisting of 40 ng genomic DNA with 4 duplicate reactions for each sample. All PCR products from each sample were electrophoresed on a 2.5% agarose gel and the expected bands were excised from the gel and transferred into 1.5-ml Eppendorf tubes. The tubes were frozen at −20° C. for 5–10 min, and the gel was then smashed while frozen. PCR products were eluted out of the gels by brief centrifugation. The supernatant was directly used for sequencing with an ABI 310 automated DNA sequencer.

Protein and DNA homology searches were conducted using tblastn, tblastx and blastn programs (http://www.ncbi.nlm.nih.gov/BLAST/blast_program.html). Multiple sequence alignment was performed using the GeneDoc program.

Two EST markers (WI21848 and EST30005) within the BAC clone 36918 in the UFS critical region were used to clone ACDK1. PCR amplifications by two primers specific for EST30005 produced a predicted fragment from fetal brain cDNA and no product from BAC DNA and genomic DNA, confirming that EST30005 was indeed derived from coding sequences. These two primers were then used to directly sequence the BAC clone 36918, which contains the EST. An intron was discovered by sequence comparison between BAC sequence and EST30005.

The full-length human ACDK1 cDNA was cloned by SMART RACE techniques. 3' RACE using the primers NUP and EXON4F produced a 3817 bp band. At the same time, the entire 1.4 kb insert of an I.M.A.G.E. cDNA clone for WI21848 was sequenced. No open reading frame was identified from this sequence. Due to the physical closeness of the EST markers EST30005 and WI21848, their sequences were compared and an overlap was identified. These results suggested that the two ESTs were derived from the same gene. PCR amplification using primers 3UTR1F and 3UTR7R from cDNA and BAC DNA confirmed these results.

To identify additional 5' sequences, 5' RACE was performed with primers NUP and EXON3R. This process yielded a unique fragment of approximately 2000 bp. The fragment was excised from the gel and directly sequenced. Subsequent 5' RACE did not identify additional sequences. The full-length cDNA sequence consists of 5747 bp and encodes a predicted protein of 951 amino acids. The gene contains a large 3' untranslated region. The gene was named ACDK1. The sequence of this gene is indicated herein as SEQ ID NO:1.

Physical mapping and genomic structure of ACDK1. To determine the precise location of the ACDK1 gene, EST markers previously studied and two new ESTs (MEX1 and 3UTR7) were tested against the BAC/PAC contig for the region. MEX1 is derived from sequence in the 5'UTR of ACDK1 and 3UTR7 is from the 3UTR of the gene. EST30005 contains exon 4 and partial sequences of exon 3 and exon 5, while WI21848 is derived from the 3'UTR. The ACDK1 gene was localized to a region defined by the centromeric marker 377H12R and the telomeric marker GOT1. The direction of transcription is from centromeric to telomeric.

In order to determine the genomic structure of the ACDK1 gene, primers in the coding region were used directly to sequence the BAC clone 36918. A total of 11 exons were identified. Exon 1 is the largest exon and contains 844 bp of the coding sequence. While exon 6 is the smallest exon and contains 48 bp of the coding sequence. All introns follow GT/AG rule for exon/intron junctions.

Mutation analysis in Urofacial Syndrome (UFS) patients. As ACDK1 maps to the UFS critical region, a search was performed for mutations in the ACDK1 gene in UFS patients. The mutation analyses was performed in two patients (4-3 and 6-3) from Columbia, two US patients (30-3 and 31-3) and one unaffected carrier (31-2, mother of patient 31-3). The entire coding region, untranslated regions and intron/exon junctions of ACDK1 were amplified from genomic DNA using 18 primer pairs located in the introns. Direct sequencing of PCR products only revealed three silent mutations (1284 G→T in exon 1, 1725 T→C in exon 3 and 2484 C→T in exon 8, the first base of the start codon is position 1) and three polymorphisms in the 3'UTR region (3262 T→A, 3774 T→C and 4137 C→T). None of these mutations appears to be pathogenic as the patients are not homozygous for these polymorphisms.

Example 2

Characterization and Cloning of the ACDK Family

Database searches revealed only limited nucleotide sequence homologies between ACDK1 and other human ESTs. However, searches of the ACDK1 protein sequence by the tblastn program identified amino acid sequence homologies with ESTs from human, mouse and several other species. A total of four clusters of EST markers from human being have been identified. They are Hs.274579 (ACDK1), Hs. 271221, Hs. 175043 and Hs. 44095 respectively.

To clone the ACDK gene family, three EST markers, R56624, AL041195 and EST26555 were selected from the unigene clusters respectively. The ID for these I.M.A.G.E. clones are yg94d11.r1 for R56624, DKFZp434I1016r1 434 for AL041195, and AA323653 for EST26555. The sequence for each clone was from 5' end (r1). While the sequences from 3' end (s1) for these clones were identified from database on web site. For EST R56624, 3' end sequence was downloaded from WashU-Merck Human EST Project web site (http://genome.wustl.edu/est/esthmpg.html) on FTP service of sub-directory for clone yg94d11.s1 (specific sequence for clone r56624 from 3' end). EST AL041195 is a clone from Germany Genome Center. The sequence ID for 3' end is AL041196. The full insert of each clone was amplified using primers from 5' end and 3' end (before poly A region) and was sequenced.

3' RACE for the 3' end sequence was performed using SMART RACE techniques. To expand 5' end sequences, the sequences from those clones were used to search the human EST database again for overlapping sequences. To identify the full-length cDNA sequences, 5' RACE was performed by SMART RACE techniques as described above. The full-length sequence for EST r56624 is 4058 bp (SEQ ID NO: 2), encoding a predicted protein of 875 amino acids (SEQ ID NO: 10), and named as ACDK2. ACDK3 corresponded to EST AL041195, containing 3183 bp of cDNA sequence (SEQ ID NO: 3), encoding a putative protein of 707 amino acids (SEQ ID NO: 11). The full-length sequence identified based on EST26555 was then named as ACDK4. This transcript contains 4765 base-pairs of cDNA sequence (SEQ ID NO: 4) and encodes a protein with 775 amino acids in length (SEQ ID NO: 12).

Sequence analysis of ACDK gene family revealed that this gene family contains a domain (Ancient Conserved Domain, ACD) which is highly conserved in divergent species including *C. elegans, Drosophila melanogaster*, bacteria and yeast which is suggestive of its importance (FIG. 1).

Example 3

Tissue Distribution and Chromosomal Location of the ACDK Genes

Expression analyses of the ACDK gene family were carried out by Northern blotting. Referring to FIG. 2 most members of the ACDK gene family were expressed in all tissues tested except that ACDK1 showed high expression only in the brain and detectable expression in testis. Expression of the ACDK gene family was also analyzed by real-time quantitative RT-PCR. These analyses revealed that: ACDK1 was expressed in kidney, lung, liver and heart (in addition to testis and brain); ACDK2 was highly expressed in brain, kidney, and placenta; ACDK3 was highly expressed in heart and spleen; and ACDK4 was highly expressed in heart, placenta, kidney, lung and testis.

ACDK1 was localized to chromosome 10q23–10q24 by contig mapping. The GeneBridge 4 radiation hybrid panel (RH02.05, Research Genetics) was used to map the chromosome localization for the rest of ACDK members. Primers from 3' untranslated region of each ACDK member were used to amplify 93 radiation hybrid clones of the whole human genome. The data were submitted to the GeneBridge 4.0 mapping server at the Whitehead Institute (http://carbon.wi.mit.edu:8000/cgi-bin/contig/rhmapper.p1) for analysis. ACDK2 was mapped to chromosome 10 between markers D10S 222 and SGC31986. ACDK3 and ACDK4 were mapped to chromosome 2 within one BAC clone between markers CHLC.GATA86A06 and WI-13313.

Example 4

Functional Characterization of ACDK Proteins

ACDK homology modeling: Models for ACDK were generated by subjecting their predicted amino acid sequences to FASTA-CHECK analysis against all the PDB entries available in the SWISS-PROT database. The matrix chosen for this analysis was Smith-Waterman (Blosum50). The search provided two major (1BOB and 1VIN) and several minor templates for homology modeling. The predicted ACDK sequence was threaded into the crystal co-ordinates of the templates using LOOK II (Molecular Applications Group). Ten independent models were built and the averaged model was energy-minimized using DISCOVER module of INSIGHT-II (Molecular Simulations). The fits were checked by WHAT-IF and PROCHECK 2.0. The energy minimized structure of these molecules revealed structural homology to cyclin molecules, but did not show basic amino acid sequence homology. In addition, no classic cyclin box was present within the protein sequences.

Example 5

Expression of Recombinant Protein Containing ACD Domain and Antibody Production

The construct containing the ACD domain of ACDK4 (320 amino acids) was made in a pET32 expression vector. The expression level was augmented several folds after induction with IPTG. This construct produced a recombinant protein approximately 40 kD molecular size. The recombinant protein was purified using the B-per 6×his fusion protein purification kit (PIERCE). Polyclonal antibodies were generated by immunizing rabbits with the purified recombinant protein. Antibody titers were tested by ELISA and Western blot. This antibody was able to detect each ACDK protein corresponding to its predicted size from the brain tissue extracts.

Example 6

ACDK Proteins are Dominantly Localized in the Nucleus

Immunofluorescence staining of permeabilized HeLa cells was performed using the above-described ACDK-specific antibody and a suitable fluorescein-conjugated secondary antibody. Briefly, HeLa cells were cultured on a Lab-Tek 8-well chamber slide (Nalge Nunc) for 48 hrs, then fixed with 4% paraformaldehyde for 15 min, treated with 0.1% Triton X-100 for 10 min, and blocked with 5% goat serum for 30 min. After incubating for 1 hr with 1:500 ACDK-specific antibodies, the slide was incubated for 30 min with Cy2-conjugated AffinPure antibody (Jackson ImmunoResearch). Cells were examined on a confocal microscope (Carl Zeiss). Image capture under confocal laser scan optics revealed that ACDK proteins were predominantly expressed in the nucleus. This result was somewhat surprising since there is no distinct nuclear localization signal within ACDK proteins, except for ACDK1, which contains two weak nuclear localization signals.

In other experiments, the localization of ACDK proteins was compared in cells that are terminally differentiated (i.e., neurons) and cells that were capable of undergoing mitosis (i.e., glial cells). The protocol was similar to that described above for HeLa cells. Neurons were isolated from rat spinal cord and hippocampus, and then cultured in dishes with bedding cells (glial cells). The antibody described above was diluted 1:3000 and allowed to react with the cells. After washing, a labeled secondary goat anti-rabbit IgG antibody was used to detect any anti-ACDK antibody associated with the cells. Fluorescence microscopy showed that ACDK proteins were predominantly localized within the nuclei of the glial cells, but predominantly localized in the cytoplasm of the neurons.

Example 7

Protein Immunoprecipitation

The anti-ACDK-specific antibody generated in rabbits in Example 5 was immobilized on a carbolink matrix employing DSS (Pierce). ACDK proteins from tissue extracts were immunoprecipitated by the CarboLink-immobilized anti-ACDK-specific antibody. Two ACDK members (ACDK3 and ACDK4) were successfully isolated from the brain tissue extracts. Immunoprecipitations of CDK1, CDK2, CDK6 and cyclin A were carried out using agarose-conjugated antibody from Santa Cruz Biotechnology Inc.

Example 8

ACDK Proteins Bind to CDKs In Vitro and In Vivo, and Interact with pRB In Vitro

Figure 3:
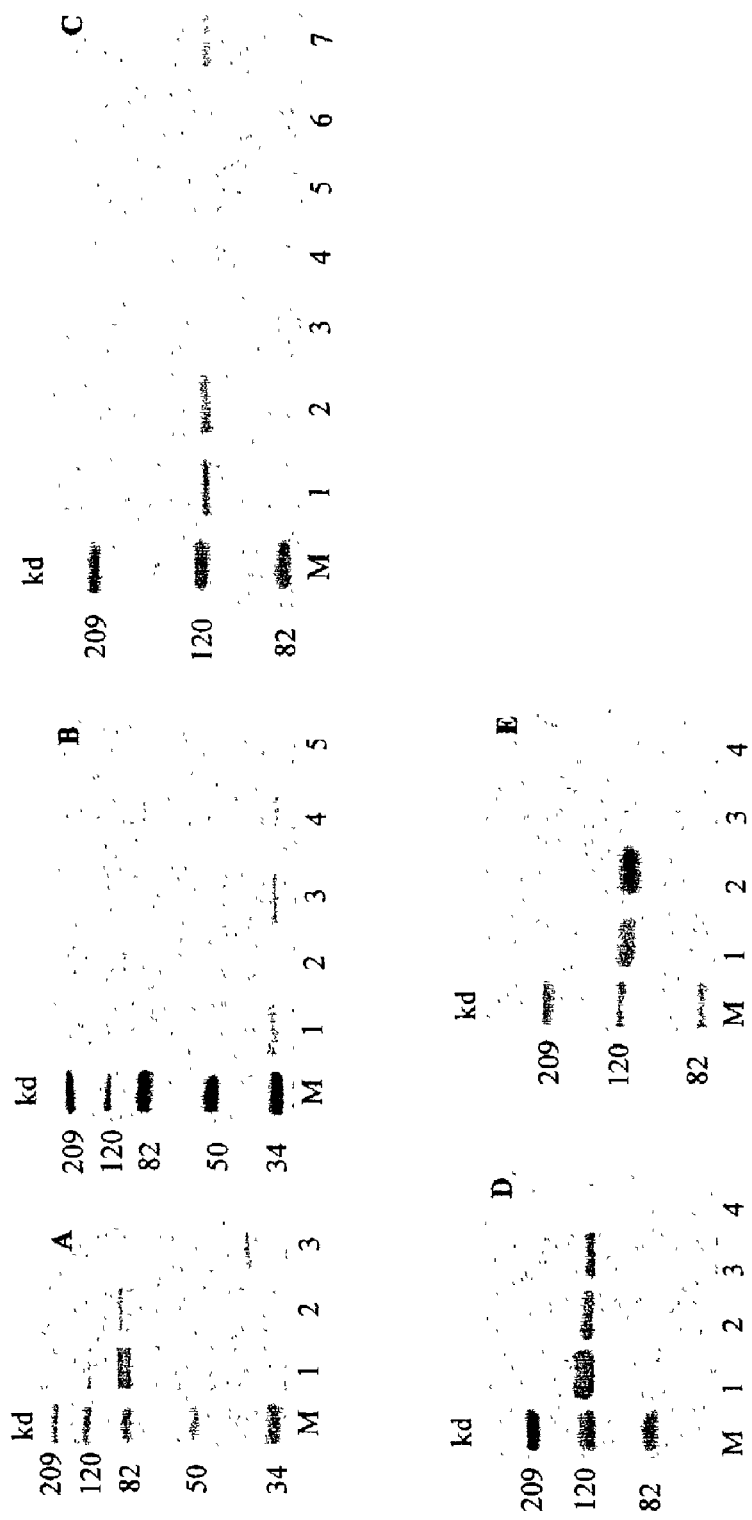
FIG. 3 is a series of Western and Farwestern blots. For Farwestern assays, CDKs and pRB were first immobilized to the PVDF membrane, then incubated with ACDK proteins for 1 hr at room temperature, and subsequently probed with ACDK-specific antibody as a regular Western blot. (a) lane A, Western results from brain tissue. From top to bottom, each band corresponding to ACDK1(119 kd), ACDK2 (105 kd), ACDK4 (95 kd) and ACDK3 (86 kd) respectively. Lane B, represents ACDK3 and ACDK4 which immunoprecipitated from brain tissue extracts. Lane C, was a recombinant protein containing the ACD domain. (b) Lane A, Farwestern result between ACDK and CDK2. The band around 34 kd was CDK2, while the top band was an ACDK-CDK2 complex. Lane B, Western result using immunoprecipitated CDK2 from lane A directly probed with ACDK-specific antibody. Lane C, Farwestern result between ACDK and CDK1. Lane D, Farwestern result between cyclin A and CDK2 (positive control). Lane E, Farwestern result between ACDK and CDK6. (c) Western results for phosphorylated recombinant pRB catalyzed by ACDK-CDK1 complexes. The pRB phosphorylation was carried out with 24 µl of reaction mixture containing 40 mM HEPES, 10 mM $MgCl_2$, 170 µM ATP, 3 µg functional active recombinant $p110^{RB}$ (QED Bioscience Inc.), 3 µg immunoprecicpitated ACDK or cyclin A and 3 µg of immunoprecipitated CDK1. The Western blot was probed with pRB phosphospecific antibodies ($pT^{821}$, $pS^{249}/pT^{252}$, $pT^{356}$, $pT^{826}$ and pS $pS^{807/811}$), however only $pS^{249}/pT^{252}$ generated positive results. Lane A, pRB phosphorylated by ACDK-CDK1. Lane B, pRB phosphorylated by cyclin A-CDK1 (positive control). Lane C, D, E, and F were negative controls. Lane C was unphosphorylated pRB, lane D were pRB and cyclin A alone (without CDK), lane E were pRB and ACDK alone (without CDK), lane F were pRB and CDK1 alone (without cyclin A or ACDK). Lane G was commercially obtained phosphorylated recombinant pRB (positive control). (d) Western results for phosphorylated recombinant pRB catalyzed by ACDK-CDK2 complexes. The same pRB phosphospecific antibodies were used for the Western blots, however, only $pT^{821}$ yielded positive results. Lane A, pRB phosphorylated by ACDK-CDK2. Lane B, pRB phosphorylated by cyclin A-CDK2 (positive control). Lane C, pRB and CDK2 alone (ACDK co-immunoprecipitated with CDK2), Lane D, unphosphorylated pRB (negative control). (e) Farwestern results between ACDK and pRB. Lane A, Farwestern result between phosphorylated recombinant pRB (catalyzed by ACDK/CDK2) and ACDK. Lane B, Farwestern result between immunoprecipitated pRB and ACDK. Lane C, Farwestern result between unphosphorylated recombinant pRB and ACDK. Lane D, Farwestern result between E2F1 and ACDK.

Referring now to FIG. 3, the binding activity between ACDK and CDK molecules was investigated. ACDKs and CDC2 (CDK1), CDK2, and CDK6 were immunoprecipitated as described above, and used to assess binding by Farwestern blotting. Briefly, native CDKs were first immobilized onto a PVDF membrane. The membrane was subsequently incubated with ACDK proteins for 1 hr at room temperature, and then probed with the ACDK-specific antibody as regular Western blot (ACDK proteins bound to the immobilized CDKs would be detected as positive bands corresponding to the CDKs' sizes). Cyclin A was used as positive control. Interestingly, ACDK proteins strongly bound to CDK2 and CDK1, but not to CDK6. Furthermore, for CDK2, the Farwestern analysis showed two bands, one corresponding to CDK2, and another band to an ACDK/CDK2 complex (implying that ACDK indeed bound to CDK2 in vivo). A Western blot using denatured immunoprecipitated CDK2 directly probed with ACDK-specific antibody confirmed this result.

Whether ACDK could interact with other cell cycle regulatory proteins, such as pRB and E2F1, was also investigated. The results showed that ACDK strongly bound to immunoprecipitated pRB as well as phosphorylated recombinant pRB, but the binding activity between the unphosphorylated recombinant pRB was hardly detectable, and there was no binding activity between ACDK and E2F1. The only activators for CDKs known to interact with pRB are the D-type cyclins. Unlike D-type cyclins, ACDK proteins do not possess LXCXE motif.

Example 9

ACDK/CDK Complexes Phosphorylate pRB In Vitro

Referring again to FIG. 3, a phosphorylation assay was employed to determine whether ACDK proteins could activate CDKs to phosphorylate the retinoblastoma protein (pRB). After the kinase reaction, a Western blot was performed using 7 different pRB phosphospecific antibodies to detect which sites on pRB were phosphorylated. This assay showed that pRB was phosphorylated by ACDK-CDK2 complex at threonine 821, and by ACDK-CDK1 complex at serine 249 and/or threonine 252. Moreover, according to the observed phosphorylation efficiency, ACDK-CDK2 activity was approximately 2-fold higher than that of cyclin A-CDK2 complex, suggesting that the sequential phosphorylation events of pRB that are involved in cell cycle progression are carried out by ACDK-CDK complexes. For example, it has been demonstrated that phosphorylation of threonine 821 disrupts interaction of pRB with proteins containing the sequence LXCXE, including E2F. This disruption creates free E2F that is then available to transcribe genes required for S phase entry.

Example 10

Disregulation of ACDK Expression Induces Abnormal Cell Cycle Progression and Apoptosis Stable cell lines expressing sense and antisense ACDK constructs were made with the pBIG2i inducible tet-on vector using an ACDK4 coding sequence in HeLa cells. Six sense clones and six antisense clones were selected for the following experiments. The ectopic message and protein were first examined by quantitative RT-PCR and Western blots for the cell clones selected. For sense clones, Western blotting showed significantly higher ACDK4 protein. Conversely, the antisense clones showed significantly lower ACDK4 protein.

In order to address the issue of cell cycle regulation by ectopic ACDK4 message, a cell proliferation assay employing BrdU incorporation was performed. The cells were first induced with doxcyclin for 48 hrs, then the BrdU label was added to each cell clone. The cells were cultured for additional five hrs to let the BrdU incorporate into the cells. The results indicated that, compared to controls, the sense clones grew significantly faster (O.D. 0.3048) while the antisense clones were significantly inhibited (O.D. 0.1668). (P<0.0001).

Cell cycle progression was analyzed by flow cytometry. This analysis showed that significantly more of the antisense clones accumulated in S phase compared to the sense clones (31.4% v. 27.49%) (P=0.0185). Moreover, variations within sense clones or antisense clones were consistent with their ectopic message levels. For example, cells of antisense clone B had the highest levels of ectopic message and the highest accumulation in S phase (41.42%).

To evaluate the potential role of ACDKs in apoptosis, a TdT-FragEL DNA fragmentation assay for apoptosis was carried out using the sense and anti-sense cell clones described above. Four time points were checked, including 48 hrs, 56 hrs, 60 hrs and 72 hrs. Apoptosis was detected in sense clones after 60 hrs induction. No apoptosis was observed at 48 hrs and 56 hrs. The average apoptosis rate was approximately 1%. The apoptosis rate was related to the ectopic message level. Higher ectopic protein levels correlated with higher apoptosis rates. Apoptosis was also detected in the antisense clones. However, the apoptosis rate (0.5%) was lower than the sense clones. No apoptosis was detected in the untransfected control cells.

Example 11

Molecular Cloning of mACDK, the Mouse Homologue of ACDK Gene Family

To clone mACDK, the mouse homologue of ACDK gene family, the mouse EST database was searched using both human ACDK cDNAs and the predicted protein sequences. The mouse homologue EST markers corresponding to each ACDK member were then identified. A1614651 corresponds to mACDK1 (SEQ ID NO:5), W98010 corresponds to mACDK2 (SEQ ID NO:6), AI606540 corresponds to mACDK3 (SEQ ID NO:7), and AA795502 corresponds to mACDK4 (SEQ ID NO:8). These clones were ordered from Genome Systems, and the inserts were fully sequenced. Primers from both ends were designed to amplify the inserts. The cDNA sequences were confirmed by directly sequencing the PCR products. The sequence from each clone was used to search the mouse EST database again for expanding 5' end sequence.

To identify the full-length cDNA sequence, a forward primer within human 5' cDNA coding region (hf1, after start codon) and a mouse reverse primer (mr2) from the mACDK coding sequence was used to amplify the homologue sequence using mouse cDNA at very low annealing temperature (45–50° C.). For nested PCR, an inside reverse primer from mouse sequence (mr1) and the same human forward primer was used to amplify the specific mouse gene from the first round PCR products at high annealing temperature. The expected PCR products are directly excised from agarose gel and sequenced by ABI377 automatic sequencer. The sequence is further confirmed using forward primer from newly identified sequence and reverse primer from known sequence.

Once most of the coding sequence is identified, the 5' untranslated regions of the sequences was determined by direct sequencing of the BAC DNA. Primers within 3' untranslated region were used to screen a mouse BAC library for identification of BAC clones containing each mACDK member. 5' untranslated regions of the sequences are identified by directly sequencing BAC DNA using primers within the first exon. Several forward primers before the start codon and a reverse primer after the first exon are used to test the 5' untranslated sequence. The predicted protein sequences for mACDK1, mACDK2, mACDK3, and mACDK4 are listed as SEQ ID NOs: 13, 14, 15, and 16, respectively.

OTHER EMBODIMENTS

This description has been by way of example of how the compositions and methods of invention can be made and carried out. Those of ordinary skill in the art will recognize that various details may be modified in arriving at the other detailed embodiments, and that many of these embodiments will come within the scope of the invention.

Therefore, to apprise the public of the scope of the invention and the embodiments covered by the invention, the following claims are made.

What is claimed is:

1. A purified nucleic acid comprising a nucleotide sequence that encodes a native activator of cyclin-dependent kinase (ACDK) consisting of SEQ ID NO:9.

2. The nucleic acid of claim 1, wherein the nucleotide sequence is SEQ ID NO:1.

3. A vector comprising the nucleic acid of claim 1.

4. The vector of claim 3, wherein said nucleic acid is operably linked to one or more expression control sequences.

5. A cell comprising the nucleic acid of claim 1.

6. The cell of claim 5, wherein the nucleic acid is comprised in a vector.

* * * * *